US005625079A

United States Patent [19]
Wollowitz et al.

[11] Patent Number: 5,625,079
[45] Date of Patent: Apr. 29, 1997

[54] SYNTHESIZING PSORALEN COMPOUNDS USEFUL AS INTERMEDIATES

[75] Inventors: Susan Wollowitz, Walnut Creek; Stephen T. Isaacs, Orinda; Henry Rapoport; Hans P. Spielmann, both of Berkeley; Aileen Nerio, Santa Clara, all of Calif.

[73] Assignee: Cerus Corporation, Concord, Calif.

[21] Appl. No.: 462,377

[22] Filed: Jun. 5, 1995

Related U.S. Application Data

[60] Division of Ser. No. 212,113, Mar. 11, 1994, abandoned, which is a continuation-in-part of Ser. No. 83,459, Jun. 28, 1993, Pat. No. 5,399,719.

[51] Int. Cl.$^6$ .................................................. C07D 493/00
[52] U.S. Cl. ........................................................... 549/282
[58] Field of Search ............................................. 549/282

[56] References Cited

U.S. PATENT DOCUMENTS

| | | | |
|---|---|---|---|
| 4,124,598 | 11/1978 | Hearst et al. | 260/343.21 |
| 4,157,723 | 6/1979 | Granzow et al. | 141/1 |
| 4,169,204 | 9/1979 | Hearst et al. | 546/270 |
| 4,196,281 | 4/1980 | Hearst et al. | 536/28 |
| 4,216,154 | 8/1980 | Kaufman | 260/343.21 |
| 4,235,781 | 11/1980 | Kaufman | 260/343 |
| 4,265,280 | 5/1981 | Ammann et al. | 141/98 |
| 4,269,851 | 5/1981 | Kaufman | 424/279 |
| 4,269,852 | 5/1981 | Kaufman | 424/279 |
| 4,279,922 | 7/1981 | Kaufman | 424/279 |
| 4,294,822 | 10/1981 | Kaufman | 424/59 |
| 4,294,847 | 10/1981 | Kaufman | 424/279 |
| 4,298,614 | 11/1981 | Kaufman | 424/279 |
| 4,328,239 | 5/1982 | Kaufman | 424/279 |
| 4,370,344 | 1/1983 | Kaufman | 424/279 |
| 4,412,835 | 11/1983 | Spencer | 604/29 |
| 4,683,195 | 7/1987 | Mullis et al. | 435/6 |
| 4,683,202 | 7/1987 | Mullis | 435/91 |
| 4,727,027 | 2/1988 | Wiesehahn et al. | 435/173 |
| 4,748,120 | 5/1988 | Wiesehahn et al. | 435/173 |

OTHER PUBLICATIONS

Melnick, J.L., "Viral Hepatitis: One Disease but Multiple Viruses," Abstracts of Virological Safety Aspects of Plasma Derivatives, Cannes (France), Nov. 3–6 (1992) p. 9.
International Forum: "How Frequent is Posttransfusion Hepatitis after the Introduction of 3rd Generation Donor Screening for Hepatitis B? What is its Probable Nature?" Vox Sang 32:346 (1977).
Ward, J.W., et al., "Transmission of Human Immunodeficiency Virus (HIV) by Blood Transfusions Screened as Negative for HIV Antibody," N. Engl. J. Med., 318:473 (1988).
Schmunis, G.A., "*Trypanosoma cruzi*, the etiologic agent of Chagas' disease: status in the blood supply in endemic and nonendemic countries," Transfusion 31:547–557 (1992).
Hilfenhaus, J., et al., "A strategy for testing established human plasma protein manufacturing procedures for their ability to inactivate or eliminate human immunodeficiency virus," J. Biol. Std. 70:589 (1987).

Horowitz, B., et al., "Inactivation of viruses in labile blood derivatives," Transfusion 25:516 (1985).
Moroff, G., et al., "The influence of irradiation on stored platelets," Transfusion 26:453 (1986).
Prince, A.M., et al., "β–Propiolactone/Ultraviolet Irradiation: A review of Its Effectiveness for Inactivation of Viruses in Blood Derivatives," Reviews of Infect. Diseases 5:92–107 (1983).
Matthews, J.L., et al., "Photodynamic therapy of viral contaminants with potential for blood banking applications," Transfusion 28:81–83 (1988).
North, J., et al., "Photodynamic inactivation of retrovirus by benzoporphyrin derivative: a feline leukemia virus model," Transfusion 32:121–128 (1992).
Sieber, F., et al,. "Invitation of Friend Erythroleukemia Virus and Friend Virus—Transformed Cells by Merocyanine 540–Mediated Photosensitization," Blood 73;345–350 (1989).
Rywkin, S., et al., "In Vivo Circulatory Survival of Photochemically Treated Rabbit Red Blood Cells with Aluminum Phthalocyanine Derivatives," Blood 78(Suppl 1): 352A (Abstract) (1991).
Proudouz, K.N., et al., "Use of Laser U-V for Inactivation of Virus in Blood Platelets," Blood 70:589, (1987).
G.D. Cimino, et al., "Psoralens as Photoactive Probes of Nucleic Acid Structure an Function: Organic Chemistry, Photochemistry, and Biochemistry," Ann. Rev. Biochem. 54:1151 (1985).
Hearst, et al., "The Reaction of the Psoralens with Deoxyribonucleic Acid," Quart. Rev. Biophys. 17:1 (1984).
S.T. Isaacs, et al., "Synthesis and Characterization of New Psoralen Derivatives with Superior Photoreactivity with DNA and RNA," Biochemistry 16:1058 (1977).
S.T. Isaacs, et al., "A Photochemical Characterization of Reactions of Psoralen Derivatives with DNA," Trends in Photobiology (Plenum) pp. 279–294 (1982).
J. Tessman, et al,. "Photochemistry of the Furan–Side 8–Methoxypsoralen–Thymide Monoadduct Inside the DNA Helix. conversion to Diadduct and to Pyrone–Side Monoadduct," Biochem. 24:1669 (1985).
H.J. Alter, et al., "Photochemical Decontamination of Blood Components Containing Hepatitis B and Non–A, Non–B, Virus," The Lancet (ii:1446) (1988).
L. Lin, et al., "Use of 8–Methoxypsoralen and Long–Wavelength Ultraviolet Radiation for Decontamination of Platelet Concentrates," Blood 74:517 (1989).
P. Morel, et al., "Photochemical Inactivation of Viruses and Bacteriophage in Plasma and Plasma Fractions," Blood Cells 18:27 (1992).

(List continued on next page.)

*Primary Examiner*—Amelia Owens
*Attorney, Agent, or Firm*—Peter G. Carroll; Kathryn P. Wilke

[57] ABSTRACT

Synthesis of 4,8-dialkyl-4'-bromomethyl-5'-methylpsoralen and 4,8-dialkyl-5'-bromomethyl-4'-methylpsoralen compounds useful as intermediates.

2 Claims, 35 Drawing Sheets

OTHER PUBLICATIONS

R.Y. Dodd, et al., "Inactivation of Viruses in Platelet Suspensions that Retain Their In Vitro Characteristics: Comparison of Psoralen–ultraviolet A and Merocyanine 540 Visible Light Methods," Transfusion 31:483–490 (1991).

H. Margolis–Nunno, et al., "Photochemical Virus Sterilization in Platelet Concentrates with Psoralen Derivatives," Thromb Haemostas 65:1162 (Abstract) (1991).

C.V. Hanson, "Photochemical Inactivation of Viruses with Psoralens: An Overview," Blood Cells: 18:7–25 (1992).

Hearst, J.E., and Thiry, L., "The photoinactivation of an RNA animal virus, vesicular stomatitis virus, with the aid of newly synthesized psoralen derivatives," Nucleic Acids Research, 4:1339 (1977).

Hyde and Hearst, "Binding of Psoralen Derivatives to DNA and Chromatin: Influence of the Ionic Environment of Dark Binding and Photoreactivity," Biochemistry, 17, 1251 (1978).

Thompson, et al., J. Mol. Biol., "Determination of the Secondary Structure of *Drosophila Melanogaster* 5 S RNA by Hydroxymethyltrimethylpsoralen Crosslinking," 147:417 (1981).

Thompson, et al., "Dependence of 4'–(Hydroxymethyl)–4, 5',8–trimethylpsoralen Photoaddition on the Conformation of Ribonucleic Acid," Biochemistry 21:1363 (1982).

Isaacs, S.T., G. Wiesehahn and L.M. Hallick, "In Vitro Characterization of the Reaction of Four Psoralen Derivatives with DNA," NCI Monograph 66:21 (1984).

McLeod, et al., "Synthesis of Benzofuranoid Systems. I. Furocoumarins, Benzofurans and Dibenzofurans," Tetrahedron Letters 237 (1972).

Adams, et al., "The Pechmann Reaction," Organic Reactions, vol. VII. Chapter 1, Wiley, NY (1953).

Bender, et al., "Psoralen Synthesis. Improvements in Furan Ring Formation. Application to the Synthesis of 4,5',8–Trimethylpsoralen," J. Org. Chem. 44:2176 (1979).

Olah and Kuhn, "Selective Friedel–Crafts Reactions. I. Boran Halide Catalyzed Haloalkylation of Benzene and Alkylbenzenes with Flurohaloalkanes," J. Org. Chem. 29, 2317 (1964).

Friedel–Crafts and Related Reactions, vol. II, Part 2, Olah, ed., Interscience, NY, p. 749 (1964).

Lee, B.L., et al., "Interaction of Psoralen–Derivatized Oligodeoxyrionucleoside Methylphosphonates with Single–Stranded DNA," Biochemistry, 27,3197–3203 (1988).

Goldenberg, M., et al., "Synthesis and Properties of Novel Psoralen Derivatives," Biochemistry 27:6971 (1988).

Larock, "Alkanes and Arenes," Comprehensive Organic Transformations, Chapter 1, p. 5, VCH Publishers, NY (1989).

Isaacs, et al., "Synthesis of Deuterium and Tritium Labeled Psoralens," J. Labelled Cmpds. Radiopharm., 19, 345 (1982).

Durst, T., "Dimethylsulfoxide (DMSO) in Organic Synthesis," Adv. Org. Chem. 6:285 (1969).

Morrow, J.F., et al., "Septic Reactions to Platelet Transfusions," JAMA 266:555–558 (1991).

Bertolini, F., et al., "Platelet Quality After 15–day Storage of Platelet Concentrates Prepared from Buffy Coats and Stored in a Glucose–Free Crystalloid Medium," Transfusion 32:152–156 (1992).

D.M. Maron and B.N. Ames, "Revised methods for the Salmonella mutagenicity test," Mutation Research, 113:173 (1983).

Kaufman, et al., "Reactions of Furocoumarins. II(1). Synthetic Aminomethyl Psoralens via Chloromethylation of Benzylic Bromination," J. Heterocyclic Chem. 19:1051 (1982).

Hanson, C.V., et al., "Application of a Rapid Microplaque assay for Determination of Human Immunodeficiency Virus Neutralizing Antibody Titers," J. Clin. Micro 28:2030 (1990).

Metzelaar, M.J., "Studies on the Expression of Activation–Markers on Human Platelets," (Thesis) (1961).

Moroff, G., et al. "Factors Influencing Changes in pH during Storage of Platelet Concentrates at 20–24°C," Vox Sang 43;33–45 (1982).

Stack, G., "Storage of Platelet Concentrate," Blood Separation and Platelet Fractionation, pp. 99–125 (1991).

German Patent No. P 39 28 900.1, Issued Mar. 7, 1991, Name: Weickmann, et al., For: "Neue Nucleotidderivate, ihre Herstellung und ihre Verwendung," Filed Aug. 31, 1989.

4'-CMT
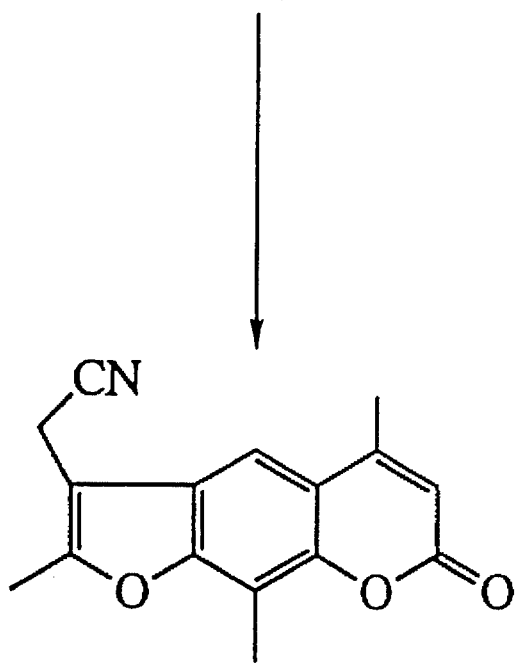
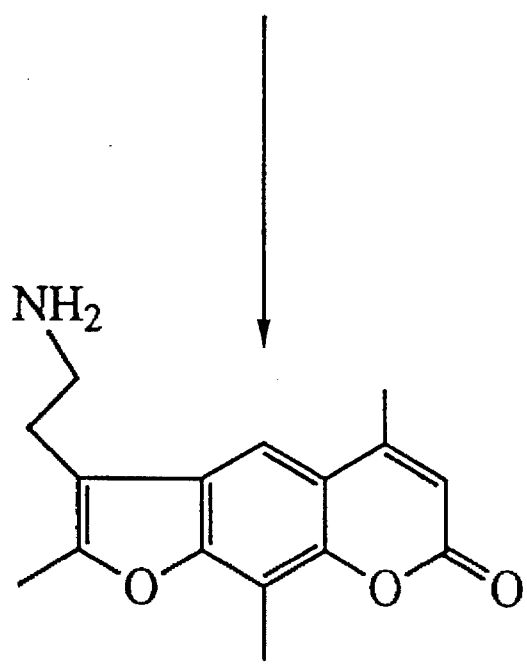
3
FIG. 5E

SYNTHESIZING PSORALEN COMPOUNDS USEFUL AS INTERMEDIATES

The present application is a divisional of application Ser. No. 08/212,113 filed Mar. 11, 1994, now abandoned which is a continuation-in-part of application Ser. No. 08/083,459 filed Jun. 28, 1993, which issued as U.S. Pat. No. 5,399,719 on Mar. 21, 1995.

FIELD OF THE INVENTION

The present invention provides new psoralens and methods of synthesis of new psoralens having enhanced ability to inactivate pathogens in blood products in the presence of ultraviolet light, without significantly effecting blood product function or exhibiting mutagenicity.

BACKGROUND

Pathogen contamination within the blood supply remains an important medical problem throughout the world. Although improve testing methods for hepatitis B (HBV), hepatitis C (HCV), and HIV have markedly reduce the incidence of transfusion associated diseases, the public is losing trust in the safety of the blood supply due to publicity of cases of transfusion related transmission of these viruses.

For example, the recent introduction of a blood test for HCV will reduce transmission of this virus; however, it has a sensitivity of only 67% for detection of probable infectious blood units. HCV is responsible for 90% of transfusion associated hepatitis. Melnick, J. L., abstracts of Virological Safety Aspects of Plasma, Cannes, Nov. 3–6 (1992) (page 9). It is estimated that, with the test in place, the risk of infection is 1 out of 3300 units transfused.

Similarly, while more sensitive seriological assays are in place for HIV-1 and HBV, these agents can nonetheless he transmitted by seronegative blood donors. International Forum: Vox Sang 32:346 (1977). Ward, J. W., et al., N. Engl. J. Med., 318:473 (1988). Up to 10% of total transfusion-related hepatitis and 25% of severe icteric cases are due to the HBV transmitted by hepatitis B surface antigen (HBasAg) negative donors, to date, and remain a potential threat to transfusion safety. Schmunis, G. A., Transfusion 31:547–557 (1992). In addition, testing will not insure the safety of the blood supply against future unknown pathogens that may enter the donor population resulting in transfusion associated transmission before sensitive tests can be implemented.

Even if seroconversion tests were a sufficient screen, they may not be practical in application. For example, CMV (a herpes virus) and parvo B19 virus in humans are common. When they occur in healthy, immunocompetent adults, they nearly always result in asymptomatic seroconversion. Because such a large part of the population is seropositive, exclusion of positive units would result in substantial limitation of the blood supply.

An alternative approach to eliminate transmission of viral diseases through blood products is to develop a means to inactivate pathogens in transfusion products. Development of an effective technology to inactivate infectious pathogens in blood products offers the potential to improve the safety of the blood supply, and perhaps to slow the introduction of new tests, such as the recently introduced HIV-2 test, for low frequency pathogens. Ultimately, decontamination technology could significantly reduce the cost of blood products and increase the availability of scarce blood products.

To be useful, such an inactivation method i) must not adversely effect the function for which the blood product is transfused, ii) must thoroughly inactivate existing pathogens in the blood product, and iii) must not adversely effect the recipients of the blood product. Several methods have been reported for the inactivation or elimination of viral agents in erythrocyte-free blood products. However, most of these techniques are completely incompatible with maintenance of the function of platelets, an important blood product. Examples of these techniques are: heat (Hilfenhous, J., et al., J. Biol. Std. 70:589 (1987)), solvent/detergent treatment (Horowitz, B., et al., Transfusion 25:516 (1985)), gamma-irradiation (Moroff, G., et al., Transfusion 26:453 (1986)), UV radiation combined with beta propriolactone, (Prince A. M., et al., Reviews of Infect. Diseases 5:92–107 (1983)), visible laser light in combination with hematoporphyrins (Matthews J. L., et al., Transfusion 28:81–83 (1988); North J., et al., Transfusion 32:121–128 (1992)), use of the photoactive dyes aluminum phthalocyananine and merocyanine 540 (Sieber F., et al., Blood 73:345–350 (1989); Rywkin S., et al., Blood 78(Suppl 1): 352a (Abstract) (1991)) or UV alone (Proudouz, K. N., et al., Blood 70:589 (1987)).

Other methods inactivate viral agents by treatment with furocoumarins, such as psoralens, in the presence of ultraviolet light. Psoralens are tricyclic compounds formed by the linear fusion of a furan ring with a coumarin. Psoralens can intercalate between the base pairs of double-stranded nucleic acids, forming covalent adducts to pyrimidine bases upon absorption of long wave ultraviolet light (UVA). G. D. Cimino et al., Arm. Rev. Biochem. 54:1151 (1985); Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977); S. T. Isaacs et al., Trends in Photobiology (Plenum) pp. 279–294 (1982); J. Tessman et al., Biochem. 24:1669 (1985); Hearst et al., U.S. Pat. Nos. 4,124,598, 4,169,204, and 4,196,281, hereby incorporated by reference.

The covalently bonded psoralens act as inhibitors of DNA replication and thus have the potential to stop the replication process. Due to this DNA binding capability, psoralens are of particular interest in relation to solving the problems inherent in creating and maintaining a pathogen blood supply. Some known psoralens have been shown to inactivate viruses in some blood products. H. J. Alter et al., The Lancet (ii:1446) (1988); L. Lin et al., Blood 74:517 (1989) (decontaminating platelet concentrates); G. P. Wiesehahn et al., U.S. Pat. Nos. 4,727,027 and 4,748,120, hereby incorporated by reference, describe the use of a combination of 8-methoxypsoralen (8-MOP) and irradiation. P. Morel et al., Blood Cells 18:27 (1992) show that 300 µg/mL of 8-MOP together with ten hours of irradiation with ultraviolet light can effectively inactivate viruses in human serum. Similar studies using 8-MOP and aminomethyltrimethyl psoralen (AMT) have been reported by other investigators. Dodd R Y, et al., Transfusion 31:483–490 (1991); Margolis-Nunno, H., et al., Thromb Haemostas 65:1162 (Abstract)(1991). Indeed, the photoinactivation of a broad spectrum of microorganisms has been established, including HBV, HCV, and HIV, under conditions different from those used in the present invention and using previously known psoralen derivatives. [Hanson, C. V., Blood Cells: 18:7–24 (1992); Alter, H. J., et al., The Lancet ii:1446 (1988); Margolis-Nunno, H. et al., Thromb Haemostas 65:1162 (Abstract) (1991).]

Psoralen photoinactivation is only feasible if the ability of the psoralen to inactivate viruses is sufficient to ensure a safety margin in which complete inactivation will occur. On the other hand, the psoralen must not be such that it will cause damage to blood products. The methods just described, when applied using known psoralens, require the use of difficult and expensive procedures to avoid causing damage to blood products. For example, some compounds and protocols have necessitated the removal of molecular oxygen from the reaction before exposure to light, to prevent damage to blood products from oxygen radicals produced during irradiation. See L. Lin et al., Blood 74:517 (1989); U.S. Pat. No. 4,727,027, to Wiesehahn. This is a costly and time consuming procedure.

Finally, some commonly known compounds used in photochemical decontamination (PCD) exhibit undesirable mutagenicity which appears to increase with increased ability to kill virus. In other words, the more effective the known compounds are at inactivating viruses, the more injurious the compounds are to the recipient, and thus, the less useful they are at any point in an inactivation system of products for in vivo use.

A new psoralen compound is needed which displays improved ability to inactivate pathogens and low mutagenicity, without causing significant damage to blood products for which it is used, and without the need to remove oxygen, thereby ensuring safe and complete inactivation of pathogens in blood decontamination methods.

SUMMARY OF THE INVENTION

The present invention provides new psoralens and methods of synthesis of new psoralens having enhanced ability to inactivate pathogens in the presence of ultraviolet light which is not linked to mutagenicity. The present invention also provides methods of using new and known compounds to inactivate pathogens in health related products to be used in vivo and in vitro, and particularly, in blood products and blood products in synthetic media.

The present invention contemplates a method of inactivating pathogens in a platelet preparation comprising, in the following order: a) providing, in any order, i) a synthetic media comprising a compound selected from the group consisting of 4'-primaryamino-substituted psoralens and 5'-primaryamino-substituted psoralens; ii) photoactivating means for photoactivating said compound; and iii) a platelet preparation suspected of being contaminated with a pathogen having nucleic acid; b) adding said synthetic media to said platelet preparation; and c) photoactivating said compound so as to prevent the replication of substantially all of said pathogen nucleic acid, without significantly altering the biological activity of said platelet preparation. The pathogen may be a virus, or a bacteria. Its nucleic acid may be single stranded or double stranded, DNA or RNA. The photoactivating means comprises a photoactivation device capable of emitting a given intensity of a spectrum of electromagnetic radiation comprising wavelengths between 180 nm and 400 nm. The intensity may be between 1 and 30 mW/cm² and the platelet preparation is exposed to said intensity for between 1 second and thirty minutes. The spectrum of electromagnetic radiation may be wavelengths between 320 nm and 380 nm.

In one embodiment the compound displays low mutagenicity. It may be added to said platelet preparation at a concentration of between 0.1 and 250 µM. And the method may be performed without limiting the concentration of molecular oxygen.

The 4'-primaryamino-substituted psoralen may comprise: a) a substituent $R_1$ on the 4' carbon atom, selected from the group comprising:

—$(CH_2)_u$—$NH_2$,
—$(CH_2)_w$—$R_2$—$(CH_2)_z$—$NH_2$,
—$(CH_2)_w$—$R_2$—$(CH_2)_x$—$R_3$—$(CH_2)_z$—$NH_2$, and
—$(CH_2)_w$—$R_2$—$(CH_2)_x$—$R_3$—$(CH_2)_y$—$R_4$—$(CH_2)_z$—$NH_2$;

wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4,5', and 8 carbon atoms respectively, independently selected from the group comprising H and $(CH_2)_v CH_3$, where v is a whole number from 0 to 5; or a salt thereof.

Alternatively, the 5'-primaryamino-substituted psoralen comprises: a) a substituent $R_1$ on the 5' carbon atom, selected from the group comprising:

—$(CH_2)_u$—$NH_2$,
—$(CH_2)_w$—$R_2$—$(CH_2)_z$—$NH_2$,
—$(CH_2)_w$—$R_2$—$(CH_2)_x$—$R_3$—$(CH_2)_z$—$NH_2$, and
—$(CH_2)_w$—$R_2$—$(CH_2)_x$—$R_3$—$(CH_2)_y$—$R_4$—$(CH_2)_z$—$NH_2$;

wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5, and where when $R_1$ is selected from the group comprising —$(CH_2)_u$—$NH_2$, $R_6$ is H; or a salt thereof.

Finally, the 5'-primaryamino-substituted psoralen may comprise: a) a substituent $R_1$ on the 5' carbon atom, selected from the group comprising:

—$(CH_2)_u$—$NH_2$,
—$(CH_2)_w$—$R_2$—$(CH_2)_z$—$NH_2$,
—$(CH_2)_w$—$R_2$—$(CH_2)_x$—$R_3$—$(CH_2)_z$—$NH_2$, and
—$(CH_2)_w$—$R_2$—$(CH_2)_x$—$R_3$—$(CH_2)_y$—$R_4$—$(CH_2)_z$—$NH_2$;

wherein $R_2$, $R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_v CH_3$, where v is a whole number from 0 to 5; or a salt thereof.

In one embodiment, at least two compounds are present. In another embodiment, the synthetic media further comprises sodium acetate, potassium chloride, sodium chloride, sodium citrate, sodium phosphate and magnesium chloride, and may also include mannitol and/or glucose.

In one embodiment, the synthetic media is contained in a first blood bag and said platelet preparation is contained in a second blood bag, the synthetic media being added to the platelet preparation in step (b) by expressing the synthetic media from the first blood bag into the second blood bag via a sterile connection.

In a preferred embodiment, the compound is either 5'-(4-amino-2-oxa)butyl-4,4',8-trimethylpsoralen or 4'-(4-amino-2-oxa)butyl-4,5',8-trimethylpsoralen.

In one embodiment, the method described above includes administering said platelet preparation by intravenous infusion to a mammal.

In another embodiment, method of inactivating pathogens in a platelet preparation comprising, in the following order:

a) providing, in any order, i) a synthetic media comprising a buffered saline solution and a compound displaying low mutagenicity, selected from the group consisting of 4'-primaryamino-substituted psoralens and 5'-primaryamino-substituted psoralens, contained in a first blood bag; ii) photoactivating means for photoactivating said compound; and iii) a platelet preparation suspected of being contaminated with a pathogen having nucleic acid, contained in a second blood bag; b) adding said synthetic media to said platelet preparation by expressing said synthetic media from said first blood bag into said second blood bag via sterile connection means; and c) photoactivating said compound so as to prevent the replication of substantially all of said pathogen nucleic acid, without significantly altering the biological activity of said platelet preparation. The pathogen may be a virus, or a bacteria. Its nucleic acid may be single stranded or double stranded, DNA or RNA. The photoactivating means comprises a photoactivation device capable of emitting a given intensity of a spectrum of electromagnetic radiation comprising wavelengths between 180 nm and 400 nm. The intensity may be between 1 and 30 mW/cm$^2$ and the platelet preparation is exposed to said intensity for between 1 second and thirty minutes. The spectrum of electromagnetic radiation may be wavelengths between 320 nm and 380 nm.

In one embodiment the compound displays low mutagenicity. It may be added to said platelet preparation at a concentration of between 0.1 and 250 μM. And the method may be performed without limiting the concentration of molecular oxygen.

The 4'-primaryamino-substituted psoralen may comprise: a) a substituent $R_1$ on the 4' carbon atom, selected from the group comprising:

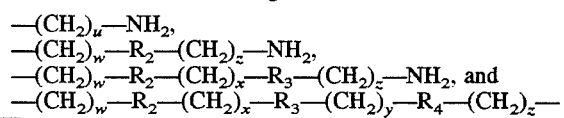

wherein $R_2$, $R_3$, and $R_4$ are independently selected from the group comprising O and NH, in which u is a whole number from 1 to 10, w is a whole number from 1 to 5, x is a whole number from 2 to 5, y is a whole number from 2 to 5, and z is a whole number from 2 to 6; and b) substituents $R_5$, $R_6$, and $R_7$ on the 4, 5', and 8 carbon atoms respectively, independently selected from the group comprising H and $(CH_2)_vCH_3$, where v is a whole number from 0 to 5; or a salt thereof.

Alternatively, the 5'-primaryamino-substituted psoralen comprises: a) a substituent $R_1$ on the 5' carbon atom, selected from the group comprising:

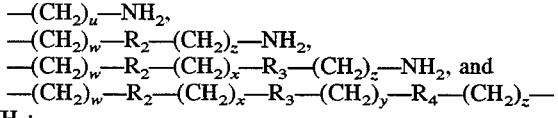

wherein $R_2$, $R_3$, and $R_4$ are independently selected from the group comprising O and NH, and in which u is a whole number from 1 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5, and where when $R_1$ is selected from the group comprising $-(CH_2)_u-NH_2$, $R_6$ is H; or a salt thereof.

Finally, the 5'-primaryamino-substituted psoralen may comprise: a) a substituent $R_1$ on the 5' carbon atom, selected from the group comprising:

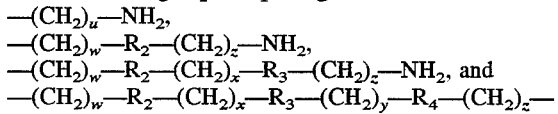

wherein $R_2$, $R_3$, and $R_4$ are independently selected from the group comprising O and NH, and in which u is a whole number from 3 to 10, w is a whole number from 1 to 5, x is a whole number from 2 to 5, y is a whole number from 2 to 5, and z is a whole number from 2 to 6; and, b) substituents $R_5$, $R_6$, and $R_7$ on the 4, 4', and 8 carbon atoms respectively, independently selected from the group comprising H and $(CH_2)_vCH_3$, where v is a whole number from 0 to 5; or a salt thereof.

In one embodiment, at least two compounds are present. In another embodiment, the synthetic media further comprises sodium acetate, potassium chloride, sodium chloride, sodium citrate, sodium phosphate and magnesium chloride, and may also include mannitol and/or glucose.

In one embodiment, the synthetic media is contained in a first blood bag and said platelet preparation is contained in a second blood bag, the synthetic media being added to the platelet preparation in step (b) by expressing the synthetic media from the first blood bag into the second blood bag via a sterile connection.

In a preferred embodiment, the compound is either 5'-(4-amino-2-oxa)butyl-4,4',8-trimethylpsoralen or 4'-(4-amino-2-oxa)butyl-4,5',8-trimethylpsoralen.

In one embodiment, the method described above includes administering said platelet preparation by intravenous infusion to a mammal.

The present inventions also contemplates a method of synthesizing 4,8-dialkyl-5'-bromomethyl-4'-methylpsoralens, without performing bromomethylation, comprising: a) providing 4,8-dialky-7-(1-methyl-2-oxopropyloxy)psoralen; d) stirring 4,8-dialky-4',5'-dimethylpsoralen in carbon tetrachloride to obtain 4,8-dialkyl-5'-bromomethyl-4'-methylpsoralen. A method of synthesizing 4,8-dialkyl-4'-bromomethyl-5'-methylpsoralens, without performing bromomethylation, is contemplated, comprising: a) providing 4,8-dialky-7-(1-methyl-2-oxopropyloxy)psoralen; d) stirring 4,8-dialky-4',5'-dimethylpsoralen in methylene chloride to obtain 4,8-dialkyl-4'-bromomethyl-5'-methylpsoralen.

A novel compound is also contemplated, having the formula:

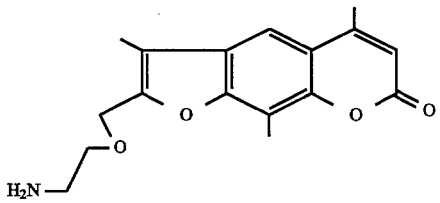

or a salt thereof.

Finally, the present invention contemplates compositions having antiviral properties. The first comprising an aqueous solution of a 4'-primaryamino-substituted psoralen and platelets suitable for in vivo use. One embodiment, further comprises a synthetic media, comprising sodium acetate, potassium chloride, sodium chloride, sodium citrate, sodium phosphate and magnesium chloride and optionally mannitol or glucose. These same compositions are contemplated that contain a 5'-primaryamino-substituted psoralen rather than a 4'-primaryamino-substituted psoralen.

A novel synthetic platelet storage media, is also contemplated, comprising an aqueous solution of:

45–100 mM sodium chloride;
4–5 mM potassium chloride;
10–15 mM sodium citrate;
20–27 mM sodium acetate;
0–2 mM glucose;
0–30 mM mannitol;
approximately 20 mM sodium phosphate;
2–3 mM magnesium chloride; and
a psoralen selected from the group consisting of 4'-primaryaminopsoralen and a 5'-primaryaminopsoralen, at a concentration between approximately 0.1 and 250 µM.

DESCRIPTION OF THE DRAWINGS

FIG. 5E is a diagram of a synthesis pathway and the chemical structure of compound 3 of the present invention.

DESCRIPTION OF THE INVENTION

Figure 1:
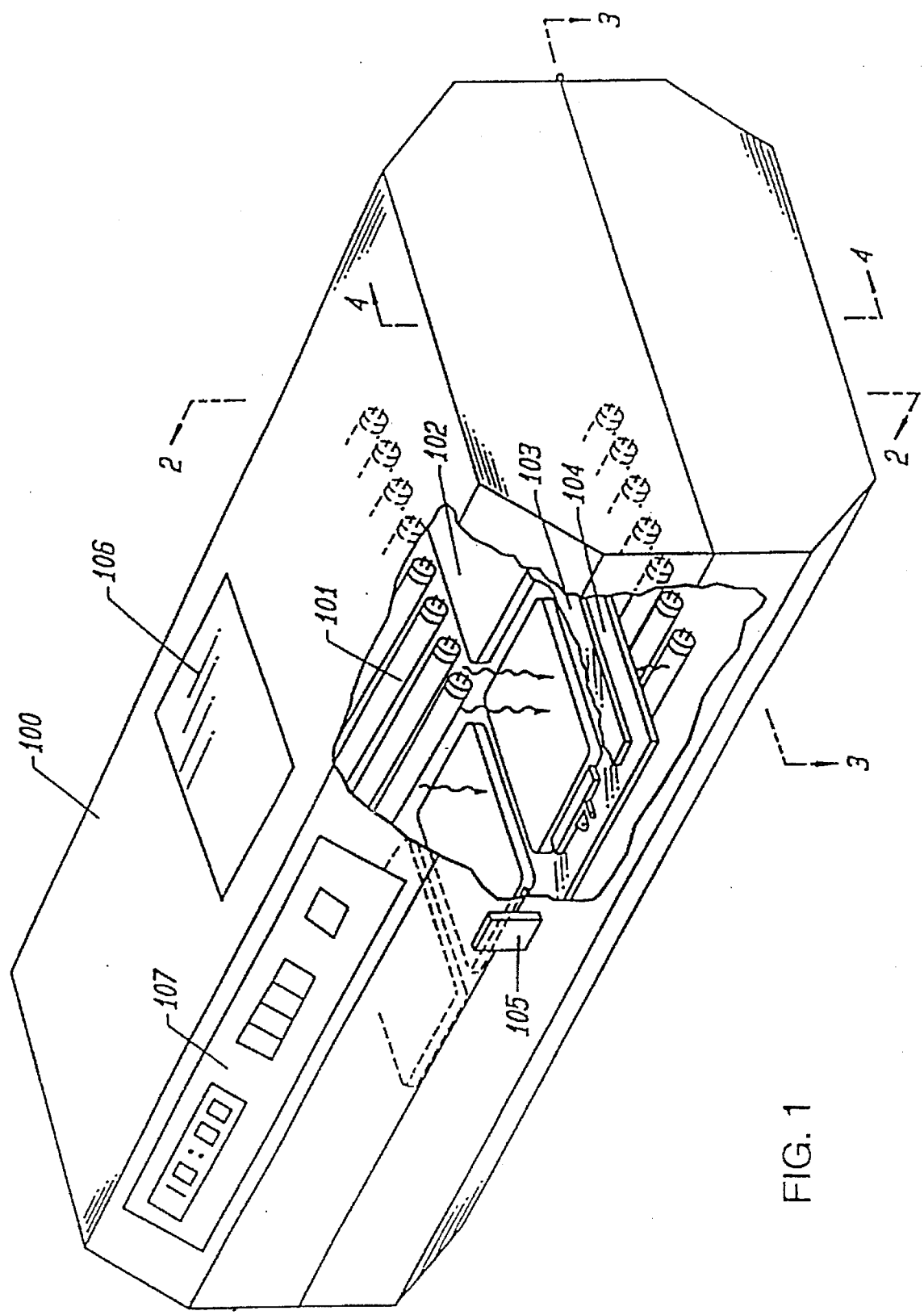
FIG. 1 is a perspective view of one embodiment of the device of the present invention.
Figure 2:
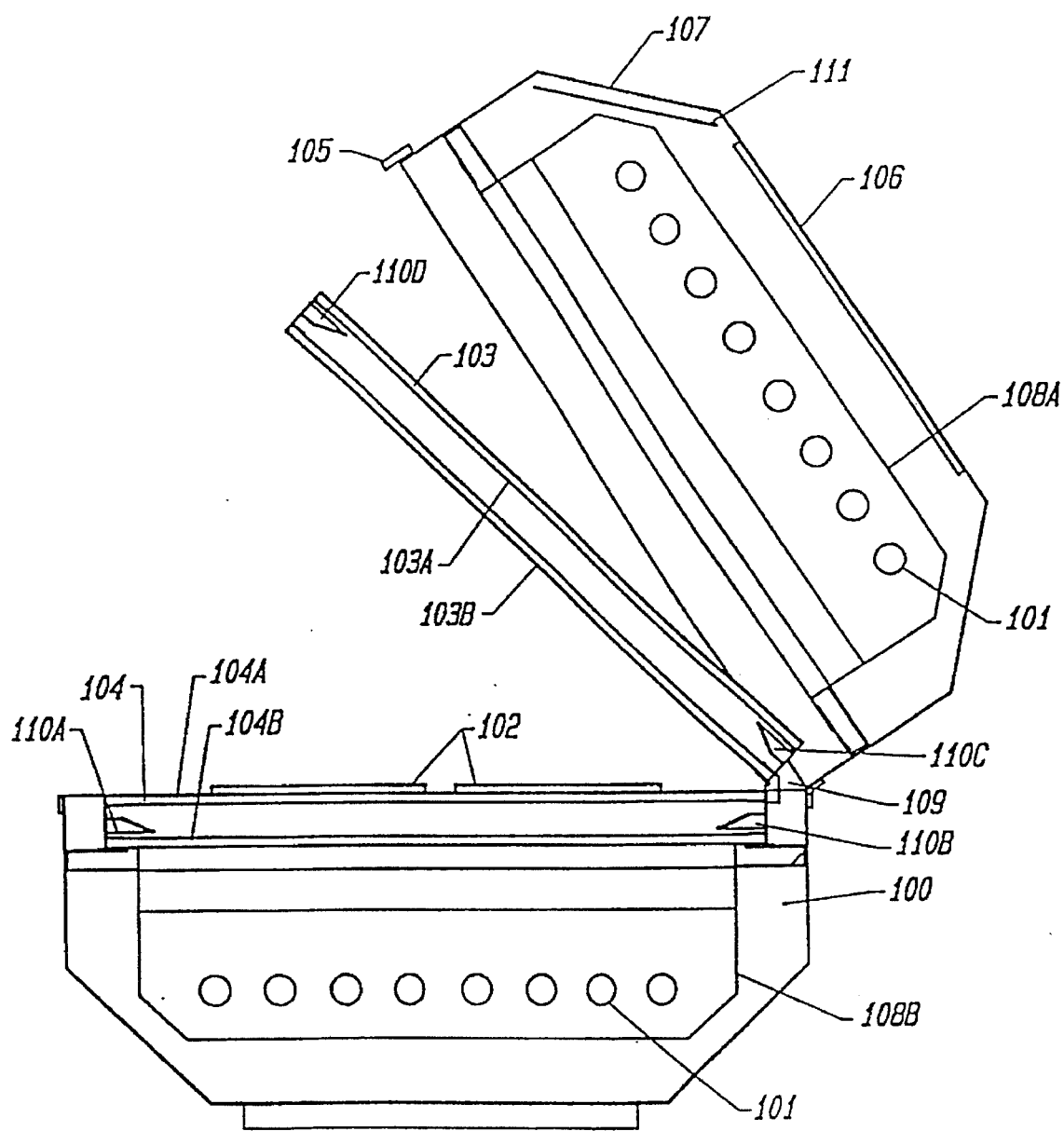
FIG. 2 is a cross-sectional view of the device shown in FIG. 1 along the lines of 2—2.
Figure 3:
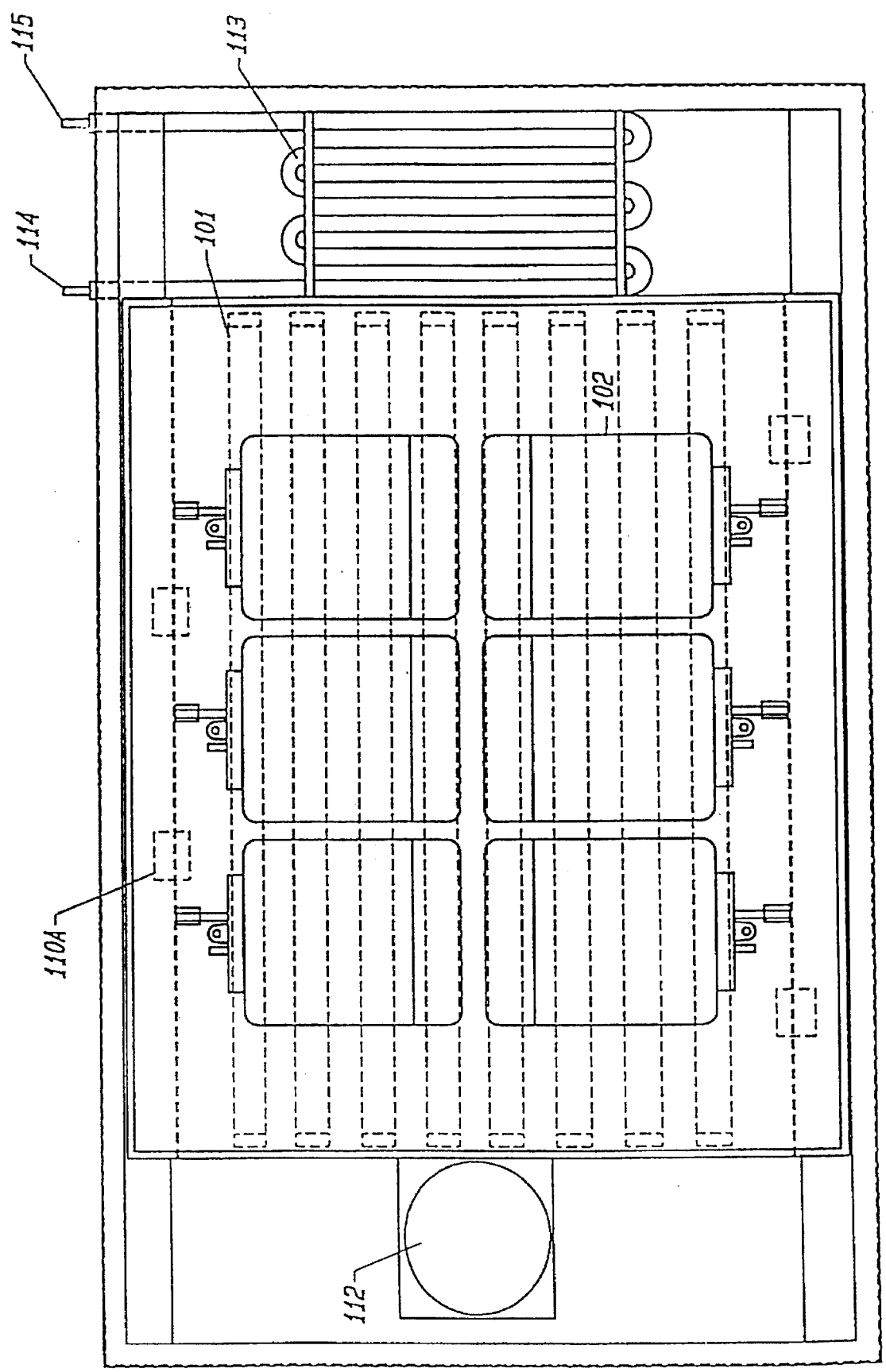
FIG. 3 is a cross-sectional view of the device shown in FIG. 1 along the lines of 3—3.
Figure 4:
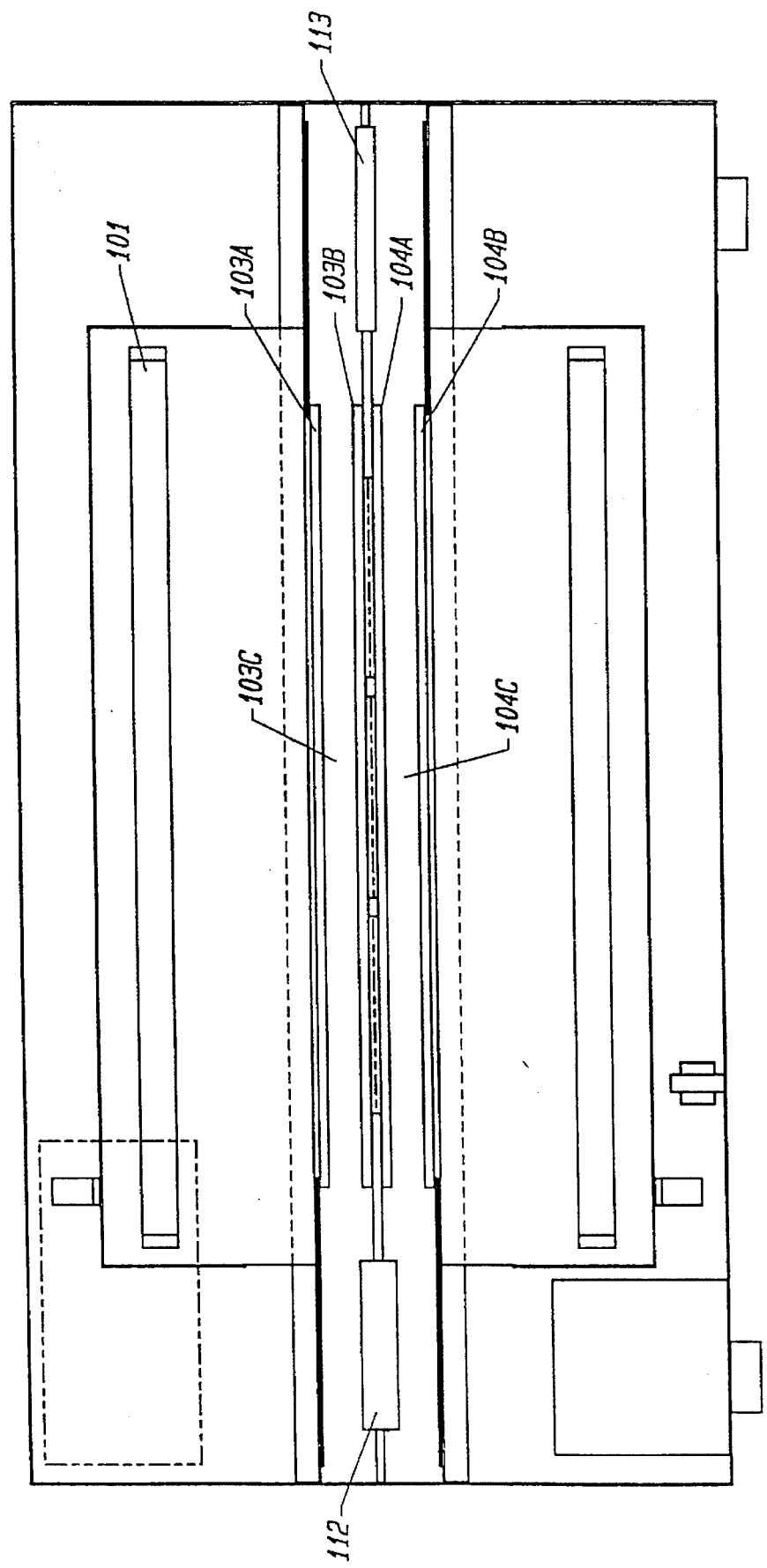
FIG. 4 is a cross-sectional view of the device shown in FIG. 1 along the lines of 4—4.
Figure 5A:
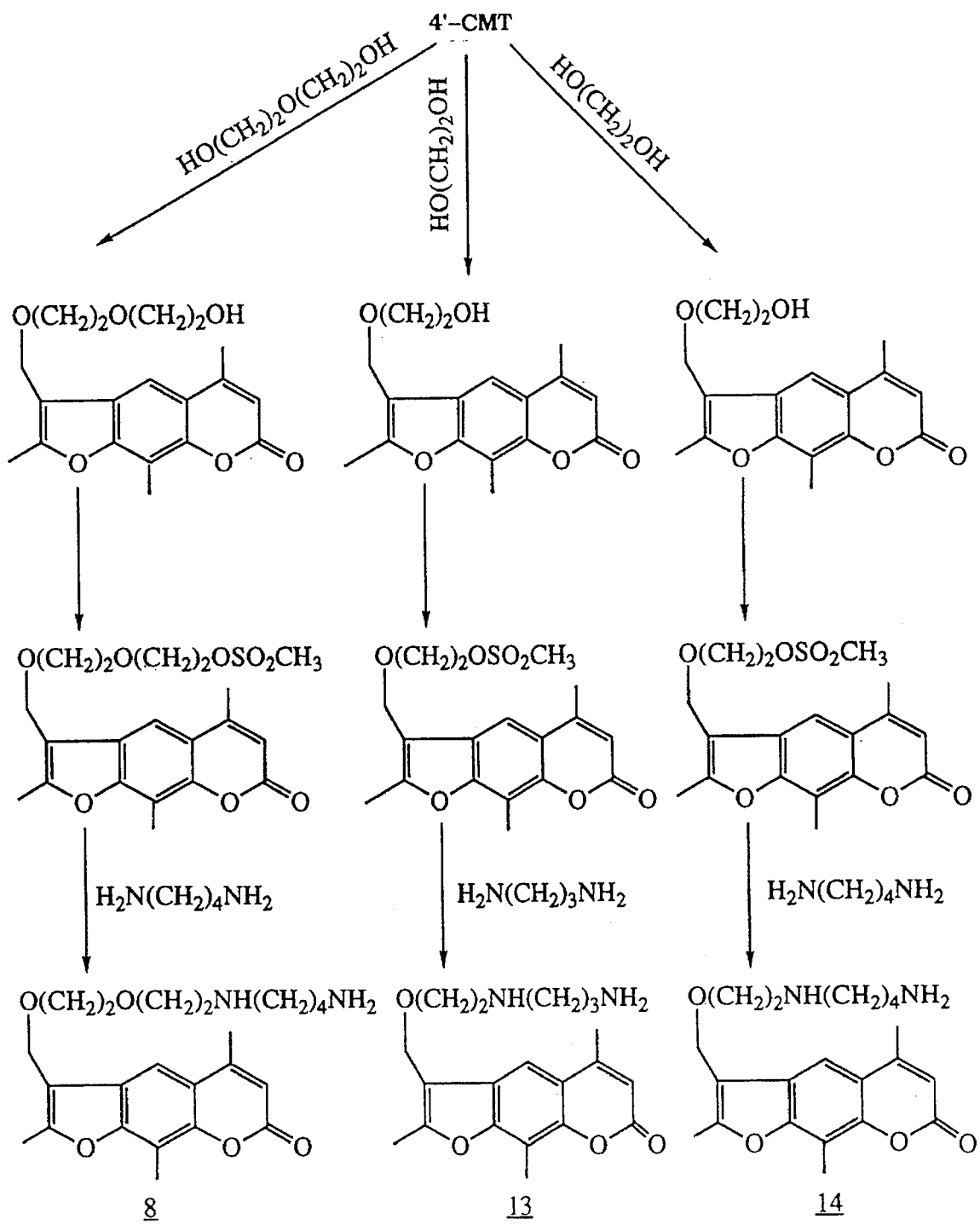
FIG. 5A is a diagram of synthesis pathways and chemical structures of compounds 8, 13, and 14 of the present invention.
Figure 5B:
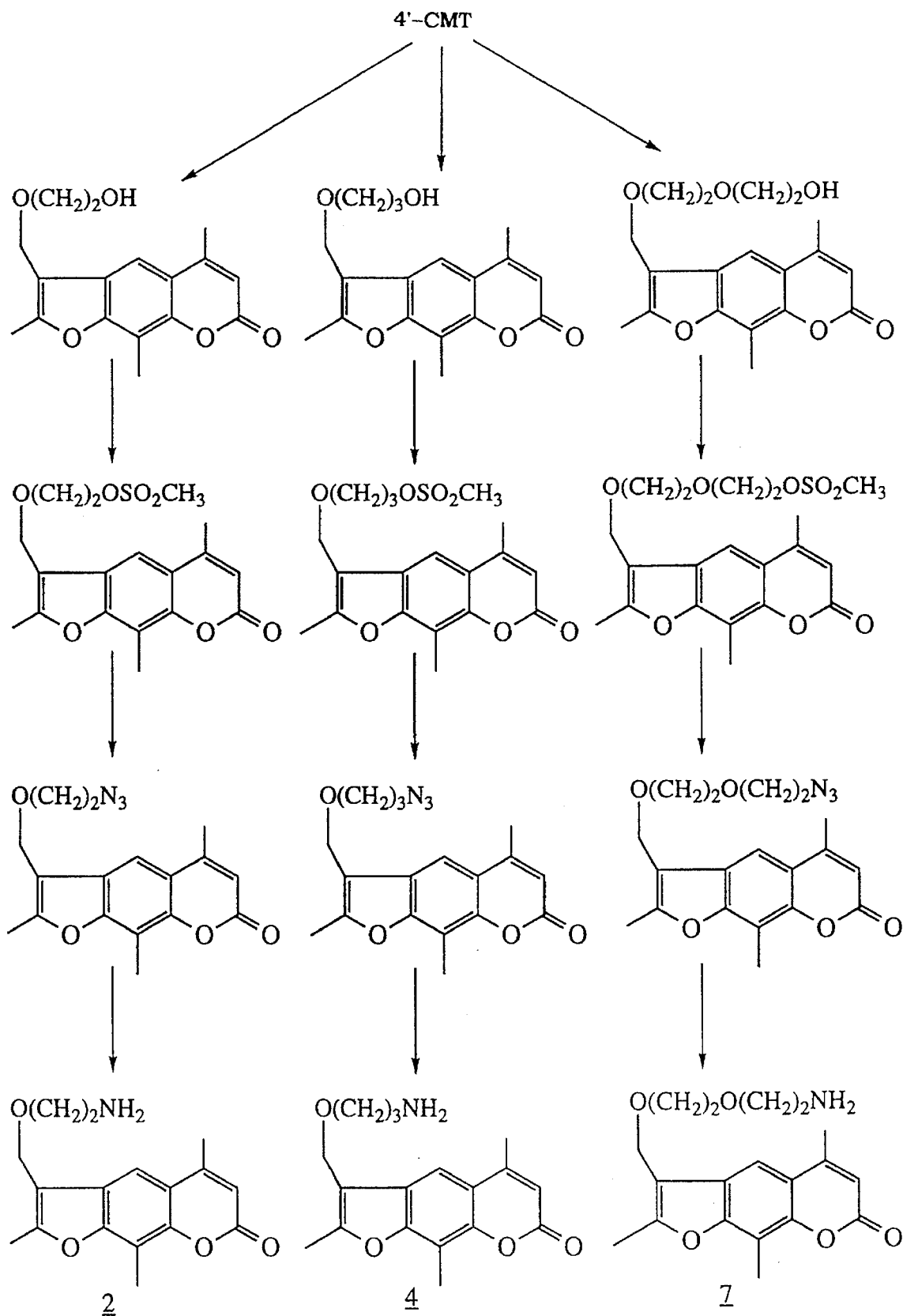
FIG. 5B is a diagram of synthesis pathways and chemical structures of compounds 2, 4, and 7 of the present invention.
Figure 5C:
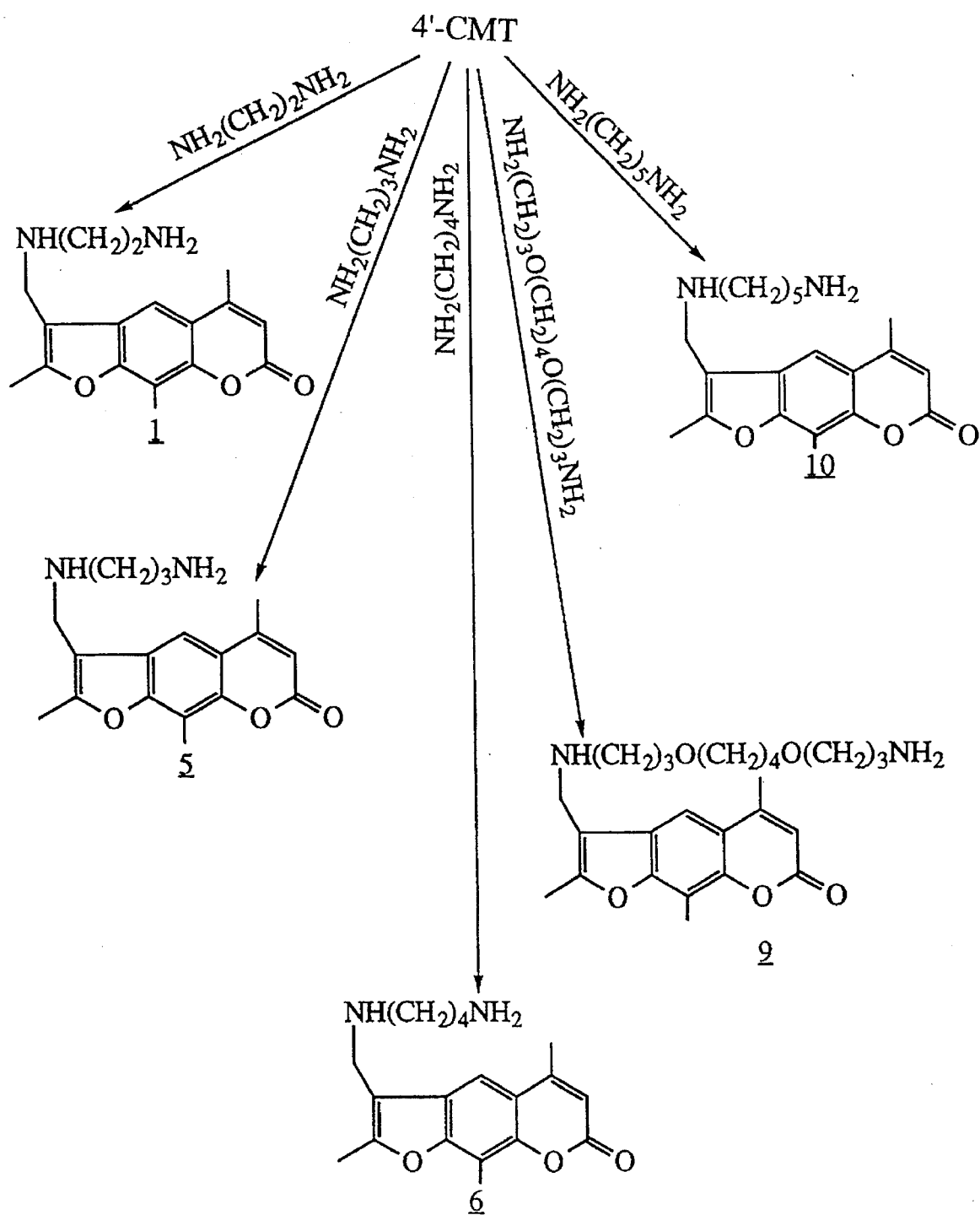
FIG. 5C is a diagram of synthesis pathways and chemical structures of compounds 1, 5, 6, 9, and 10 of the present invention.
Figure 5D:
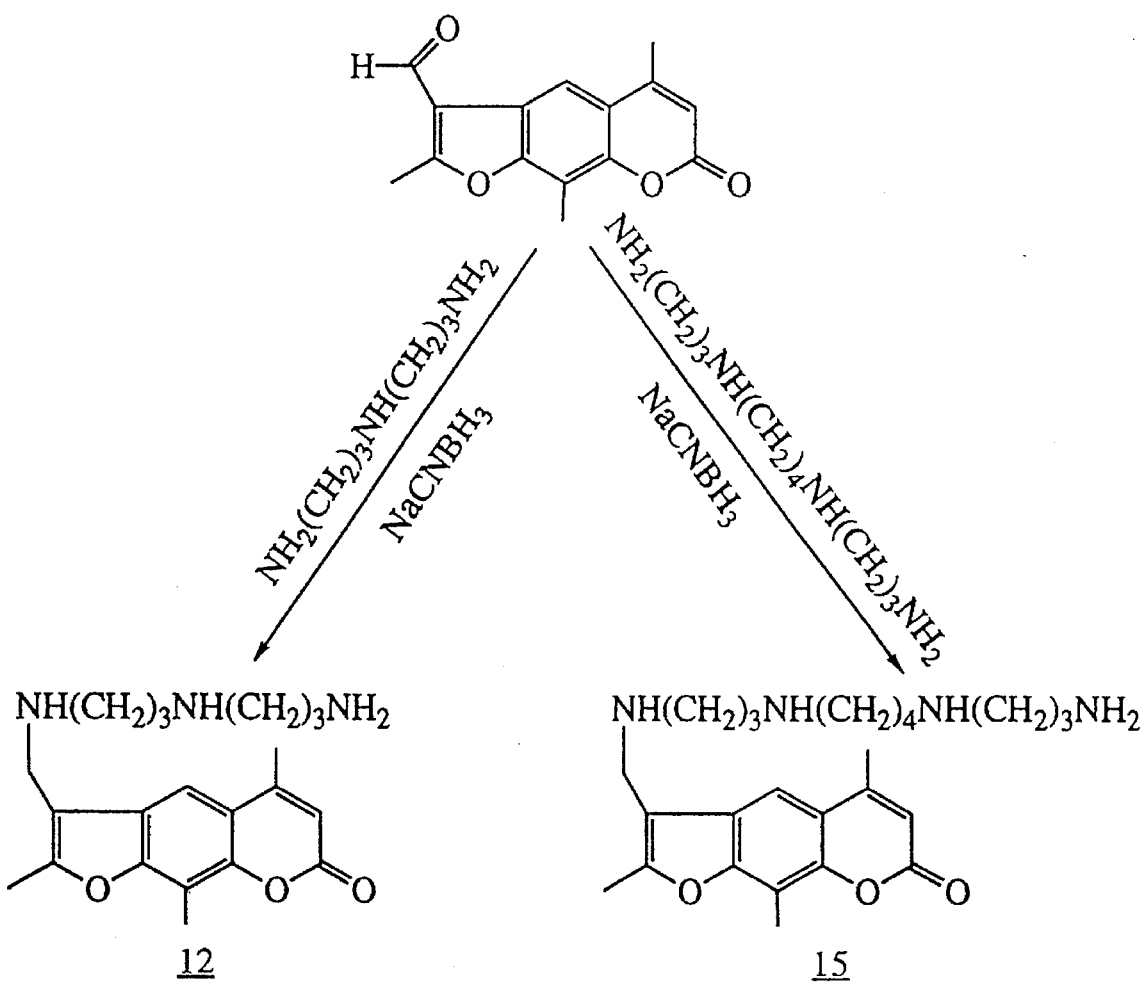
FIG. 5D is a diagram of synthesis pathways and chemical structures of compounds 12 and 15 of the present invention.
Figure 5F:
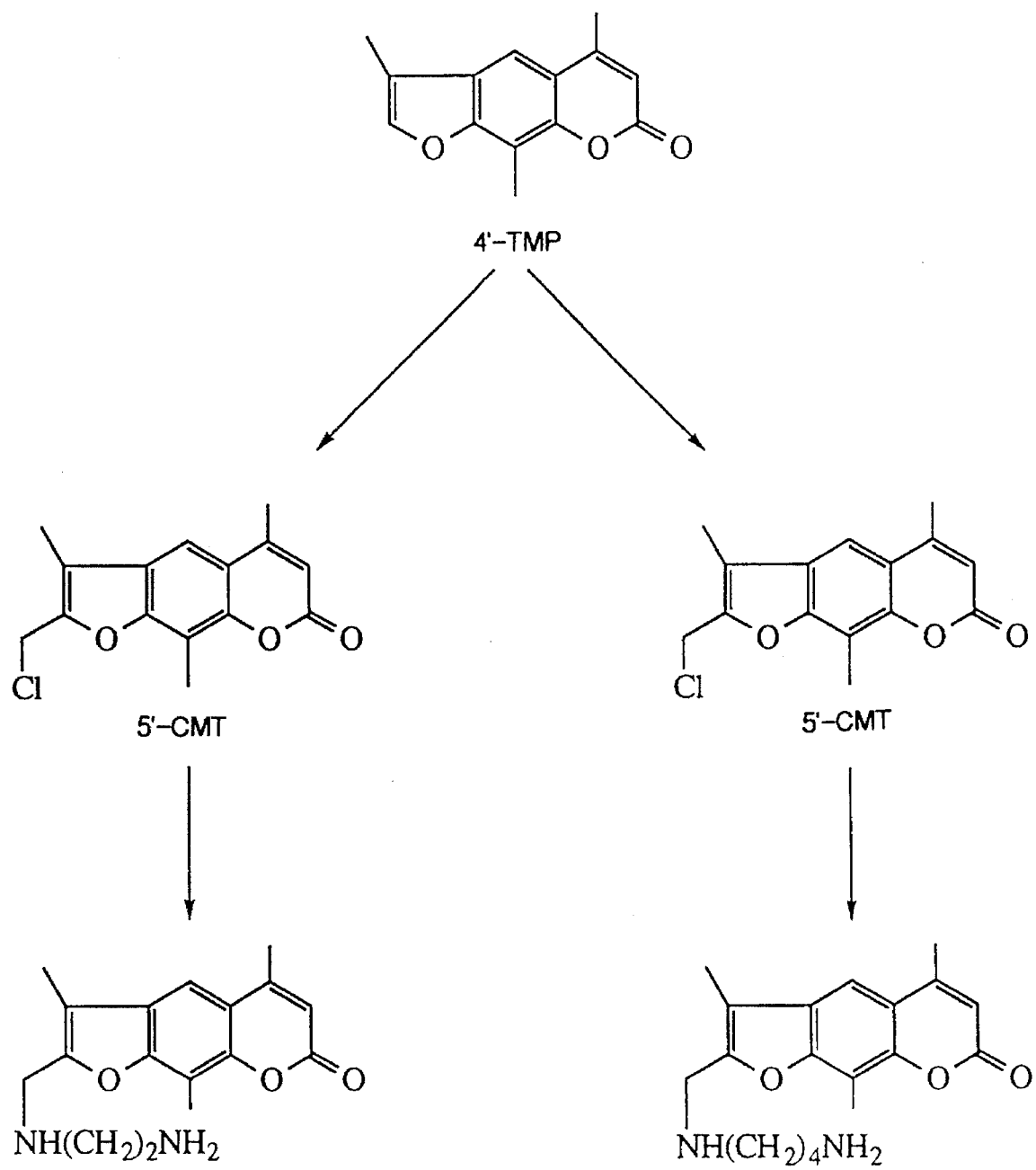
FIG. 5F is a diagram of synthesis pathways and the chemical structure of compounds 16 and 17 of the present invention.

The present invention provides new psoralens and methods of synthesis of new psoralens having enhanced ability to inactivate pathogens in the presence of ultraviolet light. The new psoralens are effective against a wide variety of pathogens. The present invention also provides methods of using new and known compounds to inactivate pathogens in health related products to be used in vivo and in vitro, and in particular, blood products, without significantly effecting blood product function or exhibiting mutagenicity.

The inactivation methods of the present invention provide methods of inactivating pathogens, and in particular, viruses, in blood products prior to use in vitro or in vivo. In contrast with previous approaches, the method requires only short irradiation times and there is no need to limit the concentration of molecular oxygen.

The description of the invention is divided into the following sections: I) Photoactivation Devices, II) Compound Synthesis, III) Binding of Compounds to Nucleic Acid, IV) Inactivation of Contaminants, and V) Preservation of Biochemical Properties of Material Treated.

I. PHOTOACTIVATION DEVICES

The present invention contemplates devices and methods for photoactivation and specifically, for photoactivation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause photoactivation of at least one photoreactive compound; b) means for supporting a plurality of samples in a fixed relationship with the radiation providing means during photoactivation; and c) means for maintaining the temperature of the samples within a desired temperature range during photoactivation. The present invention also contemplates methods, comprising: a) supporting a plurality of sample containers, containing one or more photoreactive compounds, in a fixed relationship with a fluorescent source of electromagnetic radiation; b) irradiating the plurality of sample containers simultaneously with electromagnetic radiation to cause photoactivation of at least one photoreactive compound; and c) maintaining the temperature of the sample within a desired temperature range during photoactivation.

The major features of one embodiment of the device of the present invention involve: A) an inexpensive source of ultraviolet radiation in a fixed relationship with the means for supporting the sample containers, B) rapid photoactivation, C) large sample processing, D) temperature control of the irradiated samples, and E) inherent safety.

A. Electromagnetic Radiation Source

Many sources of ultraviolet radiation can be successfully used in decontamination protocols with psoralens. For example, some groups have irradiated sample from above and below by General Electric type F20T12-BLB fluorescent UVA bulbs with an electric fan blowing gently across the lights to cool the area. Alter, H. J., et al., The Lancet, 24:1446 (1988). Another group used Type A405-TLGW/05 long wavelength ultraviolet lamp manufactured by P. W. Allen Co., London placed above the virus samples in direct contact with the covers of petri dishes containing the samples, and was run at room temperature. The total intensity delivered to the samples under these conditions was $1.3 \times 10^{15}$ photons/second $cm^2$ (or 0.7 $mW/cm^2$ or 0.0007 $J/cm^2$ sec) in the petri dish. Hearst, J. E., and Thiry, L., Nucleic Acids Research, 4:1339 (1977). However, without intending to be limited to any type of photoactivation device, the present invention contemplates several preferred arrangements for the photoactivation device, as follows.

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is herein described in terms of nanometers "nm"; $10^{-9}$ meters). For purposes herein, ultraviolet radiation extends from approximately 180 nm to 400 nm. When a radiation source, by virtue of filters or other means, does not allow radiation below a particular wavelength (e.g. 320 nm), it is said to have a low end "cutoff" at that wavelength (e.g. "a wavelength cutoff at 300 nanometers"). Similarly, when a radiation source allows only radiation below a particular wavelength (e.g. 360 nm), it is said to have a high end "cutoff" at that wavelength (e.g. "a wavelength cutoff at 360 nanometers").

For any photochemical reaction it is desired to eliminate or least minimize any deleterious side reactions. Some of these side reactions can be caused by the excitation of endogenous chromophores that may be present during the photoactivation procedure. In a system where only nucleic acid and psoralen are present, the endogenous chromophores are the nucleic acid bases themselves. Restricting the photoactivation process to wavelengths greater than 320 nm minimizes direct nucleic acid damage since there is very little absorption by nucleic acids above 313 nm.

In human serum or plasma, for example, the nucleic acid is typically present together with additional biological constituents. If the biological fluid is just protein, the 320 nm cutoff will be adequate for minimizing side reactions (aromatic amino acids do not absorb above 320 nm). If the biological fluid includes other analytes, there may be constituents that are sensitive to particular wavelengths of light. In view of the presence of these endogenous constituents, it is intended that the device of the present invention be designed to allow for irradiation within a small range of specific and desirable wavelengths, and thus avoid damage blood components. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmits only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiation, it is expressed in terms of intensity flux (milliwatts per square centimeter or "mW cm-2" or $J/cm^2 sec$). "Output" is herein defined to encompass both the emission of radiation (yes or no; on or off) as well as the level of irradiation. In a preferred embodiment, intensity is monitored at 4 locations: 2 for each side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for approximately fifteen minutes of irradiation time, so that, when measured for the wavelengths between 320 and 350 nanometers, an intensity flux greater than approximately 1 mW cm-2 (0.001 $J/cm^2$ sec.) is provided to the sample vessels.

C. Processing of Large Numbers of Samples

As noted, another important feature of the photoactivation devices of the present invention is that they provide for the processing of large numbers of samples. In this regard, one element of the devices of the present invention is a means for supporting a plurality of blood bags. In the preferred embodiment of the present invention the supporting means comprises a blood bag support placed between two banks of lights. By accepting commonly used commercially available bags, the device of the present invention allows for convenient processing of large numbers of samples.

D. Temperature Control

As noted, one of the important features of the photoactivation devices of the present invention is temperature control. Temperature control is important because the temperature of the sample in the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e. an opaque housing). No irradiation is allowed to pass to the user. This allows for inherent safety for the user.

II. COMPOUND SYNTHESIS

A. Photoactivation Compounds in General

"Photoactivation compounds" (or "photoreactive compounds") defines a family of compounds that undergo chemical change in response to electromagnetic radiation. Table 1 is a partial list of photoactivation compounds.

TABLE 1

Photoactivation Compounds

Actinomycins
Anthracyclinones
Anthramycin
Benzodipyrones
Fluorenes and fluorenones
Furocoumarins
Mitomycin
Monosteal Fast Blue
Norphillin A
Many organic dyes not specifically listed
Phenanthridines
Phenazathionium Salts
Phenazines
Phenothiazines
Phenylazides
Quinolines
Thiaxanthenones The preferred species of photoreactive compounds described herein is commonly referred to as the furocoumarins. In particular, the present invention contemplates those compounds described as psoralens: [7H-furo(3,2-g)-(1)-benzopyran- 7-one, or β-lactone of 6-hydroxy-5-benzofuranacrylic acid], which are linear:

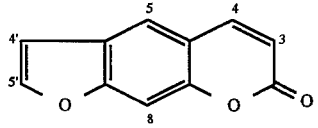

and in which the two oxygen residues appended to the central aromatic moiety have a 1, 3 orientation, and further in which the furan ring moiety is linked to the 6 position of the two ring coumarin system. Psoralen derivatives are derived from substitution of the linear furocoumarin at the 3, 4, 5, 8, 4', or 5' positions.

8-Methoxypsoralen (known in the literature under various named, e.g., xanthotoxin, methoxsalen, 8-MOP) is a naturally occurring psoralen with relatively low photoactivated binding to nucleic acids and low mutagenicity in the Ames assay, which is described in the following experimental section. 4'-Aminomethyl-4,5',8-trimethylpsoralen (AMT) is one of most reactive nucleic acid binding psoralen derivatives, providing up to 1 AMT adduct per 3.5 DNA base pairs. S. T. Isaacs, G. Wiesehahn and L. M. Hallick, NCI Monograph 66:21 (1984). However, AMT also exhibits significant levels of mutagenicity. A new group of psoralens was desired which would have the best characteristics of both 8-MOP and AMT: low mutagenicity and high nucleic acid binding affinity, to ensure safe and thorough inactivation of pathogens. The compounds of the present invention were designed to be such compounds.

"4'-primaryamino-substituted psoralens" are defined as psoralen compounds which have an $NH_2$ group linked to the 4'-position of the psoralen by a hydrocarbon chain having a total length of 2 to 20 carbons, where 0 to 6 of those carbons are independently replaced by NH or O, and each point of replacement is separated from each other point of replacement by at least two carbons, and is separated from the psoralen by at least one carbon. 4'-primaryamino-substituted psoralens may have additional substitutions on the 4, 5', and 8 positions of the psoralen, said substitutions include, but are not limited to, the following groups: H and $(CH_2)_nCH_3$, where n=0-6.

"5'-primaryamino-substituted psoralens" are defined as psoralen compounds which have an $NH_2$ group linked to the 5'-position of the psoralen by a hydrocarbon chain having a total length of 1 to 20 carbons, where 0 to 6 of those carbons are independently replaced by NH or O, and each point of replacement is separated from each other point of replacement by at least two carbons, and is separated from the psoralen by at least one carbon. 5'-primaryamino-substituted psoralens may have additional substitutions on the 4, 4', and 8 positions of the psoralen, said substitutions include, but are not limited to, the following groups: H and $(CH_2)_nCH_3$, where n=0-6.

B. Synthesis of the Psoralens

The present invention contemplates synthesis methods for the novel compounds of the present invention, as well as new synthesis methods for known intermediates. Specifically, the novel compounds are mono, di or trialkylated 4'- or 5'-primaryamino-substituted psoralens. Several examples of the schemes discussed in this section are shown in FIGS. 5A–5F. For ease of reference, TABLE 2 sets forth the nomenclature used for the psoralen derivatives discussed herein. The structures of compounds 1–18 are also pictured in FIGS. 5A–5F. Note that this section (entitled "B. Synthesis of the Psoralens") the roman numerals used to identify compounds correlate with Schematics 1–6 only, and do not correlate with the compound numbers listed in Table 2 or FIGS. 5A–5F.

It is most logical to first describe the synthesis of intermediates useful in synthesizing many of the compounds of the present invention. While the invention is not limited to 4,5',8-trimethyl-4'- primaryamino-substituted psoralens or 4,4',8-trimethyl-5'-primaryamino-substituted psoralens, some important intermediates include tri- and tetramethyl psoralens, 4'-halomethyl-4,5',8-trimethylpsoralens and 5'-halomethyl-4,4',8-trimethylpsoralens. The preparation of these critical intermediates presents difficult challenges.

TABLE 2

| # | COMPOUND |
|---|----------|
| 1 | 4'-(4-amino-2-aza)butyl-4,5',8-trimethylpsoralen |
| 2 | 4'-(4-amino-2-oxa)butyl4,5',8-trimethylpsoralen |
| 3 | 4'-(2-aminoethyl)-4,5',8-trimethylpsoralen |
| 4 | 4'-(5-amino-2-oxa)pentyl-4,5',8-trimethylpsoralen |
| 5 | 4'-(5-amino-2-aza)pentyl-4,5',8-trimethylpsoralen |
| 6 | 4'-(6-amino-2-aza)hexyl-4,5',8-trimethylpsoralen |
| 7 | 4'-(7-amino-2,5-oxa)heptyl-4,5',8-trimethylpsoralen |
| 8 | 4'-(12-amino-8-aza-2,5-dioxa)dodecyl-4,5',8-trimethylpsoralen |
| 9 | 4'-(13-amino-2-aza-6,11-'dioxa)tridecyl-4,5',8-trimethylpsoralen |
| 10 | 4'-(7-amino-2-aza)heptyl-4,5',8-trimethylpsoralen |
| 11 | 4'-(7-amino-2-aza-5-oxa)heptyl-4,5',8-trimethylpsoralen |
| 12 | 4'-(9-amino-2,6-diaza)nonyl-4,5',8-trimethylpsoralen |
| 13 | 4'-(8-amino-5-aza-2-oxa)octyl-4,5',8-trimethylpsoralen |
| 14 | 4'-(9-amino-5-aza-2-oxa)nonyl-4,5',8-trimethylpsoralen |
| 15 | 4'-(14-amino-2,6,11-triaza)tetradecyl-4,5',8-trimethylpsoralen |

TABLE 2-continued

| # | COMPOUND |
|---|---|
| 16 | 5'-(4-amino-2-aza)butyl-4,4',8-trimethylpsoralen |
| 17 | 5'-(6-amino-2-aza)hexyl-4,4',8-trimethylpsoralen |
| 18 | 5'-(4-amino-2-oxa)butyl-4,4',8-trimethylpsoralen |

Synthesis of Intermediates

Previous syntheses of 4'-chloromethyl-4,5',8-trimethylpsoralen (4'-CMT) and 4'-bromomethyl-4,5',8-trimethylpsoralen (4'-BrMT) start from 4,5',8-trimethylpsoralen (5'-TMP) which is commercially available (Aldrich Chemical Co., Milwaukee, Wis.) or can be prepared in four steps as described below for other alkylated psoralens. 5'-TMP is converted to 4'-CMT using a large excess (20-50 equivalents) of highly carcinogenic, and volatile chloromethyl methyl ether. Halomethylation of the 4,5',8-trialkylpsoralens with chloromethyl methyl ether or bromomethyl methyl ether is described in U.S. Pat. No. 4,124,598, to Hearst. The bromo compound, 4'-BrMT, is likewise prepared using bromomethyl methyl ether which is somewhat less volatile. Yields of only 30%-60% of the desired intermediate are obtained. The 5'-chloromethyl-4,4',8-trimethylpsoralen (5'-CMT) and 5'-bromomethyl-4,4',8-trimethylpsoralen (5'-BrMT) are prepared similarly, using the isomeric starting compound, 4,4',8-trimethylpsoralen (4'-TMP) [U.S. Pat. No. 4,294,822, to Kaufman; McLeod, et al., "Synthesis of Benzofuranoid Systems. I. Furocoumarins, Benzofurans and Dibenzofurans," Tetrahedron Letters 237 (1972)].

Described herein is a much improved procedure which allows for the synthesis of either isomer of the bromomethyl-trialkylpsoralens from the same psoralen precursor by careful control of reaction conditions. See Schematic 1.

provide 4,8-dialkyl-4',5'-dimethylpsoralen (II). Treatment of the tetrasubstituted psoralen and N-bromosuccinimide in a solvent at room temperature up to 150° C. leads to bromination at the 4'- or 5'- position, depending upon the conditions used. A catalyst such as dibenzoyl peroxide may be added, but is not necessary. If the solvent used is carbon tetrachloride at reflux, 4,8-dialkyl-5'-bromomethyl-4'-methylpsoralen (IV) is obtained in yields of 50% or greater. If methylene chloride is used at room temperature, only 4,8-dialkyl-4'-bromomethyl-5'-methylpsoralen (III) is obtained in ≧80% yield. Benzylic bromination in other solvents can also be done, generating one of the isomeric products alone or in a mixture. These solvents include, but are not limited to 1,2-dichloroethane, chloroform, bromotrichloromethane and benzene.

General Scheme of Synthesis of 4'-Substituted Psoralens

Turning now to the synthesis of a subclass of the linear psoralens, 4,5',8-trialkylpsoralens can be made as follows. The 4,8-dialkylcoumarins are prepared from 2-alkylresorcinols and a 3-oxoalkanoate ester by the Pechmann reaction (Organic Reactions Vol VII, Chap 1, ed. Adams et al, Wiley, N.Y., (1953)). The hydroxy group is treated with an allylating reagent, $CH_2=CHX—CH(R)—Y$, where X is a halide or hydrogen, Y is a halide or sulfonate, and R is H or $(CH_2)_vCH_3$, where v is a whole number from 0 to 4. Claisen rearrangement of the resultant allyl ether gives 4,8-dialkyl-6-allyl-7-hydroxycoumarin. The coumarins are converted to the 4,5',8-trialkylpsoralens using procedures similar to one of several previously described procedures (i.e., see, Bender et al, J. Org. Chem. 44:2176 (1979); Kaufman, U.S. Pat. Nos. 4,235,781 and 4,216,154, hereby incorporated by reference). 4,5',8-Trimethylpsoralen is a natural product and is commercially available (Aldrich Chemical Co., Milwaukee, Wis.).

General Scheme of Synthesis of 5'-Substituted Psoralens

SCHEMATIC 1

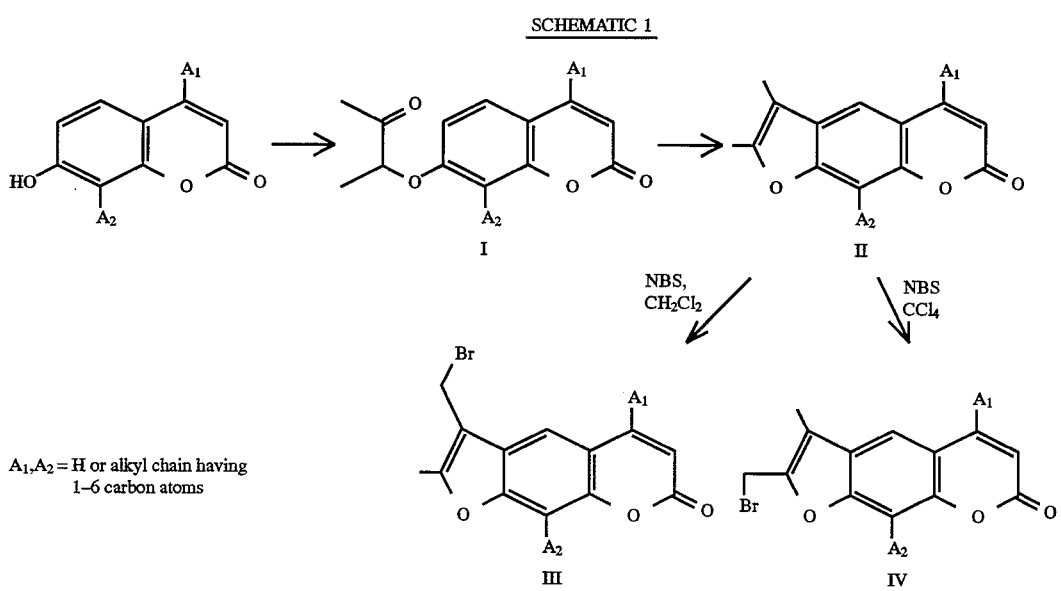

A₁,A₂ = H or alkyl chain having 1–6 carbon atoms

Reaction of the 4,8-dialkyl-7-hydroxycoumarin with 2-chloro-3-butanone under typical basic conditions, provides 4,8-dialkyl-7-(1-methyl-2-oxo)propyloxycoumarin (I). This material is cyclized by heating in aqueous NaOH to The 4,4',8-trialkylpsoralens can be prepared in two steps also starting from the 4,8-dialkyl-7-hydroxycoumarins discussed above. The coumarin is treated with an alpha-chloro ketone under basic conditions to give the 4,8-dialkyl-7-(2- oxoalkoxy)coumarin. Cyclization of this intermadiate to the 4,4',8-trialkylcoumarin occurs by heating in aqueous base.

Longer chain 4'-(ω-haloalkyl)trialkylpsoralens (herein referred to as longer chain 4'-HATP) where the alkyl groups are selected from the group $(CH_2)_2$ to $(CH_2)_{10}$ can be prepared under Freidel-Crafts conditions as discussed elsewhere (Olah and Kuhn, J. Org. Chem., 1964, 29, 2317; Friedel-Crafts and Related Reactions, Vol. II, Part 2, Olah, ed., Interscience, NY, 1964, p 749). While reactions of the halomethyl- intermediates with amines (e.g., Hearst et al., U.S. Pat. No. 4,124,598), and alcohols (e.g., Kaufman, U.S. Pat. No. 4,269,852) have been described, there are only two original reports on the formation of extended chain primary amines. They describe the reaction of the 4'-chloromethyl-4,5',8-trimethyl psoralen with $H_2N$—$(CH_2)_n$—$NH_2$ (where n=2, 4, 6) (Lee, B., et al. "Interaction of Psoralen-Derivatized Oligodeoxyribonucleoside Methylphosphonates with Single-Stranded DNA," Biochemistry 27:3197 (1988), and with $H_2NCH_2CH_2SSCH_2CH_2NH_2$ (Goldenberg, M., et al., "Synthesis and Properties of Novel Psoralen Derivatives," Biochemistry 27:6971 (1988)). The utility of the resulting compounds for nucleic acid photoreaction has not previously been reported. The properties of these materials, such as decreased mutagenicity, are unexpected based on what is known about previously prepared compounds, such as AMT.

Several synthesis routes are shown in Schematic 2, below. Starting from the 4'-HATP, reaction with an excess of a bis-hydroxy compound, HO—(B)—OH, where B is either an alkyl chain (e.g., HO—(B)—OH is 1,3-propanediol) or a monoether (e.g., diethylene glycol) or a polyether (e.g., tetraethylene glycol), either neat or with a solvent such as acetone at 20°–80° C., and a base for the carbon chains longer than halomethyl, gives a (ω-hydroxyalkoxy)alkyl psoralen.

VI). This can subsequently be converted to the azide in refluxing ethanol and the azide reduced to the final amine, structure VII (examples are Compounds 2, 4 and 7). The method described herein utilizes triphenylphosphine and water in THF for the reduction but other methods are contemplated. A preferred method of preparation of structure VII uses the reaction of 4'-HATP with a primary linear alcohol containing a protected amine (e.g., a phthalimido group) at the terminal position in a suitable solvent such as DMF at 25°–150° C. to give I. The amine is then deprotected under standard conditions (e.g. hydrazine or aqueous $MeNH_2$ to deprotect a phthalimido group [higher alkyl hydrazines, such as benzyl hydrazines, are also contemplated]) to give VII. Conversely, structure VI can be reacted with diamines, $H_2N$-(B')-$NH_2$ (Structure IX), where B' is an alkyl chain (e.g., 1,4,-butanediamine), a monoether (e.g., 3-oxa-1,5-pentanediamine) or a polyether (e.g., 3,6-dioxa-1,8-octanediamine) to give the final product, compound VIII (examples are Compounds 8, 13 and 14.) This reaction is carried out with an excess of diamine in acetonitrile at reflux, but other solvents and temperatures are equally possible.

Some final compounds are desired in which the carbon chain is linked to the 4'- position of the psoralen ring by an aminoalkyl group $[NH(CH_2)_w]$ rather than by an oxyalkyl group $[O(CH_2)_w]$. Synthesis pathways for these compounds are shown in Schematic 3, below. When the linkage between this nitrogen and the terminating nitrogen contains only $CH_2$ subunits and oxygen but no other nitrogens (structure X) (examples are Compounds 1, 5, 6, 9, 10 and 11), the product can conveniently be prepared from the 4'-HATP and the appropriate diamine of structure IX. This method is also applicable to final products that contain more than two nitrogens in the chain (structure XIII) (examples are Compounds 12 and 15) starting from polyamines of structure XII (e.g., norspermidine or spermine [commercially available

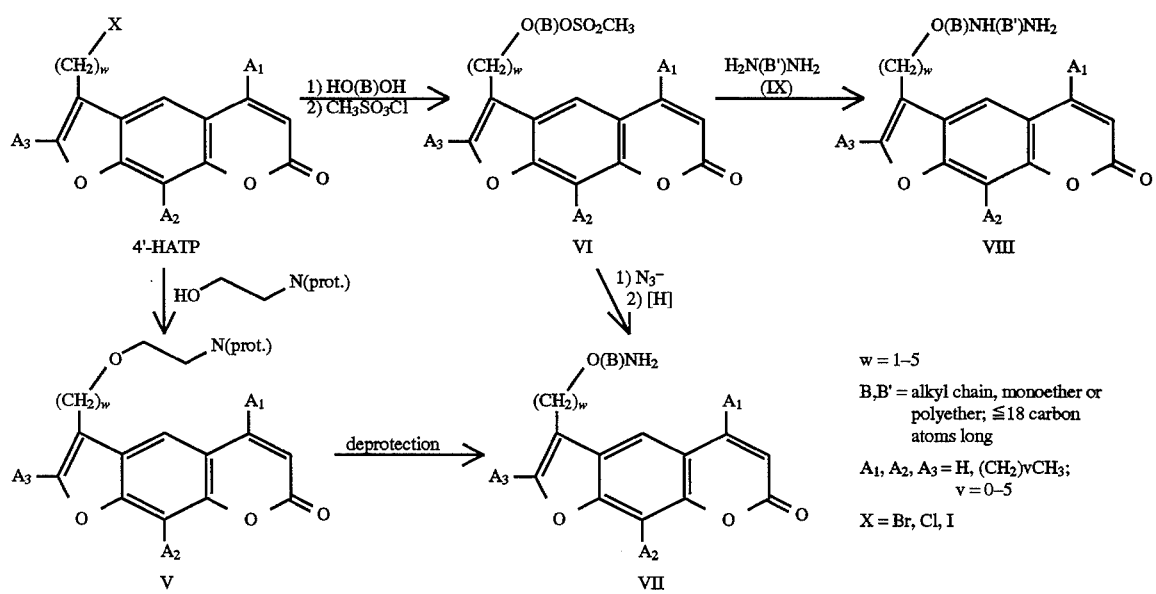

SCHEMATIC 2 w = 1–5

B,B' = alkyl chain, monoether or polyether; ≦18 carbon atoms long $A_1, A_2, A_3 = H, (CH_2)vCH_3$;
    v = 0–5

X = Br, Cl, I

The terminal hydroxy group can be transformed to an amino group under a variety of conditions (for example see Larock, "Comprehensive Organic Transformations", VCH Publishers, NY, 1989). Particularly, the hydroxy group can be converted to the ester of methanesulfonic acid (structure from Aldrich, Milwaukee, Wis.]), however, in this case isomeric structures are also formed in considerable amounts. The preferred method for the preparation of structure XIII is reductive amination of the psoralen-4'-alkanal (XI) with a polyamine of structure XII and a reducing agent such as sodium cyanoborohydride. This reductive amination is applicable to the synthesis of compounds X as well. The carboxaldehydes (structure XI, w=0) have been prepared previously by hydrolysis of the 4'-halomethyl compounds and subsequent oxidation of the resultant 4'-hydroxymethyl compound. (Isaacs et al, J. Labelled Cmpds. Radiopharm., 1982, 19, 345). These compounds can also be conveniently prepared by formylation of the 4'-hydrido compounds with a formamide and $POCl_3$, or with hexamethylene tetraamine in acid. Longer chain alkanals can be prepared from the 4'-HATP compounds by conversion of the terminal halo group to an aldehyde functionality (for example, Durst, Adv. Org. Chem. 6:285 (1969)).

these compounds (structures XIV) (an example is Compound 3) are prepared either by reaction of the 4'-HATP with potassium phthalimide or azide and subsequent liberation of the desired amine as before, or conversion of the 4'-HATP to the cyanide compound, followed by reduction, for example with $NaBH_4$—$F_3CO_2H$.

SCHEMATIC 4

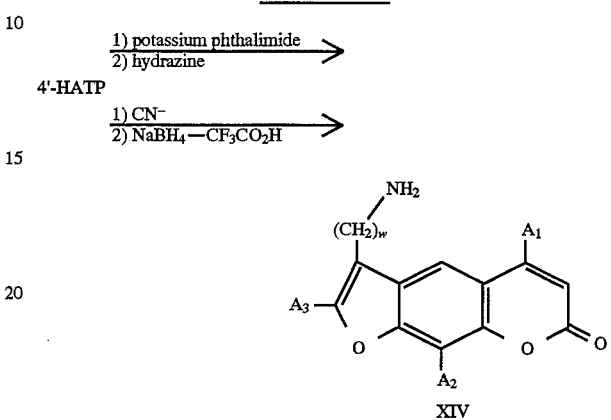

SCHEMATIC 3

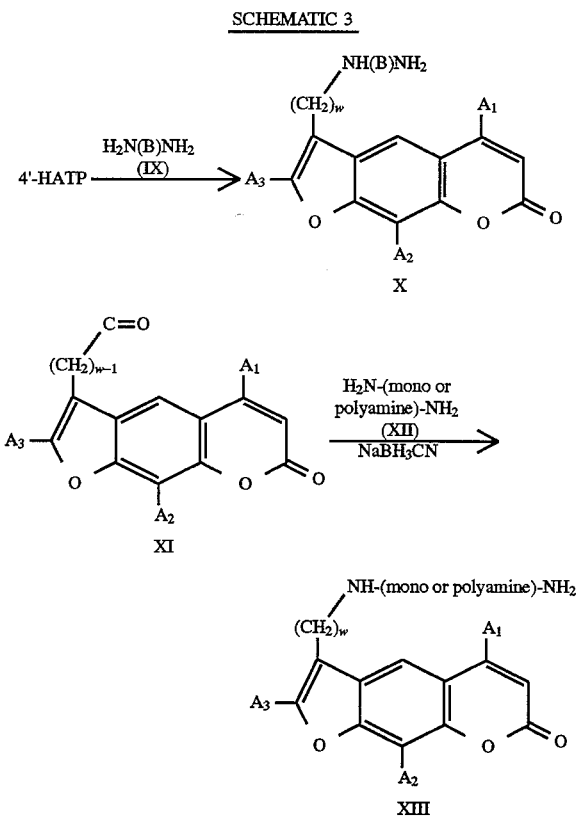

Other final products have a terminal amine linked to the psoralen by an alkyl chain. As shown in Schematic 4, below, The discussion of the conversion of 4,5',8-trialkylpsoralens to 4'-aminofunctionalized-4,5',8-trialkylpsoralens applies equally well when the 4- and/or 8-position is substituted with only a hydrogen, thus providing 4'-primaryamino-substituted-5', (4 or 8)- dialkylpsoralens and 4'-primaryamino-substituted-5'-alkylpsoralens.

Synthesis of 5' Derivatives

Under identical conditions to those described above, the 4,4',8-trialkylpsoralens or the 4,4',8-trialkyl-5'-methylpsoralens can be converted to the 5'-(ω-haloalkyl)-4, 4',8-trialkylpsoralens, (herein called 5'-HATP), as detailed in Schematic 5, below. (See Kaufman, U.S. Pat. No. 4,294,822 and 4,298,614 for modified version).

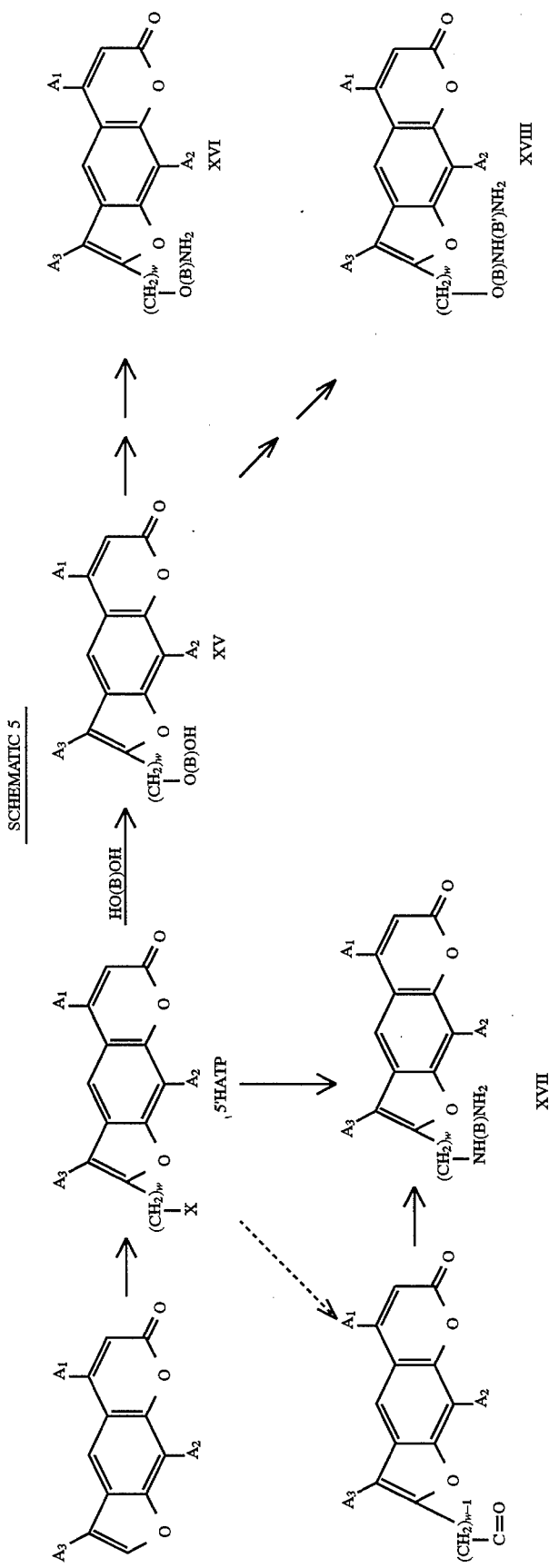

The discussion of the conversion of 4,4',8-trialkylpsoralens to 5'-primaryamino-substituted-4,4',8-trialkylpsoralens applies equally well when the 4-, 4'- and/or 8-positions are just substituted with a hydrogen, thus providing 5'-primaryamino-substituted-dialkylpsoralens and 5'-primaryamino-substitutedalkylpsoralens, with the alkyl group(s) at the 4-, 4'- and/or 8- positions.

The discussion above of the syntheses of 4'-primaryamino- and 5'-primaryamino-psoralens can be extended to the non-linear coumarins, specifically the isopsoralens or angelicins. Thus, the 4'-halomethylangelicins (XIX) and the 5'-halomethylangelicins (XX) can be prepared in a similar manner to their linear counterparts (see Schematic 6). By analogy with the synthetic pathways presented above one can envision the synthesis of 4'-(ω-amino)alkylangelicins and 5'-(ω-amino)alkylangelicins where the alkyl linkage can contain one or more oxygen or nitrogen atoms.

SCHEMATIC 6

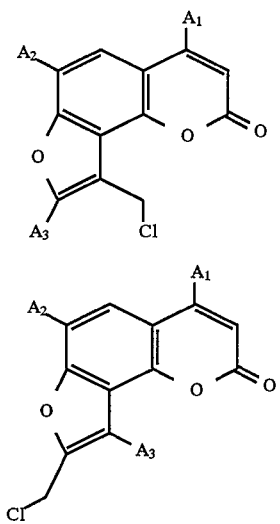

XIX

XX

III. BINDING OF COMPOUNDS TO NUCLEIC ACID

The present invention contemplates binding new and known compounds to nucleic acid, including (but not limited to) viral nucleic acid and bacterial nucleic acid. One approach of the present invention to binding photoactivation compounds to nucleic acid is photobinding. Photobinding is defined as the binding of photobinding compounds in the presence of photoactivating wavelengths of light. Photobinding compounds are compounds that bind to nucleic acid in the presence of photoactivating wavelengths of light. The present invention contemplates methods of photobinding with photobinding compounds of the present invention.

One embodiment of the method of the present invention for photobinding involves the steps: a) providing a photobinding compound of the present invention; and b) mixing the photobinding compound with nucleic acid in the presence of photoactivation wavelengths of electromagnetic radiation.

The invention further contemplates a method for modifying nucleic acid, comprising the steps: a) providing photobinding compound of the present invention and nucleic acid; and b) photobinding the photobinding compound to the nucleic acid, so that a compound:nucleic acid complex is formed. Without intending to be limited to any method by which the compounds of the present invention prevent replication, it is believed that the structure of said compound:nucleic acid complex serves to prevent replication of the nucleic acid by preventing the necessary polymerase from acting in the region where the compound has bound.

IV. INACTIVATION OF PATHOGENS

The present invention contemplates treating a blood product with a photoactivation compound and irradiating to inactivate contaminating pathogen nucleic acid sequences before using the blood product.

A. Inactivation In General

The term "inactivation" is here defined as the altering of the nucleic acid of a unit of pathogen so as to render the unit of pathogen incapable of replication. This is distinct from "total inactivation", where all pathogen units present in a given sample are rendered incapable of replication, or "substantial inactivation," where most of the pathogen units present are rendered incapable of replication. "Inactivation efficiency" of a compound is defined as the level of inactivation the compound can achieve at a given concentration of compound or dose of irradiation. For example, if 100 μM of a hypothetical compound X inactivated 5 logs of HIV virus whereas under the same experimental conditions, the same concentration of compound Y inactivated only 1 log of virus, then compound X would have a better "inactivation efficiency" than compound Y.

To appreciate that an "inactivation" method may or may not achieve "total inactivation," it is useful to consider a specific example. A bacterial culture is said to be inactivated if an aliquot of the culture, when transferred to a fresh culture plate and permitted to grow, is undetectable after a certain time period. A minimal number of viable bacteria must be applied to the plate for a signal to be detectable. With the optimum detection method, this minimal number is 1 bacterial cell. With a sub optimal detection method, the minimal number of bacterial cells applied so that a signal is observed may be much greater than 1. The detection method determines a "threshold" below which the "inactivation method" appears to be completely effective (and above which "inactivation" is, in fact, only partially effective).

B. Inactivation of Potential Pathogens

The same considerations of detection method and threshold exist when determining the sensitivity limit of an inactivation method for nucleic acid. Again, "inactivation" means that a unit of pathogen is rendered incapable of replication.

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occuring due to contact with the material. It is recognized that in this practical scenario, it is not essential that the methods of the present invention result in "total inactivation". That is to say, "substantial inactivation" will be adequate as long as the viable portion is insufficient to cause disease. Thus "substantially all" of a pathogen is inactivated when any viable portion of the pathogen which remaining is insufficient to cause disease. The inactivation method of the present invention renders nucleic acid in pathogens substantially inactivated. In one embodiment, the inactivation method renders pathogen nucleic acid in blood preparations substantially inactivated.

Without intending to be limited to any method by which the compounds of the present invention inactivate pathogens, it is believed that inactivation results from light induced binding of psoralens to pathogen nucleic acid. Further, while it is not intended that the inactivation method of the present invention be limited by the nature of the nucleic acid; it is contemplated that the inactivation method render all forms of nucleic acid (whether DNA, mRNA, etc.) substantially inactivated.

When photoactivation compounds are used to modify nucleic acid, the interaction of the pathogen nucleic acid (whether DNA, mRNA, etc.) with the photoactivation compound preferably prevents replication of the pathogen, such that, if a human is exposed to the treated pathogen, infection will not result.

"Synthetic media" is herein defined as an aqueous synthetic blood or blood product storage media. In one embodiment, the present invention contemplates inactivating blood products in synthetic media comprising a buffered saline solution. This method reduces harm to blood products and permits the use of much lower concentrations of photoactivation compounds.

TABLE 3

Viruses Photochemically Inactivated by Psoralens

| Family | Virus |
| --- | --- |
| Adeno | Adenovirus 2 |
|  | Canine hepatitis |
| Arena | Pichinde |
|  | Lassa |
| Bunya | Turlock |
|  | California encephalitis |
| Herpes | Herpes simplex 1 |
|  | herpes simplex 2 |
|  | Cytomegalovirus |
|  | Pseudorabies |
| Orothomyxo | Influenza |
| Papova | SV-40 |
| Paramyxo | Measles |
|  | Mumps |
|  | Parainfluenza 2 and 3 |
| Picorna[1] | Poliovirus 1 and 2 |
|  | Coxsackie A-9 |
|  | Echo 11 |
| Pox | Vaccinia |
|  | Fowl Pox |
| Reo | Reovirus 3 |
|  | Blue tongue |
|  | Colorado tick fever |
| Retro | HIV |
|  | Avian sarcoma |
|  | Murine sarcome |
|  | Murine leukemia |
| Rhabdo | Vesicular stomatitis virus |
| Toga | Western equine encephalitis |
|  | Dengue 2 |
|  | Dengue 4 |
|  | St. Louis encephalitis |
| Hepadna | hepatitis B |
| Bacteriophage | Lambda |
|  | T2 |
| (Rickettsia) | R. akari (rickettsialpox) |

[1]In the article, it was pointed out that Piconaviruses were photoinactivated only if psoralens were present during virus growth.

The psoralen photoinactivation method inactivates nucleic acid based pathogens present in blood through a single procedure. Thus, it has the potential to eliminate bacteria, protozoa, and viruses as well. Had an effective decontamination method been available prior to the advent of the AIDS pandemic, no transfusion associated HIV transmission would have occurred. Psoralen-based decontamination has the potential to eliminate all infectious agents from the blood supply, regardless of the pathogen involved. Additionally, psoralen-based decontamination has the ability to sterilize blood products after collection and processing, which in the case of platelet concentrates could solve the problem of low level bacterial contamination and result in extended storage life. Morrow J. F., et al., JAMA 266:555–558 (1991); Bertolini F., et al., Transfusion 32:152–156 (1992).

A list of viruses which have been photochemically inactivated by one or more psoralen derivatives appears in Table 3. (From Table 1 of Hanson, C. V., Blood Cells 18:7 (1992)). This list is not exhaustive, and is merely representative of the great variety of pathogens psoralens can inactivate. The present invention contemplates the inactivation of these and other viruses by the compounds described herein. The compounds of the present invention are particularly well suited for inactivating envelope viruses, such as the HIV virus.

C. Selecting Photoinactivation Compounds for Inactivation of Pathogens

In order to evaluate a compound to decide if it would be useful in the photochemical decontamination (PCD) methods of the present invention, two important properties should be considered: 1) the compound's ability to inactivate pathogens and 2) its mutagenicity. The ability of a compound to inactivate pathogens may be determined by several methods. One technique is to perform a bacteriophage screen; an assay which determines nucleic acid binding of test compounds. A screen of this type, an r-17 screen, is described in detail in EXAMPLE 12, below. If the r-17 screen shows inactivation activity, it is useful to directly test the compound's ability to inactivate a virus. One method of performing a direct viral inactivation screen is described in detail in EXAMPLE 13 for cell free HIV.

The R17 bacteriophage screen is believed to be predictive of HIV inactivation efficiency, as well as the efficiency of compounds against many other viruses. R17 was chosen because it was expected to be a very difficult pathogen to inactivate. It is a small, single stranded RNA phage. Without intending to be limited to any means by which the present invention operates, it is expected that shorter pieces of nucleic acid are harder to inactivate because they require a higher frequency of formation of psoralen adducts than do longer pieces of nucleic acid. Further, single stranded RNA pathogens are more difficult to inactivate because psoralens can neither intercalate between base pairs, as with double-stranded nucleic acids, nor form diadducts which function as interstrand crosslinks. Thus it is expected that when inactivation of R17 is achieved, these same conditions will cause the inactivation of many viruses and bacteria.

The cell free HIV screen complements the r-17 screen by affirming that a given compound which has tested positive in r-17 will actually work effectively to inactivate viruses. Thus, if a compound shows activity in the r-17 screen, it is next tested in the viral inactivation screen.

The second property that is important in testing a compound for use in methods of the present invention is mutagenicity. The most widely used mutagen/carcinogen screening assay is the Ames test. This assay is described by D. M. Maron and B. N. Ames in Mutation Research 113:173 (1983) and a specific screen is described in detail in Example 17, below. The Ames test utilizes several unique strains of Salmonella typhimurium that are histidine- dependent for growth and that lack the usual DNA repair enzymes. The frequency of normal mutations that render the bacteria independent of histidine (i.e., the frequency of spontaneous revertants) is low. The test allows one to evaluate the impact of a compound on this revertant frequency.

Because some substances are not mutagenic by themselves, but are converted to a mutagen by metabolic action, the compound to be tested is mixed with the bacteria on agar plates along with the liver extract. The liver extract serves to mimic metabolic action in an animal. Control plates have only the bacteria and the extract.

The mixtures are allowed to incubate. Growth of bacteria (if any) is checked by counting colonies. A positive Ames test is one where the number of colonies on the plates with mixtures containing the compound significantly exceeds the number on the corresponding control plates.

When known carcinogens are screened in this manner with the Ames test, approximately ninety percent are positive. When known noncarcinogens are similarly tested, approximately ninety percent are negative.

A new compound (X) can be evaluated as a potential blood photodecontamination compound, as shown in Table 4, below. X is initially evaluated in Step I. X is screened in the r-17 assay at several different concentrations between 4 and 320 µM, as explained in EXAMPLE 12. If the compound shows inactivation activity greater than 1 log inactivation of r-17 (log kill) in the r-17 screen at any concentration, the compound is then screened in the cell free HIV assay, as explained in EXAMPLE 13. If the compound shows inactivation activity greater than 1 log inactivation of HIV (log kill) in the cell free HIV assay, the compound and AMT are then screened in the Ames assay. Finally, if the compound shows lower mutagerdcity in the Ames assay than does AMT, the new compound is identified as a useful agent for inactivation of pathogens.

well established efficacious treatment for patients with thrombocytopenic bleeding. However, if the decontamination treatment used greatly reduces the platelets clotting activity, then the treatment has no practical value. Psoralens are useful in inactivation procedures, because the reaction can be carried out at temperatures compatible with retaining biochemical properties of blood and blood products. Hanson, C. V., Blood Cells 18:7 (1992). But not all psoralens or methods will decontaminate without significantly lowering the biological activity of the decontaminated material. Previous compounds and protocols have necessitated the removal of molecular oxygen from the reaction before exposure to light, to prevent damage to blood products from oxygen radicals produced during irradiation. See L. Lin et al., Blood 74:517 (1989); U.S. Pat. No. 4,727,027, to Wiesehahn. The present invention may be used to decontaminate blood products, in the presence of oxygen, without destroying the in vivo activity for which the products are prepared. The present invention contemplates that in vivo activity of

TABLE 4

| STEP | SCREEN | RESULT | INTERPRETATION |
|---|---|---|---|
| 1 | r-17 | >1 log kill by any concentration | potential PCD compound, go to step 2 |
|  |  | <1 log kill | compound is ineffective as an inactivation treatment |
| 2 | Viral Inactivation | >1 log kill by any concentration | potential PCD compound, go to step 3 |
|  |  | <1 log kill | compound is ineffective as an inactivation treatment |
| 3 | Ames | less mutagenic than AMT | useful agent for PCD |

By following these instructions, a person can quickly determine which compounds would be appropriate for use in methods of the present invention.

D. Delivery of Compounds for Photoinactivation

The present invention contemplates several different formulations and routes by which the compounds described herein can be delivered in an inactivation method. This section is merely illustrative, and not intended to limit the invention to any form or method of introducing the compound.

The compounds of the present invention may be introduced in an inactivation method in several forms. The compounds may be introduced as an aqueous solution in water, saline, a synthetic media such as "Sterilyte™ 3.0" (contents set forth at the beginning of the Experimental section, below) or a variety of other solvents. The compounds can further be provided as dry formulations, with or without adjuvants.

The new compounds may also be provided by many different routes. For example, the compound may be introduced to the reaction vessel, such as a blood bag, at the point of manufacture. Alternatively, the compound may be added to the material to be sterilized after the material has been placed in the reaction vessel. Further, the compounds may be introduced alone, or in a "cocktail" or mixture of several different compounds.

V. PRESERVATION OF BIOCHEMICAL PROPERTIES OF MATERIAL TREATED

When treating blood products to be used in vivo, two factors are of paramount importance in developing methods and compounds to be used. First, one must ask whether the process or the compounds used alter the in vivo activity of the treated material. For example, platelet transfusion is a blood product is not destroyed or significantly lowered if a sample of blood product which is decontaminated by methods of the present invention tests as would a normally functioning sample of blood product in known assays for blood product function. For example, where platelets are concerned, in vivo activity is not destroyed or significantly lowered if aggregation and pH of the platelets are substantially the same in platelets treated by the methods of the present invention and stored 5 days as they are in untreated samples stored for 5 days. "Substantially the same" pH and aggregation means that the values fall within the range of error surrounding that particular data point.

The second factor is whether the compounds used are toxic or mutagenic to the patient treated. A "compound displaying low mutagenicity" is defined as a compound which is less mutagenic than AMT when it is tested at concentrations below 250 µM in the Ames assay, described in the Experimental section, below. The inactivation compounds and methods of the present invention are especially useful because they display the unlinking of pathogen inactivation efficiency from mutagenicity. The compounds exhibit powerful pathogenic inactivation without a concomitant rise in mutagenicity. The commonly known compounds tested in photoinactivation protocols, such as AMT, appear to exhibit a link between pathogen inactivation efficiency and mutagenetic action that until now seemed indivisible.

While it is not intended that the present invention be limited to any theory by which pathogen inactivation efficiency is unlinked from mutagenicity, it is postulated that unlinking occurs as a result of the length of the groups substituted on the psoralen, and the location of charges on the compounds. It is postulated that positive charges on one or both ends of mutagenic compounds have non-covalent interactions with the phosphate backbone of DNA. These interactions are presumed to occur independent of the presence of light (called "dark binding"). In theory, the psoralen thereby sterically blocks polymerase from opening up the DNA, causing mutagenicity. In contrast, compounds of the present invention carry a positive or neutral charge on a long substitute group. These substituted groups form a steric barrier during dark binding that is much easier to free from the DNA, permitting polymerase to pass. Thus no mutagenicity results.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); µL (microliters); cm (centimeters); mm (millimeters); µm (micrometers); nm (nanometers); J (Joules, also watt second, note that in FIGS. 6, 8–17 Joules or J refers to Joules/cm$^2$); °C. (degrees Centigrade); TLC (Thin Layer Chromatography); EAA (ethyl-acetoacetate); EtOH (ethanol); HOAc (acetic acid); W (watts); mW (milliwatts); NMR (Nuclear Magnetic Resonance; spectra obtained at room temperature on a Varian Gemini 200 MHz Fourier Transform Spectrometer); m.p. (melting point); UV (ultraviolet light); THF (tetrahydrofuran); DMEM (Dulbecco's Modified Eagles Medium); FBS (fetal bovine serum); LB (Luria Broth); EDTA (ethelene diamine tetracidic acid); Phorbol Myristate Acetate (PMA); phosphate buffered saline (PBS).

For ease of reference, some compounds of the present invention have been assigned a number from 1–18. The reference numbers are assigned in TABLE 2, Their structures appear in FIGS. 5A–5F. The reference numbers are used throughout the experimental section.

When isolating compounds of the present invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates. Other acids are likewise suitable and may be employed as desired. For example, fumaric, benzoic, ascorbic, succinic, salicylic, bismethylenesalicylic, propionic, gluconic, malic, malonic, maudelie, cinnamic, citraconic, stearic, palmitic, itaconic, glycolic, benzenesulphonic, and sulphamic acids may also be employed as acid addition salt-forming acids.

One of the examples below refers to HEPES buffer. This buffer contains 8.0 g of 137 mM NaCl, 0.2 g of 2.7 mM KCl, 0.203 g of 1 mM MgCl$_2$(6H$_2$O), 1.0 g of 5.6 mM glucose, 1.0 g of 1 mg/ml Bovine Serum Albumin (BSA) (available from Sigma, St. Louis, Mo.), and 4.8 g of 20 mM HEPES (available from Sigma, St. Louis, Mo.).

In one of the examples below, phosphate buffered synthetic media is formulated for platelet treatment. This can be formulated in one step, resulting in a pH balanced solution (e.g. pH 7.2), by combining the following reagents in 2 liters of distilled water:

| Preparation of Sterilyte ™ 3.0 | | | |
|---|---|---|---|
| | Formula W. | mMolarity | Grams/2 Liters |
| NaAcetate*3H$_2$O | 136.08 | 20 | 5.443 |
| Glucose | 180.16 | 2 | 0.721 |
| D-mannitol | 182.17 | 20 | 7.287 |
| KCl | 74.56 | 4 | 0.596 |
| NaCl | 58.44 | 100 | 11.688 |
| Na$_3$ Citrate | 294.10 | 10 | 5.882 |
| Na$_2$HPO$_4$*7H$_2$O | 268.07 | 14.46 | 7.752 |
| NaH$_2$PO$_4$*H$_2$O | 137.99 | 5.54 | 1.529 |
| MgCl$_2$*6H$_2$O | 203.3 | 2 | 0.813 |

The solution is then mixed, sterile filtered (0.2 micron filter) and refrigerated.

The Polymerase Chain Reaction (PCR) is used in one of the examples to measure whether viral inactivation by some compounds was complete. PCR is a method for increasing the concentration of a segment of a target sequence in a mixture of genomic DNA without cloning or purification. See K. B. Mullis et al., U.S. Pat. Nos. 4,683,195 and 4,683,202, hereby incorporated by reference. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction". Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g. hybridization with a labelled probe; incorporation of biotinylated primers followed by avidin-enzyme conjugate detection; incorporation of $^{32}$P labelled deoxynucleotide triphosphates, e.g. dCTP or dATP, into the amplified segment). In addition to genomic DNA, any oligonucleotide sequence can be amplified with the appropriate set of primer molecules.

The PCR amplification process is known to reach a plateau concentration of specific target sequences of approximately 10$^{-8}$ M. A typical reaction volume is 100 µl, which corresponds to a yield of 6×10$^{11}$ double stranded product molecules.

PCR is a polynucleotide amplification protocol. The amplification factor that is observed is related to the number (n) of cycles of PCR that have occurred and the efficiency of replication at each cycle (E), which in turn is a function of the priming and extension efficiencies during each cycle. Amplification has been observed to follow the form $E^n$, until high concentrations of PCR product are made. At these high concentrations (approximately $10^{-8}$ M/l) the efficiency of replication fails off drastically. This is probably due to the displacement of the short oligonucleotide primers by the longer complementary strands of PCR product. At concentrations in excess of $10^{-8}$ M, the rate of the two complementary PCR amplified product strands finding each other during the priming reactions become sufficiently fast that this occurs before or concomitant with the extension step of the PCR procedure. This ultimately leads to a reduced priming efficiency, and therefore, a reduced cycle efficiency. Continued cycles of PCR lead to declining increases of PCR product molecules. PCR product eventually reaches a plateau concentration.

The sequences of the polynucleotide primers used in this experimental section are as follows:

DCD03: 5' ACT AGA AAA CCT CGT GGA CT 3'
DCD05: 5' GGG AGA GGG GAG CCC GCA CG 3'
DCD06: 5' CAA TTT CGG GAA GGG CAC TC 3'
DCD07: 5' GCT AGT ATT CCC CCG AAG GT 3'

With DCD03 as a common forward primer, the pairs generate amplicons of length 127, 327, and 1072 bp. These oligos were selected from regions that are absolutely conserved between 5 different dHBV isolates (DHBV1, DHBV3, DHBV16, DHBV22, and DHBV26) as well as from heron HBV (HHBV4).

The following examples serve to illustrate certain preferred embodiments and aspects of the present invention and are not to be construed as limiting the scope thereof.

EXAMPLE 1

As noted above, the present invention contemplates devices and methods for the photoactivation of photoreactive nucleic acid binding compounds. In this example, a photoactivation device is described for decontaminating blood products according to the method of the present invention. This device comprises: a) means for providing appropriate wavelengths of electromagnetic radiation to cause photoactivation of at least one photoreactive compound; b) means for supporting a plurality of blood products in a fixed relationship with the radiation providing means during photoactivation; and c) means for maintaining the temperature of the blood products within a desired temperature range during photoactivation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (100) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

FIG. 2 is a cross-sectional view of the device shown in FIG. 1 along the lines of 2—2. FIG. 2 shows the arrangement of the bulbs (101) with the housing (100) opened. A reflector (108A, 108B) completely surrounds each array of bulbs (101). Blood product containing means (102) are placed between upper (103) and lower (104) plate assemblies. Each plate assembly is comprised of an upper (103A, 104A) and lower (103B, 104B) plates. The plate assemblies (103, 104) are connected via a hinge (109) which is designed to accommodate the space created by the blood product containing means (102). The upper plate assembly (103) is brought to rest just above the top of the blood product containing means (102) supported by the lower plate (104B) of the lower plate assembly (104).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

FIG. 3 is a cross-sectional view of the device shown in FIG. 1 along the lines of 3—3. Six blood product containing means (102) (e.g. Teflon™ platelet unit bags) are placed in a fixed relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

FIG. 4 is a cross-sectional view of the device shown in FIG. 1 along the lines of 4—4. FIG. 4 more clearly shows the temperature control approach of a preferred embodiment of the device. Upper plate assembly plates (103A, 103B) and lower plate assembly plates (104A, 104B) each create a temperature control chamber (103C, 104C), respectively. The fan (112) can circulate air within and between the chambers (103C, 104C). When the heat exchanger (113) is employed, the circulating air is cooled and passed between the plates (103A, 103B, 104A, 104B).

EXAMPLE 2

Synthesis of 4'-Bromomethyl-4,5',8-trimethylpsoralen

In this example, the three step synthesis of 4'-Bromomethyl-4,5',8-trimethylpsoralen is described. This synthesis is performed without a bromomethylation step, making it safer than known methods of synthesis.

Step 1: 3-Chloro-2-butanone (29.2 mL, 0.289 mol) was added to a mechanically stirred suspension of 7-hydroxy-4,8-dimethylcoumarin (50.00 g, 0.263 mol) and powdered $K_2CO_3$ (54 g, 0.391 mol) in acetone (500 mL). The slurry was refluxed overnight, after which the solvent was stripped off. To remove the salt, the solid was stirred in 1.2 L of water, filtered, and rinsed with water until the pH of the mother liquor was neutral (pH 5–7). The brown flitrate was dissolved in boiling methanol (150 mL), allowed to cool to room temperature to form a thick paste and rinsed with ice cold methanol to remove most of the brown impurity, giving 4,8-dimethyl-7-(1-methyl-2-oxo)propyloxy-coumarin (67.7 g, 99.0% yield) as an off-white solid, melting point 95°–96° C. NMR: d 1.57 (d, J=6.7 Hz, 3H), 2.19 (s, 3H), 2.39 (s, 6H), 4.73 (q, J=6.9 Hz, 1H), 6.17 (s, 1H), 6.63 (d, J=8.8 Hz, 1H), 7.38 (d, J=8.9 Hz, 1H).

Step 2: A suspension of 4,8-dimethyl-7-(1-methyl-2-oxo) propyloxy-coumarin (67.5 g, 0.260 mol), 10% aqueous NaOH (114 mL, 0.286 mol) and water (900 mL) was heated for 2–4 hours at 70°–85° C. The mixture was then allowed to cool to room temperature. The solid was filtered, and then rinsed with chilled water (1.5 L) until the mother liquor became colorless and pH was neutral (pH 5–7). The product was air and vacuum dried to give 4, 4',5',8-tetramethylpsoralen (56.3 g, 89.5%) as a white solid, mp 197°–199° C. NMR: d 2.19 (s, 3H), 2.42 (s, 3H), 2.51 (s, 3H), 2.56 (s, 3H), 6.23 (s, 1H), 7.40 (s, 1H).

Step 3: Dry 4,4',5',8-tetramethylpsoralen (10.00 g, 41.3 mmol) was dissolved in methylene chloride (180 mL) at room temperature. N-Bromosuccinimide (8.09 g, 45.3 mmol) was added and the reaction mixture and stirred 4.5 hours. The solvent was completely removed and the resulting solid was stirred with water (200 mL) for 0.5–1 h, filtered and cold triturated with additional water (approximately 500 mL) to remove the succinimide by-product. The crude product (i.e. 4'-bromomethyl-4,5',8-trimethylpsoralen) was dried in a vacuum dessicator with $P_2O_5$ then recrystallized in a minimum amount of boiling toluene (200–300 mL) to give 4'-bromomethyl-4,5',8-trimethylpsoralen (10.2 g), a pale yellow solid. The mother liquor was stripped and recrystallized again with toluene (60 mL) to give a second crop of product (1.08 g, combined yield=85.1%, >99% purity by NMR), mp 206°–207° C. NMR: d 2.50 (s, 3H), 2.54 (d, J=1.2 Hz, 3H), 2.58 (s, 3H), 4.63 (s, 2H), 6.28 (apparent q, J=1.3 Hz, 1H), 7.59 (s, 1H).

EXAMPLE 3

Synthesis of 5'-bromomethyl-4,4',8-trimethylpsoralen

In this example, a three step synthesis of 5'-bromomethyl-4,4',8-trimethylpsoralen is described. Like the synthesis described in Example 2, this method is improved upon previously known synthesis schemes because it does not require bromomethylation.

4,4',5',8-Tetramethylpsoralen (2.33 g, 9.59 mmol), (synthesis described in Example 2, Steps 1 and 2), was refluxed in carbon tetrachloride (100 mL) until it dissolved. N-Bromosuccinimide (1.88 g, 10.5 mmol) and benzoyl peroxide (80 mg) were then added and the mixture was refluxed for 15 hours. Upon cooling to room temperature methylene chloride (100 mL) was added to dissolve the solid and the solution was washed with water (4×150 mL), then brine, and dried with anhydrous $Na_2SO_4$. The solvent was stripped off to give a mixture of 5'-bromomethyl-4,4',8-trimethylpsoralen, 4'-bromomethyl-4,5',8-trimethylpsoralen, and 4',5'-bis(bromomethyl)-4,8-dimethylpsoralen in a ratio of 55/25/20 respectively as determined by $^1$H NMR (3.0 g, crude product). $^1$H NMR of 5'-bromomethyl compound: d 2.29 (s, 3H), 2.52 (d, J=1.2 Hz, 3H), 2.60 (s, 3H), 4.64 (s, 2H), 6.27 (apparent d, J=1.2 Hz, 1H), 7.51 (s,1H). $^1$H NMR of 4',5'-bis(bromomethyl) compound: d 2.54 (d, J=1.1 Hz, 3H), 2.60 (s, 3H), 4.65 (s, 4H), 6.30 (apparent q, J=1.1 Hz, 1H), 7.67 (s, 1H).

EXAMPLE 4

Synthesis of 4'-(4-amino-2-oxa)butyl-4,5',8-trimethylpsoralen Hydrochloride (Compound 2) and Related Compounds (Compound 4)

In this example, two methods of synthesis of Compound 2 are described. The first method was performed as follows:

Step 1: 4'-Bromomethyl-4,5',8-trimethylpsoralen (3.09 g, 9.61 mmol), (synthesis described in Example 2), and N-(2-hydroxyethyl)phthalimide (4.05 g, 21.2 mmol) were stirred in dry dimethylformamide (65 mL). Dry $N_2$ gas was bubbled gently into the reaction mixture. The reaction mixture was heated to 100° C. for 4.5 hours then allowed to cool to room temperature and put in the freezer for several hours. The crystalline product was filtered and washed with MeOH followed by $H_2O$. The solid was further tritutrated with MeOH (100 mL) to remove the impurities. The crude product was air dried and dissolved in $CHCl_3$ (150 mL). Activated carbon and silica gel were added to decolorize and the $CHCl_3$ was completely removed. The resulting white product, 4'-[4-(N-phthalimido)-2-oxa]butyl-4,5',8-trimethylpsoralen (1.56 g, yield 37.5%) was ≧99% pure both by NMR and HPLC; mp 224°–225° C. NMR ($CDCl_3$) δ 2.37 (s,3H); 2.47 (s, 3H); 2.48 (s, 3H); 3.78 (s,4H); 4.59 (s,2H); 6.22 (s, 1H); 7.42 (s,1H); 7.50 (m, 4H).

Step 2: 4'-[4-(N-phthalimido)-2-oxa]butyl-4,5',8-trimethylpsoralen (1.56 g, 3.61 mmol) was suspended in tetrahydrofuran (75 mL) at room temperature. Methylamine (40% aqueous solution, 25 mL, 290 mmol) was added to the suspension and stirred overnight. The solvent and methylamine were completely removed. The resulting solid was taken up in 0.3 N HCl aqueous solution (25 mL). The acid suspension was rinsed three times with 40 mL $CHCl_3$ then taken to pH 11 with 20% aqueous NaOH. $CHCl_3$ (3×60 mL) was used to extract the product (i.e. 4'-(4-amino-2-oxa) butyl-4,5',8-trimethylpsoralen) from the basified layer. The combined $CHCl_3$ layers were washed with $H_2O$ (100 mL) followed by brine (100 mL) then dried over anhydrous $Na_2SO_4$ and concentrated to give 4'-(4-amino-2-oxa)butyl-4,5',8-trimethylpsoralen, mp 139°–141° C. Purity was greater than 99% by NMR. NMR ($CDCl_3$) δ 2.50 (s, 6H); 2.58 (s,3H); 2.90 (t, J=5.27 Hz, 2H); 3.53 (t, J=5.17 Hz, 2H); 4.66 (s, 2H); 6.25 (s, 1H); 7.61 (s, 1H). The 4'-(4-amino-2-oxa)butyl-4,5',8-trimethylpsoralen was dissolved in absolute ethanol (150 mL), a 1.0 M solution of HCl in ether (10 mL) was added and the suspension was cooled in the freezer overnight. After filtration and washing with ether, the solid was vacuum dried to give pale yellow crystals (0.76 g, yield 62%), mp 235°–236° C.

The first method is a preferred embodiment of the present invention because of its high yield and purity.

The second method starts with the preparation of 4'-chloromethyl-4,5',8-trimethylpsoralen from commercially available 4,5',8-trimethylpsoralen, as described above. The synthesis of 4'-(4-amino-2-oxa)butyl-4,5',8-trimethylpsoralen hydrochloride is achieved in four (4) steps:

STEP 1: 4'-Chloromethyl-4,5',8-trimethylpsoralen (550 mg, 1.99 mmol) and ethylene glycol (6.8 ml, 121.9 mmol) were heated in acetone (6 mL) to 50°–60° C. for 3.5 hrs. After 2 hrs heating, the white suspension had turned to a clear light yellow solution. The acetone and ethylene glycol were removed on the rotoevaporator and water (50 mL) was added to the residue. The resultant suspension was filtered, washed with cold water then dried in the vacuum oven to give 574 mg (96%) of 4'-(4-hydroxy-2-oxa)butyl-4,5',8-trimethylpsoralen; NMR ($CDCl_3$) δ 2.51 (s, 6H); 2.58 (s, 3H); 3.62 (t, J=4.5 Hz, 2H); 3.78 (t, J=4.9 Hz, 2H); 4.70 (s, 2H); 6.26 (d, J=1.1 Hz, 1H); 7.61 (s, 1H).

STEP 2: 4'-(4-Hydroxy-2-oxa)butyl-4,5',8-trimethylpsoralen (574 mg, 1.9 mmol) was dissolved in CH$_2$Cl$_2$ (6 mL) under N$_2$ at ≦10° C. Triethylamine (359 mg, 3.55 mmol) was added. Methanesulfonyl chloride (305 mg, 266 mmol) was dropped in slowly keeping the temperature below 10° C. After addition was completed the mixture was stirred for 15 more minutes and then it was stirred at room temperature for 10 hours. To the reacted suspension CH$_2$Cl$_2$ (45 mL) was added and the mixture was washed with water (3×20 mL), then dried over anhydrous Na$_2$SO$_4$. Concentration at ≦30° C. followed by vacuum drying gave 4'-[(4-methanesulfonyloxy-2-oxa)butyl-4,5',8-trimethylpsoralen as a yellow solid (706 mg, 98%), mp 138°–140° C. NMR a 2.51 (s, 3H); 2.52 (d, 3H); 2.58 (s, 3H); 2.99 (s, 3H); 3.77 (m ,2H); 4.39 (m, 2H); 4.71 (s, 2H); 6.26 (s, 1H); 7.62 (s, 1H).

STEP 3: 4'-[(4-Methanesulfonyloxy-2-oxa)butyl-4,5',8-trimethylpsoralen (706 mg, 1.86 mmol) and sodium azide (241 mg, 3.71 mmol) were refluxed in 95% ethyl alcohol (5 mL) for 8 hours. The reaction solution was cooled and cold water (55 mL) was added. The off-white solid was filtered and washed with cold water. Upon vacuum drying, the azide (i.e. 4'-(4-Azido-2-oxa)butyl-4,5',8-trimethylpsoralen) was obtained as a light yellowish solid (575 mg, 95%), mp 105°–106° C. NMR: δ 2.51 (s, 6H); 2.58 (s, 3H); 3.41 (t, J=4.9 Hz, 2H); 3.67 (apparent t, J=4.9 Hz, 2H); 4.70 (s, 2H); 6.26 (s, 1H); 7.66 (s, 1H).

STEP 4: The 4'-(4-Azido-2-oxa)butyl-4,5',8-trimethylpsoralen (1.65 g, 5.03 mmol) was dissolved in tetrahydrofuran (10 mL). Triphenylphosphine (1.59 g, 6.08 mmol) and six drops of water were added to the foregoing solution. After stirring at room temperature overnight, the light yellow solution was concentrated. The residue was dissolved in CHCl$_3$ (90 mL) and extracted with 0.3 N aqueous HCl (30 mL, then 2×5 mL). Combined HCl layers was carefully treated with K$_2$CO$_3$ until saturated. The base solution was extracted with CHCl$_3$ (3×60 mL). Combined CHCl$_3$ layers were washed with 60 mL of water, 60 mL of brine and dried over anhydrous Na$_2$SO$_4$. Upon concentration and vacuum drying the amine (i.e. was obtained as a yellow solid (1.25 g, 82%), mp 139°–141° C.; NMR δ 2.48 (s, 6H); 2.55 (s, 3H); 2.89 (t, J=6 Hz, 2H); 3.52 (t, J=6 Hz, 2H); 4.64 (s, 2H); 6.22 (s, 1H); 7.59 (s, 1H).

The amine was dissolved in absolute ethanol (40 mL) and 20 mL of 1N HCl in ethyl ether was added. After sitting at 5° C. overnight, the precipitate was filtered and rinsed with ether to give 1.25 g of Compound 2, mp 236° C. (decomp).
$^{13}$C NMR: 8.54, 12.39, 19.18, 38.75, 62.26, 65.80, 108.01, 112.04, 112.42, 112.97, 116.12, 125.01, 148.76, 153.97, 154.37, 155.76, 160.34.

Anal. Calculated for C$_{17}$H$_{20}$ClNO$_4$: C, 60.45: H, 5.97; N, 4.15. Found: C, 60.27; H, 5.88; N, 4.10.

Similarly prepared, by reacting 4'-CMT with 1,3-propanediol comparably to Step 1 and proceeding analagously through Step 4, was 4'-(5-amino-2-oxa)pentyl-4,5',8-trimethylpsoralen, (Compound 4), m.p. 212°–214° C. (decomposed). NMR of the free base: δ 1.73 (pent, J=6.4 Hz, 2H), 2.45 (s, 6H), 2.51 (s, 3H), 2.78 (t,J=6.8 Hz, 2H), 3.54 (t, J=6.2 Hz, 2H), 4.59 (s,2H), 6.18 (s, 1H), 7.54 (s, 1H).

EXAMPLE 5

Synthesis of 5'-(4-Amino-2-oxa)butyl-4,4',8-trimethylpsoralen (Compound 18)

This example describes the synthesis of Compound 18. To a stirred solution of N-methylformanilide (16.0 mL, 0.134 mol) in acetonitrile (130 mL) was added phosphorus oxychloride (12.5 mL, 0.134 mol), then 4,4',8-trimethylpsoralen (5.0 g, 21.9 mmol) (described in McLeod, et al., Tetrahedron Letters No. 3:237 (1972)). The temperature was kept between 0°–10° C. during addition of the psoralen by use of an ice/water bath. The slurry was stirred at 50° C. for 2 days protected from moisture with a drierite drying tube. The reaction mix was allowed to cool to room temperature, then chilled in an ice/water bath. The acetonitrile was decanted off, then ice/water (150 mL) was added to the orange slurry and stirred for 1 h. The orange solid was filtered off and rinsed with chilled water, then chilled acetonitrile. The crude product was recrystallized and charcoal decolorized in dichloroethane (600 mL) to give 4,4',8-trimethyl-5'-psoralencarboxaldehyde (3.59 g, 64.0%) as a pale yellow-orange solid, sublimes≧250° C., decomp.>300° C. $^1$H NMR (CDCl$_3$): 2.54 (d, J=1 Hz, 3H), 2.64 (s, 3H), 2.68 (s, 3H), 6.32 (apparent d, J=1 Hz, 1H), 7.75 (s, 1H), 10.07 (s, 1H).

4,4',8-trimethyl-5-psoralencarboxaldehyde (7.50 g, 29.3 mmol) was stirred in 200proof EtOH (250 mL). Sodium borohydride was added and the slurry was stirred overnight. Ice water (150 mL) and 10% aq NaCO$_3$ (50 mL) were added to quench the reaction. After stirring for 45 min, the precipitate was filtered off and rinsed with water until the flitrate was neutral (pH 5–7). The product was dried in a vacuum dessicator with P$_2$O$_5$ to give 5'-hydroxymethyl-4,4',8-trimethylpsoralen (7.46 g, 98.5%) as a pale yellow solid, mp 244°–245° C. $^1$H NMR (CDCl$_3$): 1.97 (t, J=6 Hz, 1H), 2.31 (s, 3H), 2.51 (d, J=1 Hz, 3H), 2.58 (s, 3H), 4.79 (d, J=6 Hz, 2H), 6.25 (apparent d, J=1 Hz, 1H), 7.49 (s, 1H).

To a stirred, ice/water chilled slurry of 5'-hydroxymethyl-4,4',8-trimethylpsoralen (15.42 g, 59.7 mmol) in dichloroethane phosphorus tribromide (6.17 mL, 65.7 mmol) dropwise. The reaction was protected from moisture and allowed to stir overnight at room temperature. The mixture was then stirred with 300 mL ice/water for 1 h. The solid was filtered off, dried, dissolved in hot toluene, filtered through fluted filter paper and stripped to give 5'-bromomethyl-4,4',8-trimethylpsoralen (3.43 g). The reaction solvents (dichloroethane and water) were separated and the aqueous layer was extracted three times with dichloroethane. The organic layers were combined, rinsed with brine then dried (anhyd Na$_2$SO$_4$) and stripped under vacuum to give the bulk of the product, 5'-bromomethyl-4,4',8-trimethylpsoralen, (13.13 g, combined yield of 86.4%), as a pale yellow solid, mp 201°–202° C. $^1$H NMR (CDCl$_3$): 2.29 (s, 3H), 2.52 (d, J=1 Hz, 3H), 2.60 (s, 2H), 4.64 (s, 2H), 6.27 (apparent d, J=1Hz, 1H), 7.51 (s, 1H) N-Hydroxyethylphthalimide (3.00 g, 15.5 mmol) was dissolved in DMF (5 mL) at 60°–64° C. while N$_2$ was bubbled into the solution. Sodium iodide (0.01 g, 0.067 mmol) and 5'-bromomethyl-4,4',8-trimethylpsoralen (1.00 g, 3.11 mmol) were added and the slurry was stirred under these conditions overnight. The thick yellow reaction mixture was allowed to cool to room temperature, chilled in an ice/water bath, filtered and rinsed with ice cold MeOH to give crude product (1 g). The solid was recrystallized in dichloroethane (100 mL) to give 4,4',8-trimethyl-5'-[2-(N-phthalimido)-2-oxa]butylpsoralen (0.68 g, 50.8%), as an off-white solid, mp 225°–228° C. $^1$H NMR (CDCl$_3$): 2.26 (s, 3H), 2.46 (s, 3H), 2.51 (d, J=1 Hz, 3H), 3.87 (m, 4H), 4.64 (s, 2H), 6.26 (apparent d, J=1 Hz, 1H), 7.42 (s, 1H), 7.64 (multiplet, 4H).

4,4',8-Trimethyl-5'-[4'-(N-phthalimido)-2-oxa] butylpsoralen (1.61 g, 3.73 mmol) was stirred with THF (40 mL) and 40 wt % aq methylamine (20 mL, 257 mmol) overnight. The solvent was stripped and the residue was partitioned between dilute aq HCl and dichloromethane. The aqueous layer was rinsed several more times with dichloromethane then made basic with $K_2CO_3$. The base layer was extracted three times with dichloromethane. The combined organic extracts from the base shaken with brine then dried (anhydrous $Na_2SO_4$) and stripped to give 5'-(4-amino-2-oxa)butyl-4,4',8-trimethylpsoralen (0.71 g, 63.4%), mp 126°–129° C. $^1$H NMR (CDCl$_3$): 2.30 (s, 3H), 2.51 (s, 3H), 2.58 (s, 3H), 2.91 (t, J=5 Hz, 2H), 3.59 (t, J=5 Hz, 2H), 4.64 (s, 2H), 6.25 (s, 1H), 7.50 (s, 1H).

The above amine (0.71 g, 2.36 mmol) was dissolved in hot ethanol, converted to the acid with 1 M HCl in diethylether (3 mL, 3 mmol), decolorized with charcoal, cooled and collected. The solid was decolorized again with charcoal and stripped to give 5'-(4-amino-2-oxa)butyl-4,4',8-trimethylpsoralen hydrochloride (0.39 g, 49.3% yield) as a white solid, mp 235°–236° C. (Note: Other preparations of this material have given a product with a significantly lower melting point, but identical NMR spectra). $^1$H NMR (d6-DMSO): 2.32 (s, 3H), 2.45 (s, 3H), 2.50 (s, 3H), 3.00 (m, 2H), 3.71 (t, J=5 Hz, 2H), 4.71 (s, 2H), 6.33 (s, lift), 7.79 (s, 1H), 8.15 (br). $^{13}$C NMR (d6-DMSO): 7.93, 8.57, 19.01, 38.74, 62.66, 66.28, 108.22, 112.42, 113.69, 115.34, 116.06, 125.60, 149.38, 150.95, 154.26 (tentatively 2 carbons), 160.26.

EXAMPLE 6

Synthesis of 4'-(7-amino-2,5-oxa)heptyl-4,5',8-trimethylpsoralen Hydrochloride (Compound 7)

In this example, the synthesis of Compound 7 is described. The synthesis of 4'-(7-amino-2,5-oxa)heptyl-4,5', 8-trimethylpsoralen hydrochloride proceeds in four (4) steps:
STEP 1: 4'-Chloromethyl-4,5',8-trimethylpsoralen (589 mg, 2.13 mmol), diethylene glycol (15.4 g, 145 mmol) and acetone (13 mL) were refluxed for 11.5 hours. The reaction solution was concentrated to remove acetone and part of the diethylene glycol. To the resulting light brown solution was added CHCl$_3$ (40 mL), then washed with water several times. The CHCl$_3$ layer was dried over anhydrous $Na_2SO_4$ and concentrated to give 781 mg of product, 4'-(7-Hydroxy-2,5-oxa)heptyl-4,5',8-trimethylpsoralen, (~100%). NMR δ 2.46 (d, 3H), 2.47 (s, 3H ), 2.51 (s, 3H), 3.58–3.67 (m, 8H), 4.67 (s, 2H), 6.18 (s, 1H), 7.57 (s, 1H).
STEP 2: 4'-(7-Hydroxy-2,5-oxa)heptyl-4,5',8-trimethylpsoralen (781 mg, 2.25 mmol) was dissolved in CH$_2$Cl$_2$ (2.5 mL) under a $N_2$ stream at <10° C. Triethylamine (363 mg, 3.59 mmol) was added. Methanesulfonyl chloride (362 mg, 3.16 mmol) was slowly dropped in to keep the temperature below 10° C. After addition was completed, the mixture was kept below 10° C. for 15 more minutes. The mixture was stirred at room temperature overnight then CH$_2$Cl$_2$ (50 mL) was added. The solution was washed with water (3×60 mL), dried over anhydrous $Na_2SO_4$ and concentrated at ≤30° C. Upon vacuum drying, a light brown syrup was obtained [4'-(7-Methanesulfonyloxy-2,5-oxa) heptyl-4,5',8-trimethylpsoralen]; 437 mg (76%). NMR δ 2.50 (s, 3H), 2.51 (s, 3H), 2.58 (s, 3H), 3.01 (s, 3H), 3.66 (m, 4H), 3.77 (t,J=4.6 Hz, 2H), 4.37 (t, J=6 Hz, 2H), 4.69 (s, 2H), 6.25 (s, 1H), 7.61 (s, 1H)
STEP 3: 4'-(7-Methanesulfonyloxy-2,5-oxa)heptyl-4,5',8-trimethylpsoralen (288 mg, 0.678 mmol) and sodium azide (88.2 mg, 1.36 mmol) were refluxed in 3 mL of 95% ethyl alcohol for 8 hours. The reaction solution was let cool and cold water (50 mL) was added. The water layer was poured away. The crude material was purified by chromatography on (Silica gel with chloroform eluent) a Chromatotron (Harrison Research, Inc., Palo Alto, Calif.) and vacuum dried to give a light yellow syrup, 4'-(7-Azido-2,5-oxa) heptyl-4,5',8-trimethylpsoralen, (123 mg, 49%). NMR δ 2.50 (s, 6H), 2.57 (s, 3H), 3.39 (t, J=5.2 Hz, 2H), 3.68 (m, 6H), 4.70 (s, H), 6.24 (s, 1H), 7.62 (s, 1H)
STEP 4: 4'-(7-Azido-2,5-oxa)heptyl-4,5=,8-trimethylpsoralen (122 mg, 0.33 mmol), triphenylphosphine (129 mg, 0.49 mmol) and several drops of water were dissolved in tetrahydrofuran (2 mL). The light yellow clear solution was stirred at room temperature over a weekend; no starting material was detected by TLC. The reaction solution was concentrated and the residue was dissolved in CHCl$_3$ (20 mL). The solution was extracted with 0.15 N aqueous HCl solution (10 mL then 2×5 mL) and the HCl layers was taken to pH 13 by addition of 20% aqueous NaOH solution. The basic solution was extracted with CHCl$_3$ (3×15 mL). The combined CHCl$_3$ layers were washed with water, dried over anhydrous $Na_2SO_4$, concentrated, and vacuum dried to give 63.9 mg of product, 4'-(7-amino-2,5-oxa)heptyl-4,5',8-trimethylpsoralen, (56%). TLC showed only one spot. NMR δ 2.50 (s, 3H); 2.50 (s, 3H); 2.57 (s, 3H); 2.86 (t, J=5.3 Hz, 2H); 3.50 (t, J=5.3 Hz, 2H); 3.63 (s, 4H); 4.70 (s, 2H); 6.24 (s, 1H); 7.62 (s, 1H). m.p. 170°–173° C.

The solid was dissolved in absolute ethanol, then 1M HCl in ethyl ether was added, the suspension was filtered and the product rinsed with ether and dried.

EXAMPLE 7

Synthesis of 4'-(12-amino-8-aza-2,5-dioxa)dodecyl-4,5',8-trimethylpsoralen Dihydrochloride (Compound 8)

The synthesis of 4'-(12-amino-8-aza-2,5-dioxa)dodecyl-4,5',8-trimethylpsoralen dihydrochloride proceeds in one (1) step from the product of Example 5, method 2, step 2: A solution of 4'-(7-methanesulfonyloxy-2,5-oxa)heptyl-4,5',8-trimethylpsoralen (108 mg, 0.253 mmol) in 8 mL of acetonitrile was slowly added to a solution of 1,4-diaminobutane (132 mg, 1.49 mmol) in 2.8 mL of acetonitrile. After refluxing for 8 hours, no starting material remained by TLC. The reaction mixture was cooled to room temperature and CHCl$_3$ (25 mL) and 1N aqueous NaOH (25 mL) solution were added. The layers were separated and CHCl$_3$ (2×10 mL) was used to wash the aqueous layer. Aqueous HCl (0.3 N, 3×10 mL) was used to extract the product from the combined organics layers. The HCl layers was treated with 20% aqueous NaOH solution until pH 13. The combined basic layers were then extracted with CHCl$_3$ (3×20 mL). The CHCl$_3$ layer was washed with saturated NaCl aqueous solution (10 mL) then dried over anhydrous $Na_2SO_4$. After concentration and vacuum drying, 63 mg of product, 4'-(12-amino-8-aza-2,5-dioxa)dodecyl-4,5',8-trimethylpsoralen dihydrochloride, was obtained (60%). NMR δ 1.45 (m, 2H), 2.49 (s, 6H), 2.55 (s, 3H), 2.58 (t, 2H), 2.66 (t, J=5.6 Hz, 2H), 2.76 (m, 4H), 3.55–3.61 (m, 6H), 4.68 (s, 2H), 6.22 (s, 1H), 7.61 (s, 1H).

EXAMPLE 8

Synthesis of 4'-(2-aminoethyl)-4,5',8-trimethylpsoralen Hydrochloride (Compound 3)

The synthesis of 4'-(2-aminoethyl)-4,5',8-trimethylpsoralen proceeds in one (1) step: sodium trifluoroacetoxyborohydride was made by adding trifluoroacetic acid (296 mg, 2.60 mmol) in 2 mL of THF to a stirred suspension of sodium borohydride (175 mg, 4.63 mmol) in 2 mL of THF over a period of 10 minutes at room temperature. The resultant suspension was added to a suspension of 4'-cyanomethyl-4,5',8-trimethylpsoralen (Kaufman et al., J. Heterocyclic Chem. 19:1051 (1982)) (188 mg, 0.703 mmol) in 2 mL of THF. The mixture was stirred overnight at room temperature. Several drops of water were added to the reacted light yellow clear solution to decompose the excess reagent under 10° C. The resulting mixture was concentrated and 1N aqueous NaOH solution (30 mL) was added. Chloroform (30 mL then 10 mL, 5 mL)) was used to extract the resultant amine. Combined $CHCl_3$ layers were washed with saturated NaCl solution. The amine was then extracted into aqueous 0.3N HCl (10, 5, 5 mL) and the acid layers were taken to pH 13 with 20% aqueous NaOH. $CHCl_3$ (3×10 mL) was used to extract the amine from the combined base layers then washed with water (2 mL) and dried over anhydrous $Na_2SO_4$. Upon concentration and vacuum drying the amine was obtained as a solid, >95% pure by NMR. NMR δ 2.45 (s, 3H); 2.47 (s, 3H); 2.53 (s, 3H); 2.78 (t, J=6.6 Hz, 2H); 3.00 (t, J=6.5 Hz, 2H); 6.20 (s, 1H); 7.44 (s, 1H). The solid was dissolved in absolute ethanol. A solution of hydrogen chloride in diethyl ether (1N, 1 mL) was added. The suspension was filtered to obtain compound 3, a light purple solid (32.7 mg, yield 15%), m.p. >237° C. (decomp.)

EXAMPLE 9

4'-(6-Amino-2-aza)hexyl-4,5',8-trimethylpsoralen Dihydrochloride (Compound 6)

The synthesis of 4'-(6-amino-2-aza)hexyl-4,5',8-trimethylpsoralen dihydrochloride proceeds in one (1) step, as follows: a solution of 4'-chloromethyl-4,5',8-trimethylpsoralen (188 mg, 0.68 mmol) in 30 mL of acetonitrile was added to a solution of 1,4-diaminobutane (120 mg, 1.4 mmol) in 7 mL of acetonitrile. After stirring overnight the solvent was removed under reduced pressure. Chloroform (10 mL) and 1N NaOH (10 mL) were added to the residue and the mixture was shaken and separated. The aqueous solution was extracted with a further 2×10 mL of $CHCl_3$ and the combined extracts were rinsed with water. The product was then extracted from the $CHCl_3$ solution with 0.3N aqueous HCl and the acidic layer was then taken to pH 12 with concentrated NaOH solution. The base suspension was extracted with $CHCl_3$ which was then rinsed with water, dried over $Na_2SO_4$ and concentrated under reduced pressure to give the amine as the free base; NMR ($CDCl_3$); a 1.33 (m, 3H), 1.52 (m, 4H), 2.47 (s, 3H), 2.49 (d, J=1.1 Hz, 3H), 2.54 (s, 3H), 2.68 (q, J=6.5 Hz, 4H), 3.86 (s, 2H), 6.21 (apparent d, J=1.1 Hz, 1H), 7.60 (s, 1H).

The free base, dissolved in about 6 mL of absolute EtOH was treated with a solution of HCl in ether (1.0M, 3 mL). The resultant HCl salt was filtered, rinsed with absolute EtOH and dried under vacuum to yield 150 mg of compound 6, (55%), m.p. 290° C. (decomposed). Analysis calculated for $C_{19}H_{26}C_{12}N_2O_3·H_2O$: C, 54.42; H, 6.73; N, 6.68. Found: C, 54.08; H, 6.45; N, 6.65.

The following compounds were prepared in a similar manner, with the differences in synthesis noted:

a) 4'-(4-amino-2-aza)butyl-4,5',8-trimethylpsoralen dihydrochloride (Compound 1), mp 320°–322° C. (decomp). In this synthesis ethylene diamine was used as the diamine.

b) 4'-(5-amino-2-aza)pentyl-4,5',8-trimethylpsoralen dihydrochloride (Compound 5), mp 288° C. (decomp). NMR of free base: δ 1.33 (br s, 3H), 1.66 (pent, J=6.8 Hz, 2H), 2.47 (s, 3H), 2.50 (d, J=1 Hz, 3H), 2.55 (s, 3H), 2.6–2.85 (m, 4H), 3.89 (s, 2H), 6.22 (apparent d, J=1 Hz, 1H), 7.62 (s, 1H). For this synthesis, 1,3-diaminopropane was used as the diamine.

c) 4'-(7-amino-2-aza)heptyl-4,5',8-trimethylpsoralen dihydrochloride (Compound 10), mp 300° C. (decomp). NMR of free base: δ 1.22 (br s,), 1.3–1.6 (m) total 9H, 2.44 (s), 2.50 (s), total 9H, 2.63 (m, 4H), 6.17 (s, 1H), 7.56 (s, 1H). Here, 1,5-diaminopentane was used as the diamine.

EXAMPLE 10

5'-(6-Amino-2-aza )hexyl-4,4',8-trimethylpsoralen Dihydrochloride (Compound-17)

The synthesis of 5'-(6-amino-2-aza)hexyl-4,4',8-trimethylpsoralen dihydrochloride proceeds in one (1) step, as follows: a suspension of 5'-chloromethyl-4,4',8-trimethylpsoralen (190 mg, 0.68 mmol) in 30 mL of acetonitrile was added to a solution of 1,4-diaminobutane (120 mg, 1.4 mmol) in 7 mL of acetonitrile. After stirring at room temperature overnight, the solvent was removed under reduced pressure. Chloroform (10 mL) and 1N NaOH (10 mL) were added to the residue and the mixture was shaken and separated. The aqueous layer was extracted with a further 2×10 mL of $CHCl_3$ and the combined extracts were rinsed with water. The product was then extracted from the $CHCl_3$ solution with 0.3N aqueous HCl and the acidic layer was then taken to approximately pH 12 with concentrated NaOH solution. The base suspension was extracted with $CHCl_3$ which was then rinsed with water, dried over $Na_2SO_4$ and concentrated under reduced pressure.

The residue was purified by column chromatography on silica gel with $CHCl_3$:EtOH:$Et_3$N (9:1:0.25). The fractions containing the product were combined and stripped of the solvent to give the free amine. NMR ($CDCl_3$): δ 1.35 (m, 3H); 1.49 (m, 4H); 2.22 (s, 3H); 2.46 (d, J=1.1 Hz, 3H); 2.51 (S, 3H); 2.65 (m, 4H); 3.88 (s, 2H); 6.17 (apparent d, 1Hz); 7.40 (s, 1H).

The free base, dissolved in absolute EtOH (~6 mL) was treated with a solution of HCl in ether (1.0M,~3 mL). The resultant HCl salt was filtered, rinsed with absolute EtOH and dried under vacuum to yield 100 mg (36.3%) of product, 5'-(6-Amino-2-aza)hexyl-4,4',8-trimethylpsoralen dihydrochloride, m.p. 288° C. (decomposed).

5'-(4-Amino-2-aza )butyl-4,4',8-trimethylpsoralen dihydro chloride (Compound 16) was prepared in the same manner, except that ethylene diamine was used as the diamine. NMR of free base: δ 1.83 (br s, 3H), 2.27 (s, 3H), 2.51 (s, H), 2.58 (s, 3H), 2.74 (m, 2H), 2.87 (m, 2H), 3.95 (s, 2H), 6.24 (s, 1H), 7.46 (s, 1H).

EXAMPLE 11

4'-(14-Amino-2,6,11-triaza)tetradecyl-4,5',8-trimethylpsoralen Tetrahydrochloride (Compound 15)

The synthesis of 4'-(14-amino-2,6,11-triaza)tetradecyl-4,5',8-trimethylpsoralen tetrahydrochloride proceeds in one (1) step, as follows. To a solution of 0.5 g (2.5 mmol) of spermine (Aldrich, Milwaukee, Wis.) in 10 ml of methanol was added a 5N methanolic solution of HCl (concentrated HCl diluted with MeOH to 5N) to adjust to pH 5–6, followed by 0.128 g (0.5 mmol) of 4,5',8-trimethylpsoralen-4'carboxaldehyde, 20 mg (0.3 mmol) of $NaBH_3CN$ and 3 mL of MeOH. The reaction mixture was stirred at room temperature overnight. A solution of 5N methanolic HCl was added until pH<2 and methanol was removed under reduced pressure. The residue was taken up in about 100 mL of water and rinsed with three 25 mL portions of $CHCl_3$. The aqueous solution was brought to pH>10 with concentrated NaOH and extracted with three 25 mL portions of $CHCl_3$.

These final extracts were combined and washed with water, dried (Na$_2$SO$_4$) and evaporated to give the free base of the amine, ≧95% pure by NMR. NMR (CDCl$_3$): δ 1.31 (m, 5H), 1.45 (pent, J=3.41 Hz, 4H), 1.65 (m, 4H), 2.46 (s, 3H), 2.49 (d, J=1.14 Hz, 3H), 2.66 (m, 15 H), 3.85 (s, 2H), 6.21 (s, 1H)m 7.60 (s, 1H).

The free amine was dissolved in absolute ethanol and HCl (anhydrous, 1N in ethyl ether) was added. The hydrochloride salt was filtered and washed with absolute ethanol and dried under vacuum at room temperature giving 80.2 mg of product, 4'-(14-amino-2,6,11-triaza)tetradecyl-4,5',8-trimethylpsoralen tetrahydrochloride, as a light yellow solid.

EXAMPLE 12

An r-17 bacteriophage assay was used in this example to predict pathogen inactivation efficiency and to determine nucleic acid binding of the photoreactive binding compounds of the present invention. In the r-17 assay, the bacteriophage was placed in a solution with each compound tested and was then irradiated. The ability of the phage to subsequently infect bacteria and inhibit their growth was measured. The bacteriophage was selected for its relatively accessible nucleic acid such that the culture growth inhibition would accurately reflect nucleic acid damage by the test compounds. The bacteriophage assay for nucleic acid binding to test compounds offers a safe and inexpensive procedure to identify compounds likely to display efficient pathogen inactivation. Previous experiments support that the r-17 assay accurately measures HIV-1 sensitivity to similar compounds.

The R17 was grown up in Hfr 3000 bacteria, approximate titer 5×10$^{11}$. (R17 and Hfr 3000 were obtained from American Tissue Culture Collection (ATCC), Washington, D.C.) The R17 phage stock was added to a solution of 15% fetal bovine serum in Dulbecco's Modified Eagles Medium (DMEM) to a final phage concentration of 10$^9$/mL. An aliquot (0.5 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at concentrations between 4 µM and 320 µM. (AMT is commercially available from HRI, Inc., Concord, Calif.; 8-MOP is commercially available from Sigma, St. Louis, Mo.). The tubes were placed in a light device as described in EXAMPLE 1 and irradiated for between 1 and 10 minutes. Sterile 13 mL dilution tubes were prepared; each test compound required one tube with 0.4 mL of Luria broth (LB) and five tubes containing 0.5 mL of LB broth. To make the dilutions, a 0.100 mL aliquot of the irradiated solution of phage and test compound was added to the first dilution tube of 0.4 mL of media then 0.020 mL of this solution was added to the second tube of 0.5 mL medium (1:25). The second solution was then diluted serially (1:25) into the remaining tubes. To each diluted sample was added 0.050 mL of Hfr 3000 bacteria cultured overnight and 3 mL of molten LB top agar and the mixed materials were poured onto LB broth plates. After the top agar hardened, the plates were incubated at 37° C. overnight. The plaque forming units were then counted the following morning and the titer of the phage remaining after phototreatment was calculated based on the dilution factors.

The following controls were run: the "phage only" in which phage was not treated with test compound and not irradiated (listed as "starting titer" in the tables below); the "UV only" in which the phage was irradiated in the absence of test compound; and the "dark" control in which the phage/test compound solution was not irradiated before it was diluted and plated.

TABLE 5, below, shows three different experiments which tested Compound 1 according to the R17 protocol just described. A comparison of values for the control samples in runs 1–3 (values in bold) shows that neither the "UV only" nor the "dark" controls result in significant bacterial kill (at most, 0.3 logs killed in the "UV only" control and 0.1 logs killed in the "dark" control).

The "UV only" control was repeated in many similar experiments with other compounds of the present invention and consistently showed no significant kill. (Data not shown). Thus, the "UV only" control is not shown in the tables and figures that follow, although it was performed in every experiment in this example. As for the "dark" control, after many trials with various compounds of the present invention, it became apparent that regardless of the type of substitution on the 4' position of the psoralen, no experimentally significant bacterial inactivation was observed in the dark. (Data not shown). For example, in Table 5, experiment 1 shows 0.1 logs kill with compound 1 in the dark. In contrast, when Compound 1 is irradiated for just 1 minute, the resulting drop in titer is >6.7 logs. Therefore, "dark" controls were not run for the later tested compounds and where run, are not shown in the tables and figures that follow.

TABLE 5

| EXPERIMENT # | TREATMENT | LOG TITER | LOGS KILLED |
|---|---|---|---|
| 1 | phage only | 7.7 | — |
|  | uva only (10') | 7.4 | 0.3 |
|  | compound only (32 µM) | 7.6 | 0.1 |
|  | 32 µM cmpd 1' uva | <1 | >6.7 |
|  | 32 µM cmpd 10' uva | <1 | >6.7 |
| 2 | phage only | 7.8 | — |
|  | uva only (10') | 7.6 | 0.2 |
|  | compound only (3.2 µM) | 7.7 | 0.1 |
|  | 3.2 µM cmpd 1' uva | 6.9 | 0.9 |
|  | 3.2 µM cmpd 10' uva | 6.1 | 1.7 |
| 3 | phage only | 7.3 | — |
|  | uva only (1') | 7.3 | 0 |
|  | compound only (16 µM) | 7.3 | 0 |
|  | 4 µM cmpd 1' uva | 6.3 | 1.0 |
|  | 8 µM cmpd 1' uva | 5.6 | 1.7 |
|  | 16 µM cmpd 1' uva | 3.9 | 3.4 |

Figure 6:
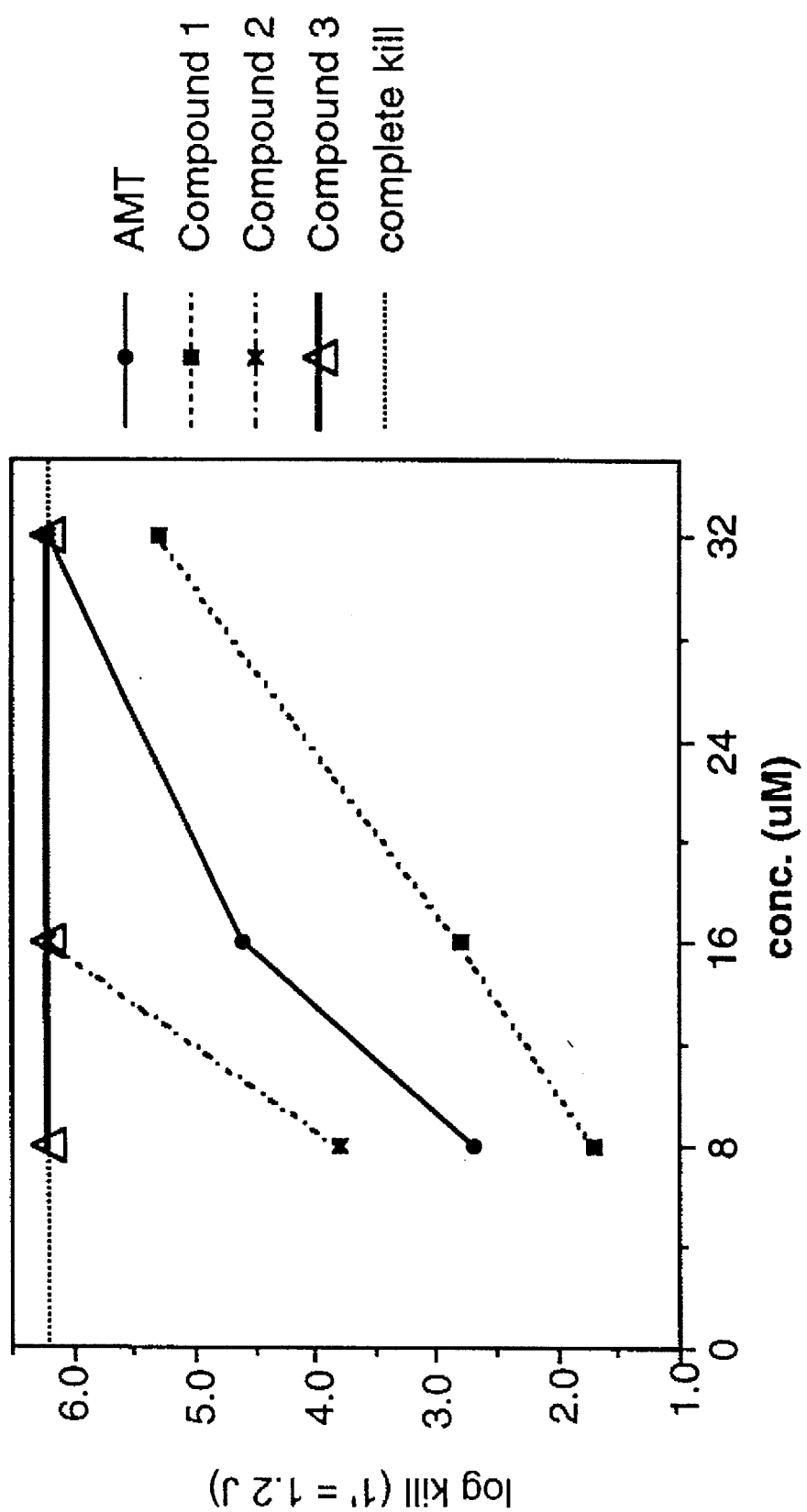
FIG. 6 shows the impact of concentration on the log kill of R17 when Compounds 1–3 of the present invention are photoactivated.
Figure 7:
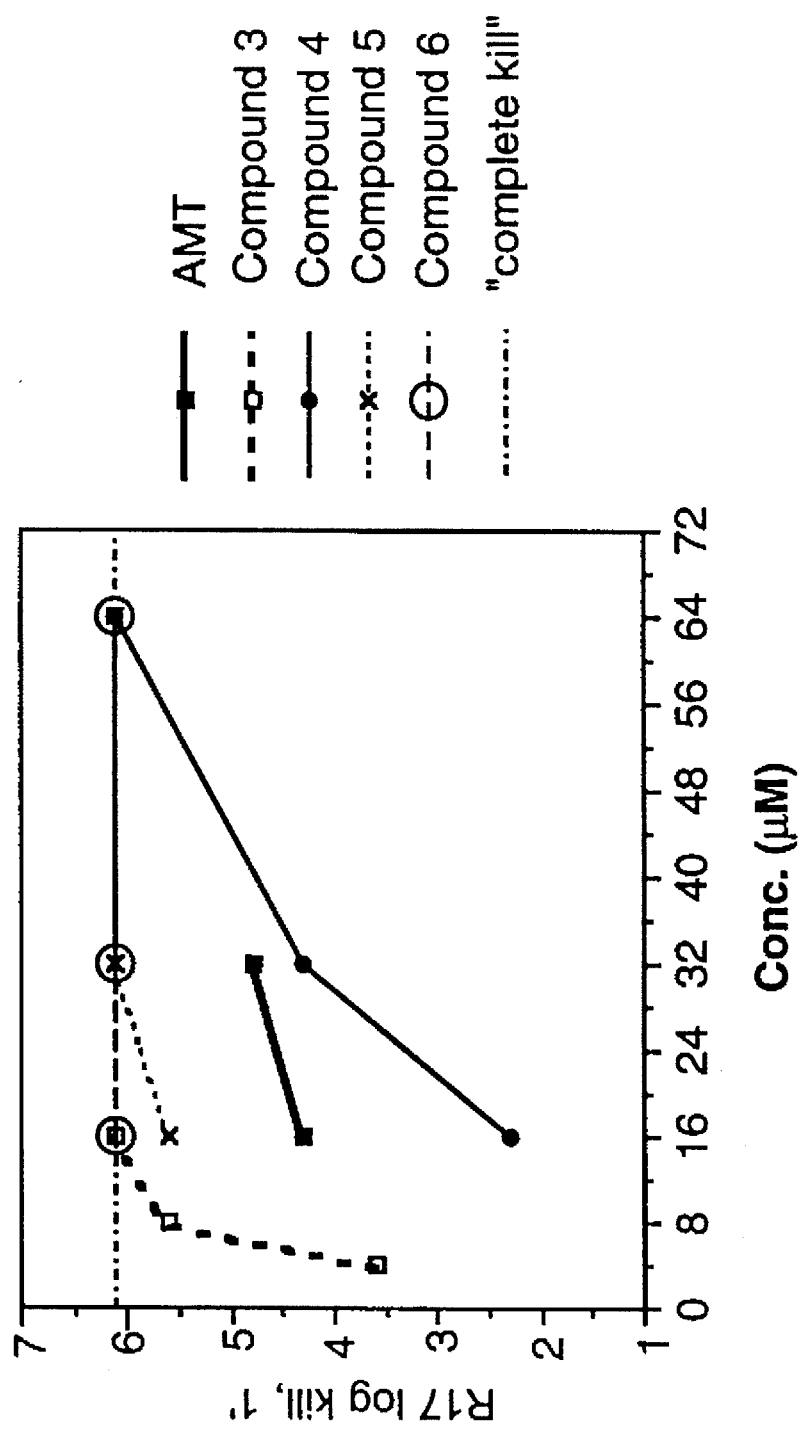
FIG. 7 shows the impact of concentration on the log kill of R17 when Compounds 3–6 of the present invention are photoactivated.
Figure 8:
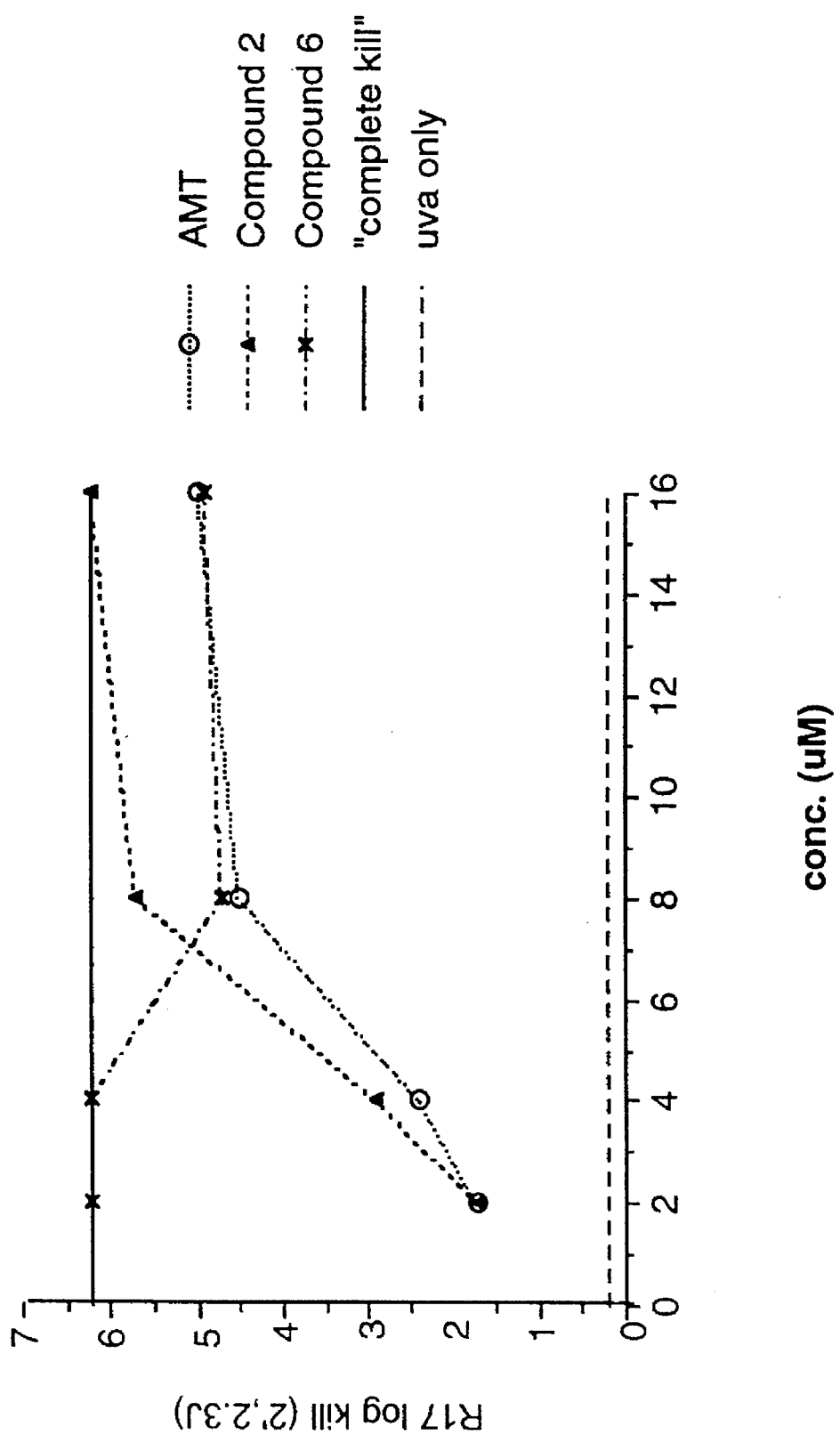
FIG. 8 shows the impact of concentration on the log kill of R17 when Compounds 2 and 6 of the present invention are photoactivated.
Figure 9:
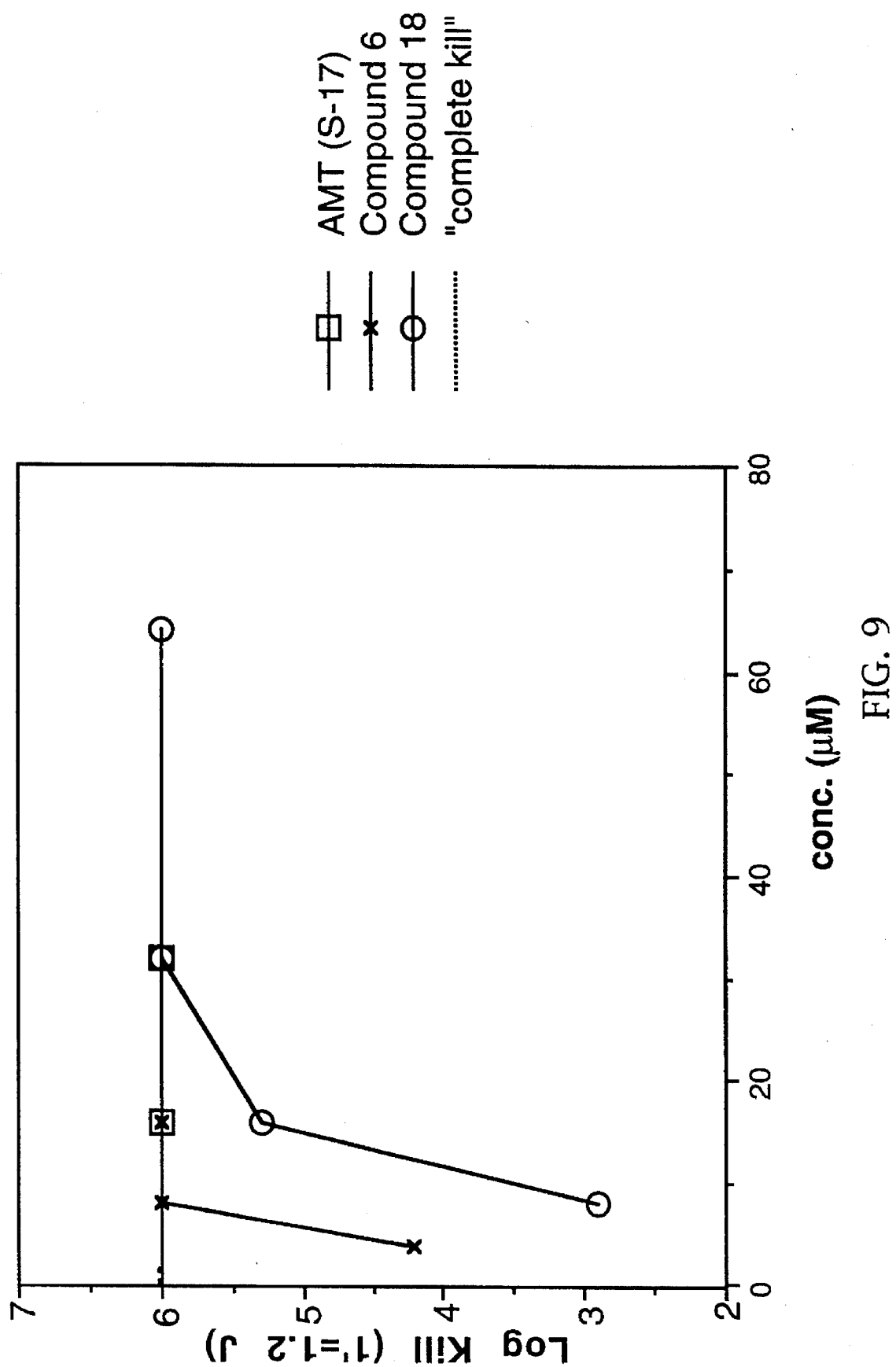
FIG. 9 shows the impact of concentration on the log kill of R17 when Compounds 6 and 18 of the present invention are photoactivated.
Figure 10:
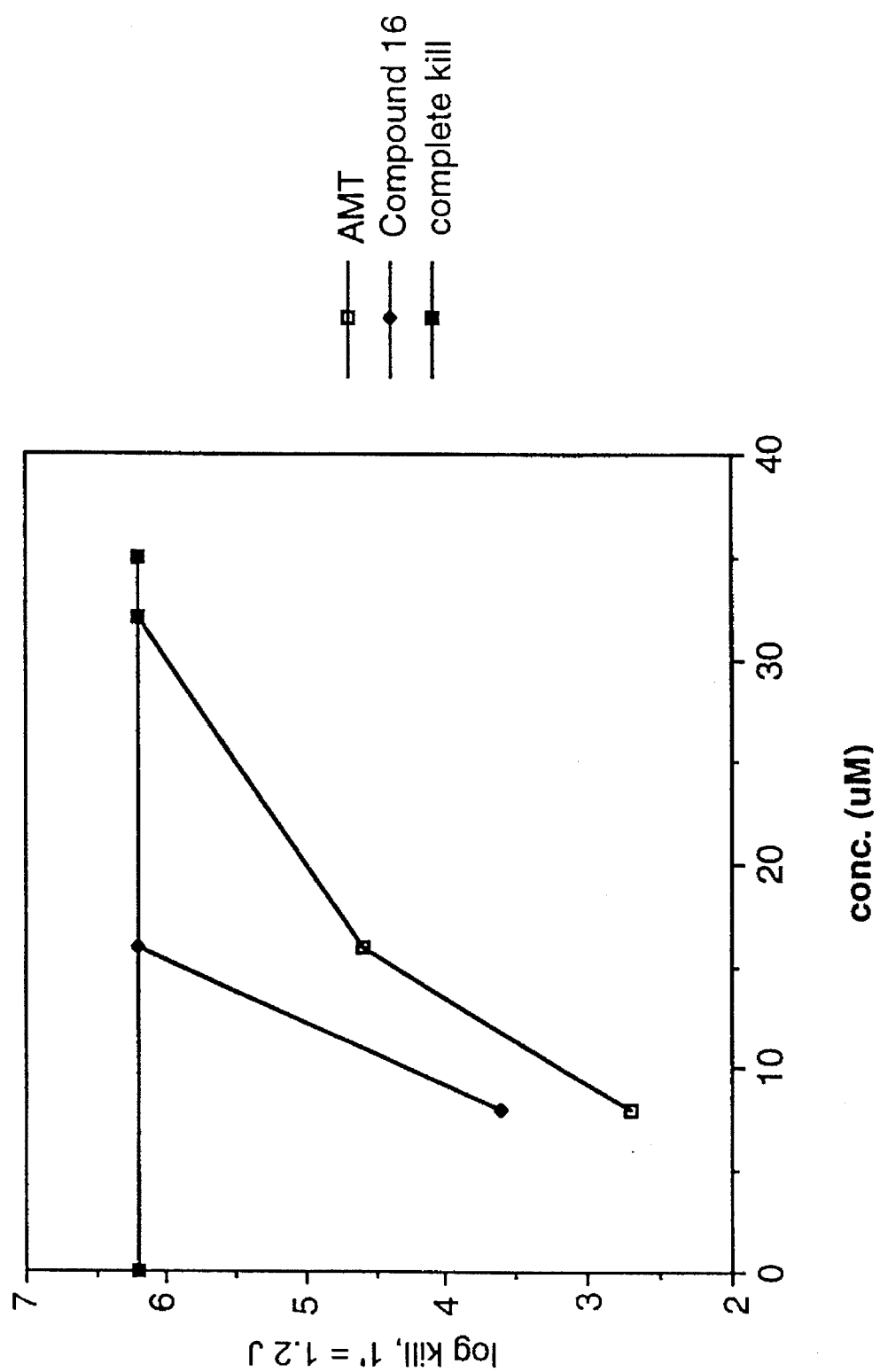
FIG. 10 shows the impact of concentration on the log kill of R17 when Compound 16 of the present invention is photoactivated.
Figure 11:
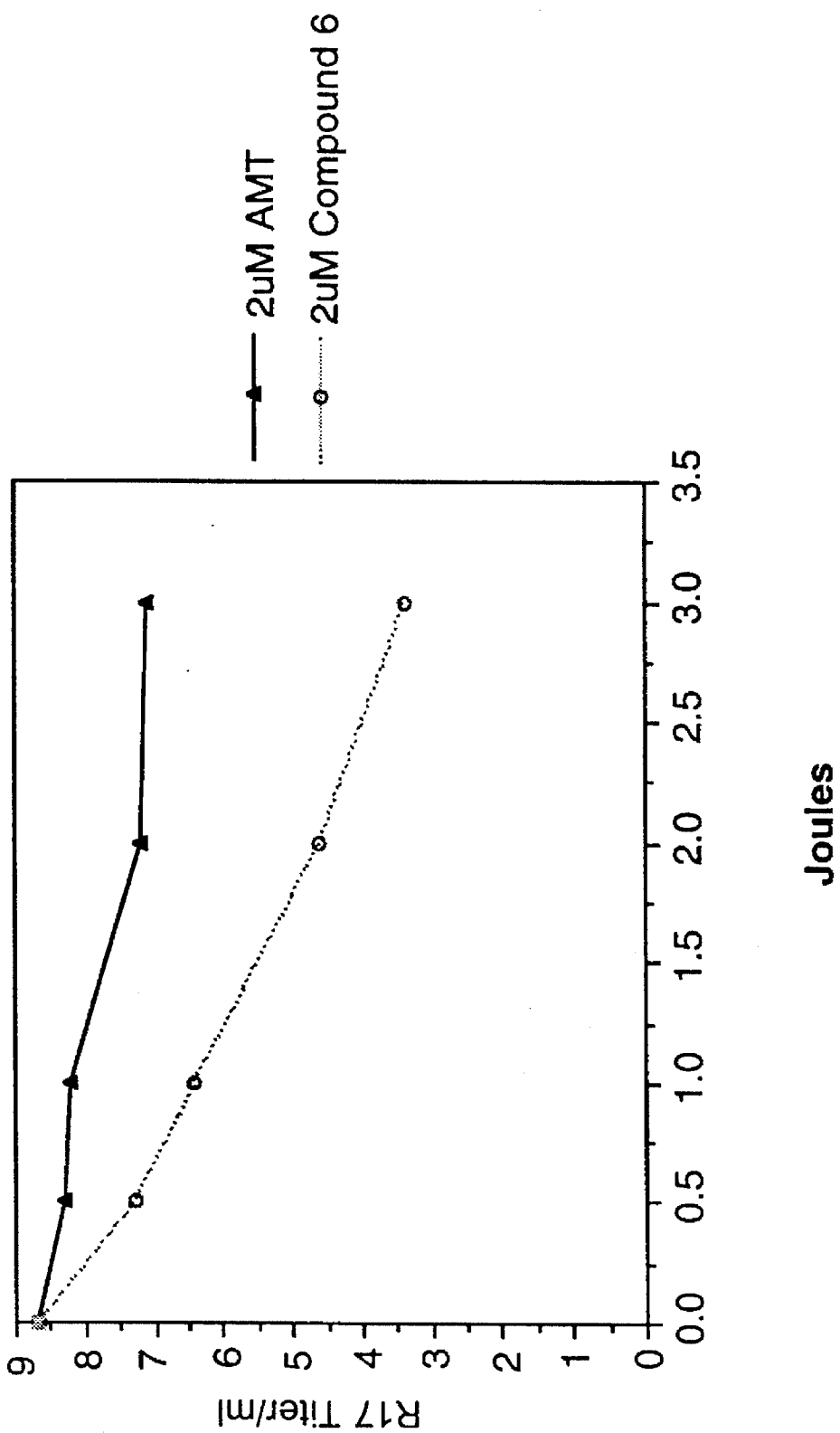
FIG. 11 shows the impact of varying Joules/cm$^2$ (Watt second/cm$^2$) of irradiation on the log titer of R17 for Compound 6 of the present invention.
Figure 12:
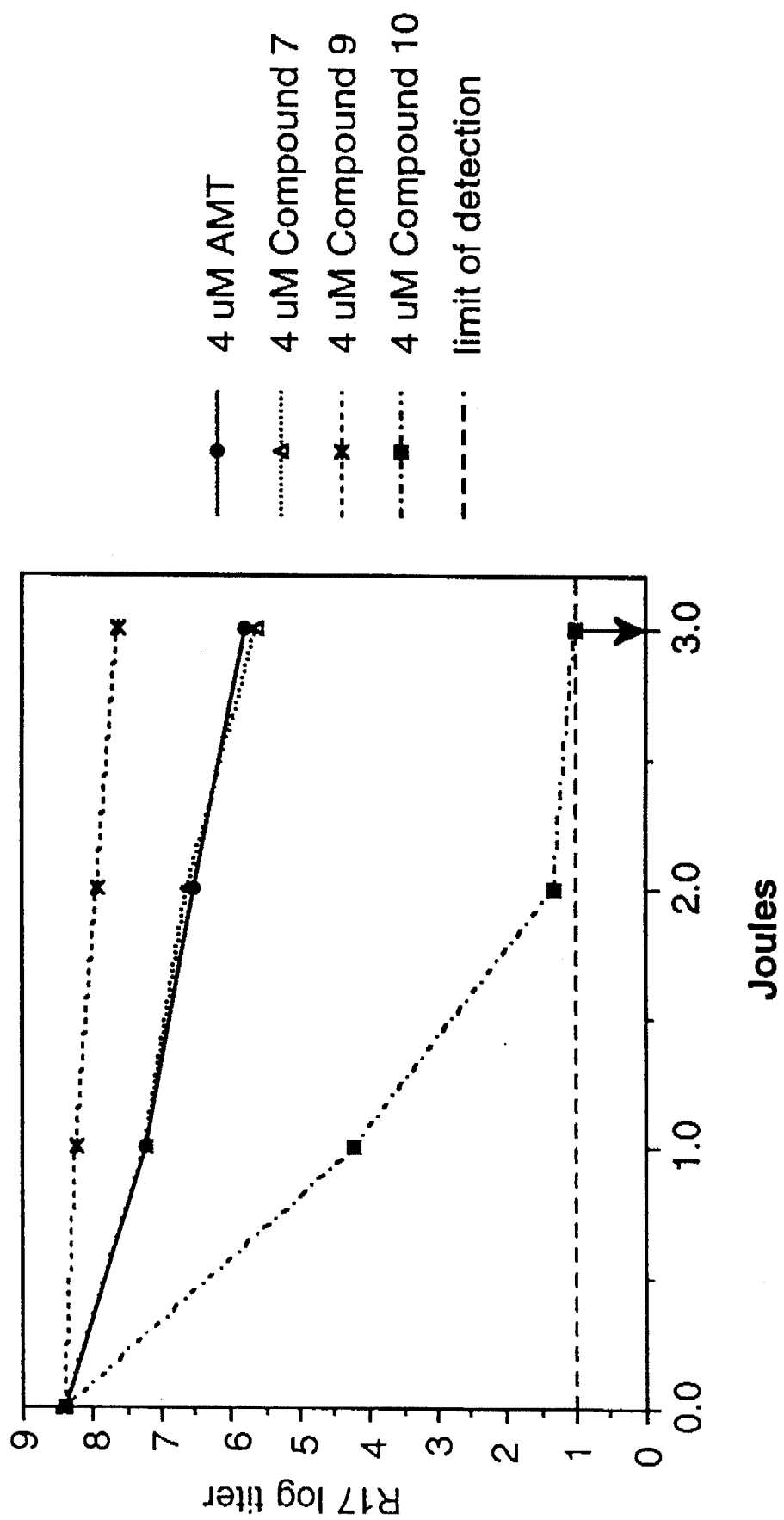
FIG. 12 shows the impact of varying Joule/cm$^2$ of irradiation on the log titer of R17 for Compounds 7, 9 and 10 of the present invention.
Figure 13:
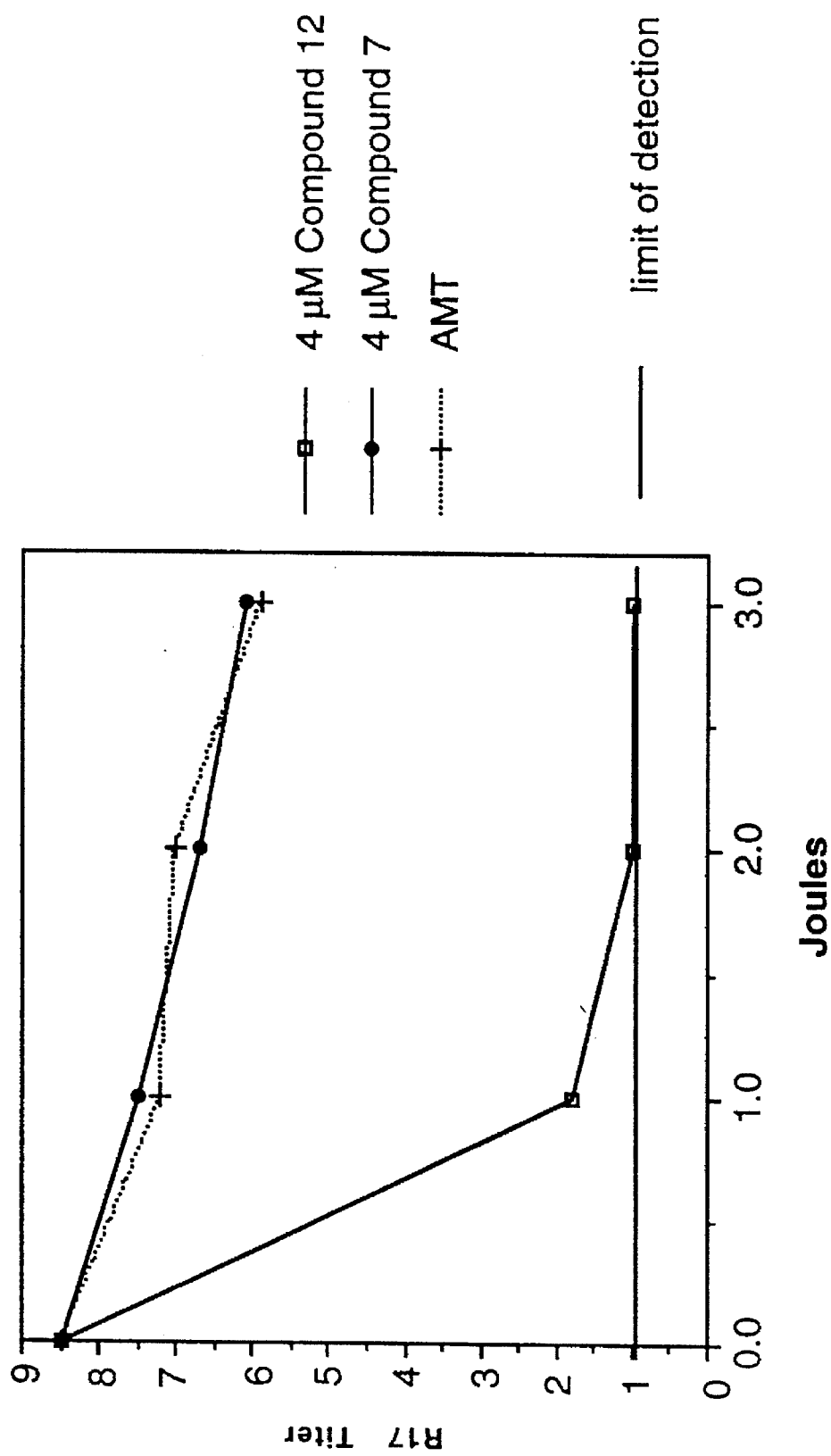
FIG. 13 shows the impact of varying Joules/cm$^2$ of irradiation on the log titer of R17 for Compounds 7 and 12 of the present invention.
Figure 14:
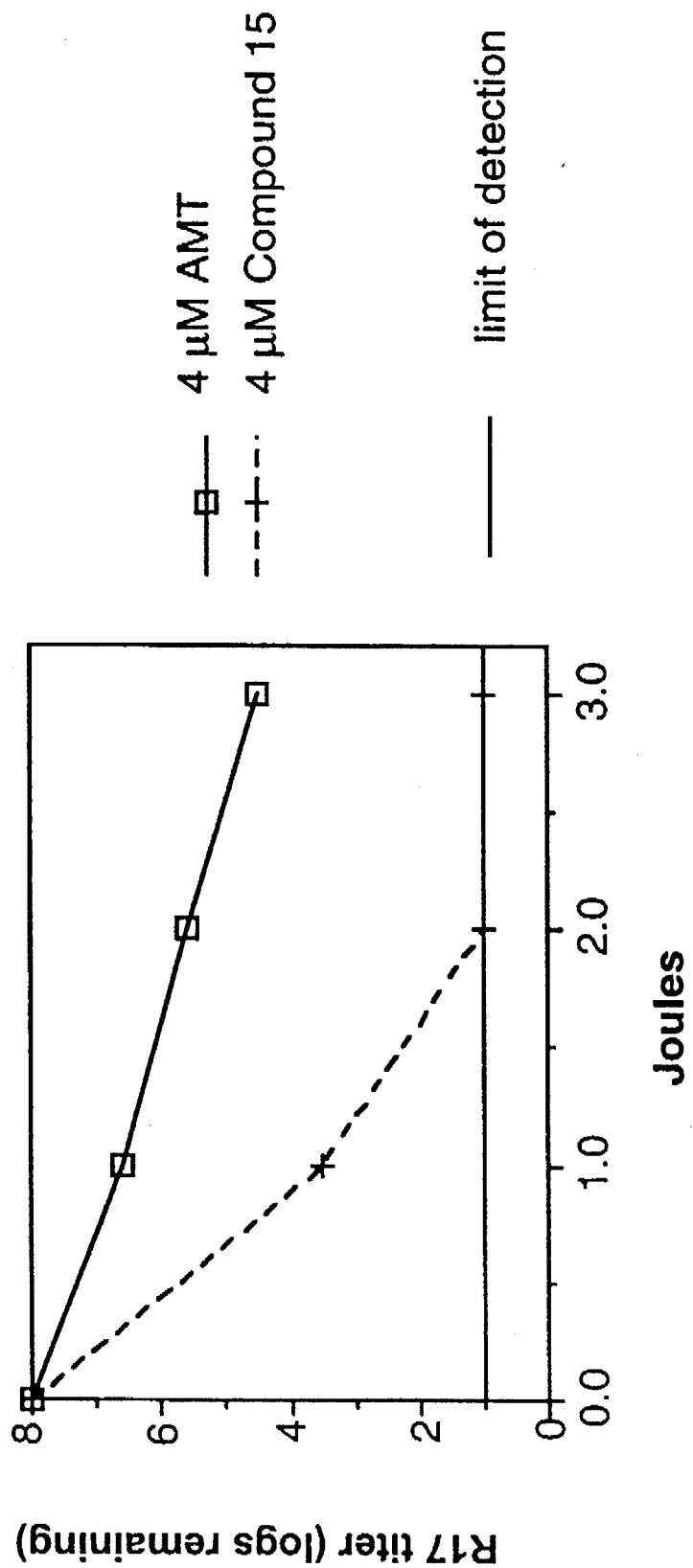
FIG. 14 shows the impact of varying Joules/cm$^2$ of irradiation on the log titer of R17 for Compound 15 of the present invention.
Figure 15:
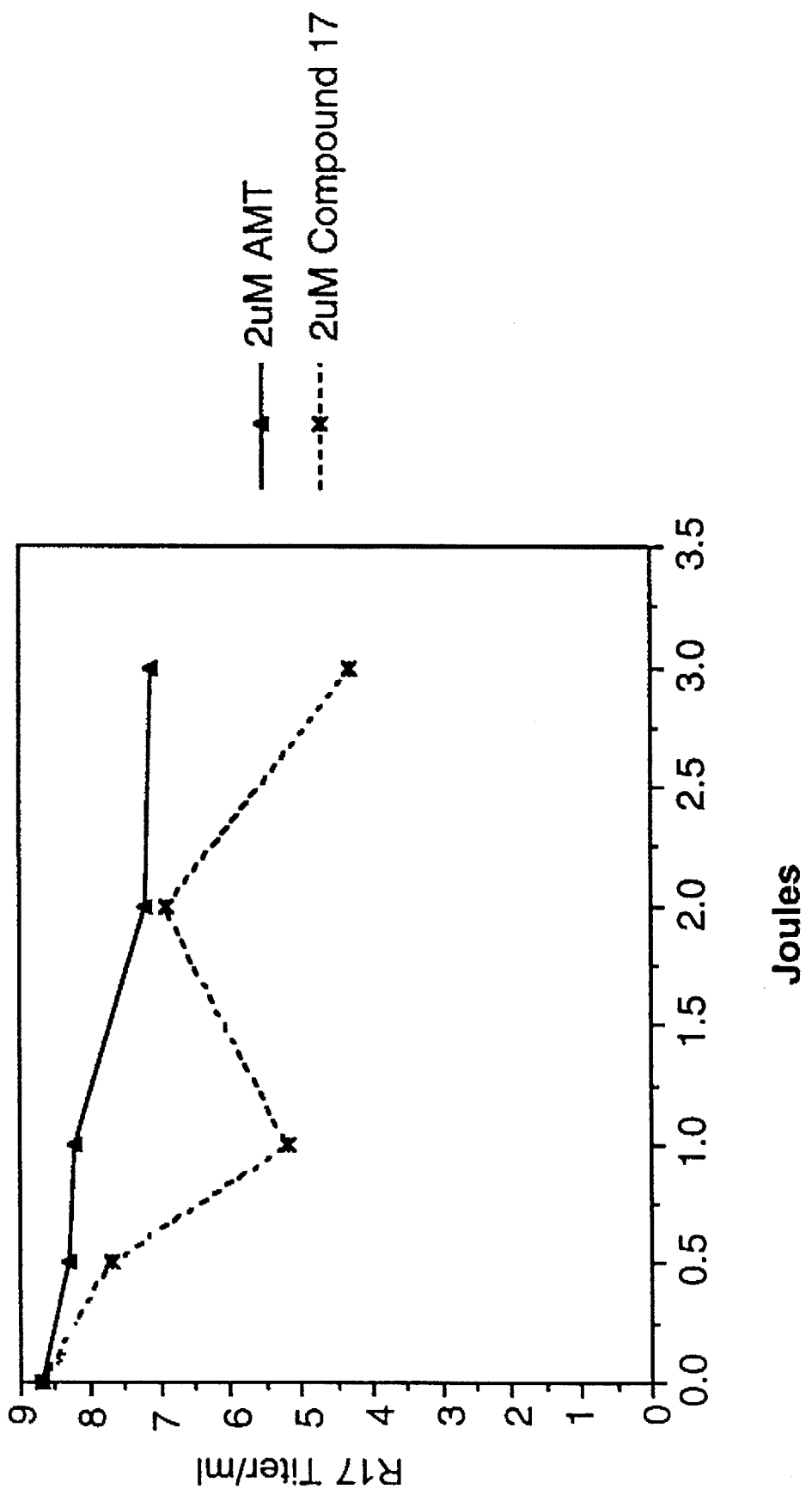
FIG. 15 shows the impact of varying Joules/cm$^2$ of irradiation on the log titer of R17 for Compound 17 of the present invention.
Figure 16:
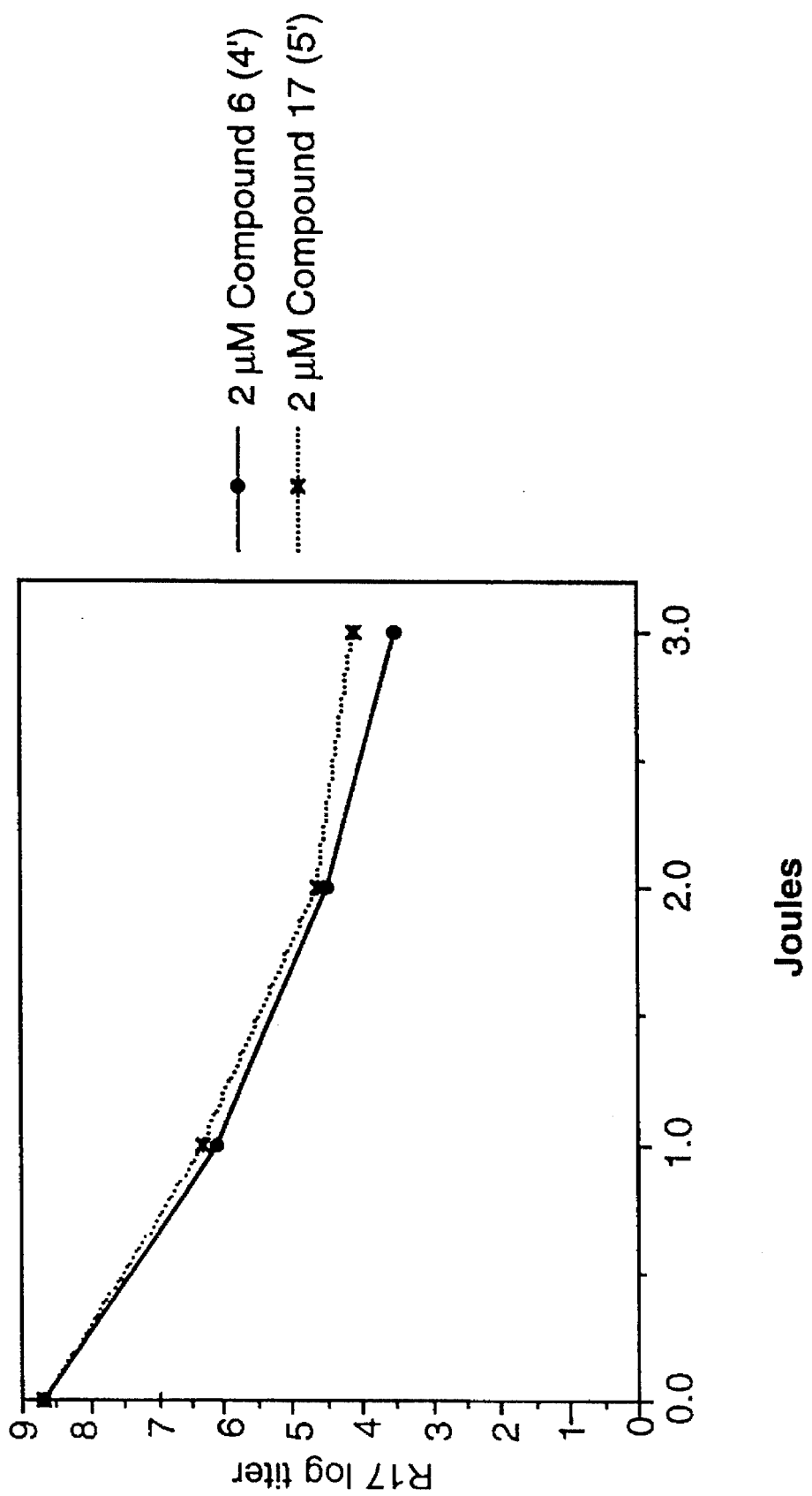
FIG. 16 shows the impact of varying Joules/cm$^2$ of irradiation on the log titer of R17 for Compounds 6 and 17 of the present invention.
Figure 17:
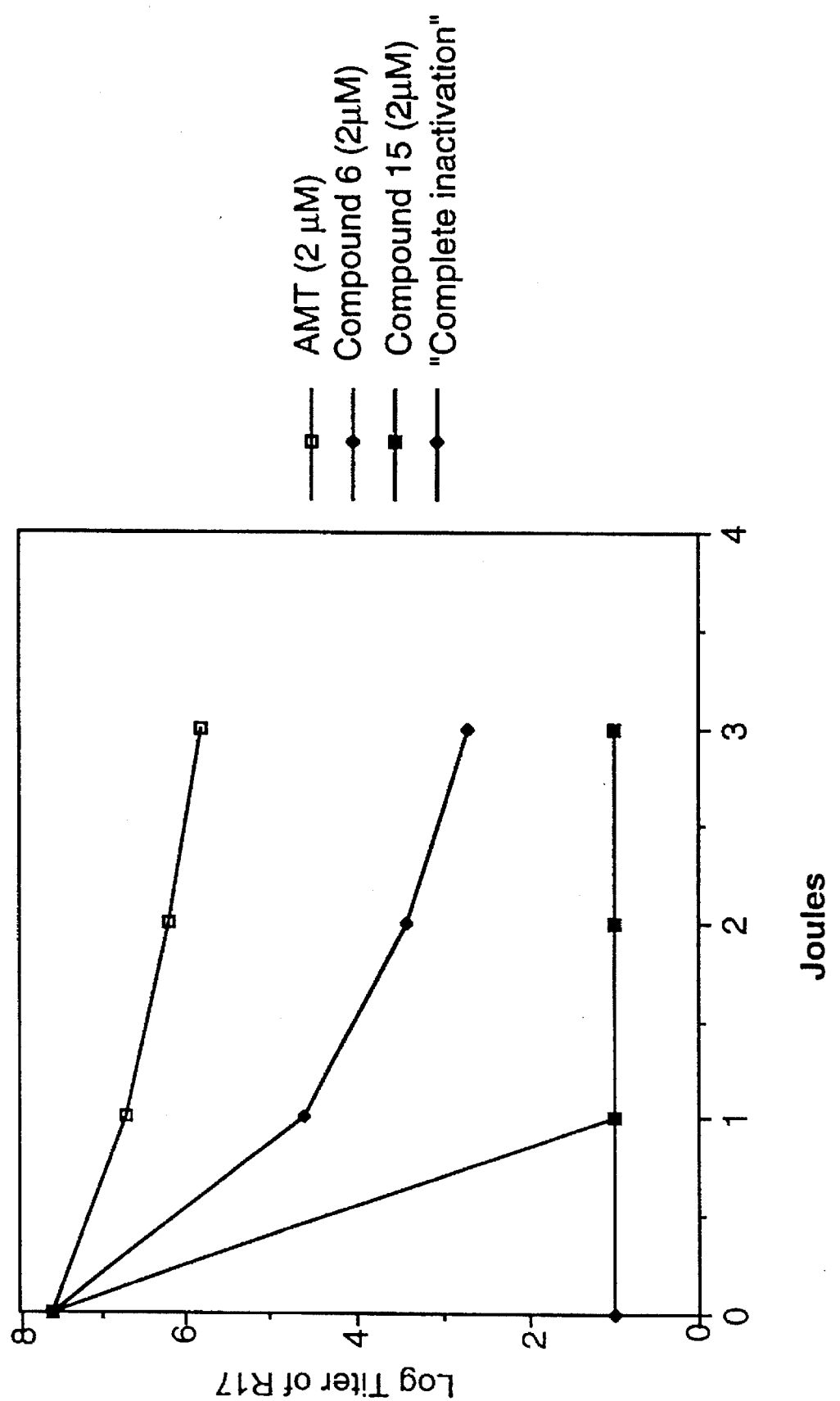
FIG. 17 shows the impact of varying Joules/cm$^2$ of irradiation on the log titer of R17 for Compounds 6 and 15 of the present invention.

Tables 6–9, below, and FIGS. 6–8 show the results of the R17 assay for several of the 4'-primaryamino-substituted psoralen compounds of the present invention. The data in Tables 7 and 8 appears in FIGS. 6 and 7, respectively. 5'-Primaryamino-substituted psoralen compounds of the present invention, which have substitutions on the 5' position similar to the 4'-primaryamino-substituted psoralen compounds, were also tested at varying concentration, as described above in this example, and are shown to exhibit comparable inactivation efficiency. The results for these compounds are shown in FIGS. 9 and 10, below.

TABLE 6

Starting titer of R17: approx. 7.5 logs
1 Minute Irradiation

| Cmpd. | R17 log kill (32 μM) |
|---|---|
| AMT | >6.7 |
| 8-MOP | 0 |
| 1 | >6.6 |

TABLE 7

Starting titer approx. 7.2 logs R17
1 minute irradiation

| Compound | R17 8 μM | log 16 μM | kill 32 μM |
|---|---|---|---|
| AMT | 2.7 | 4.6 | >6.2 |
| 1 | 1.7 | 2.8 | 5.3 |
| 2 | 3.8 | >6.2 | >6.2 |
| 3 | >6.2 | >6.2 | >6.2 |

TABLE 8

Starting titer approx. 7.1 logs
1 minute irradiation = 1.2 J/cm²

| Cmpd. | R17 8 μM | log 16 μM | kill 32 μM | 64 μM |
|---|---|---|---|---|
| AMT | — | 4.5 | 4.8 | — |
| 3 | 5.6 | >6.1 | — | — |
| 4 | — | 2.3 | 4.3 | >6.1 |
| 5 | — | 5.6 | >6.1 | >6.1 |
| 6 | — | >6.1 | >6.1 | >6.1 |

TABLE 9

Starting titer approx. 7.1 logs R17.
1 Minute Irradiation.

| Cmpd. | 8 μM | R17 log 16 μM | kill 32 μM | 64 μM |
|---|---|---|---|---|
| AMT | — | >6 | >6 | — |
| 6 | >6 | >6 | — | — |
| 7 | — | >6 | >6 | >6 |

The compounds of the present invention having substitutions on the 4' position of the psoralen ring proved to be active in killing R17, as shown in the tables above. In Table 7, it is apparent that compound 1 of the present invention exhibits much higher R17 inactivation efficiency than does 8-MOP. As shown in Table 7 and FIG. 6, Compound 1 is one of the less active compounds of the present invention. Both Compounds 2 and 3 show higher log inactivation than Compound 1 at each concentration point. These results support that the compounds of the present invention are generally much more active than 8-MOP.

The compounds of the present invention also have similar or better R17 inactivation efficiency than AMT. In Tables 7 and 8, and FIGS. 6–10, all compounds of the present invention achieve R17 log inactivation at levels comparable to AMT. Compounds 2 and 3 (Table 6, FIG. 6), Compounds 5 and 6 (Table 8, FIG. 7), and Compound 16 (FIG. 10) exhibit significantly higher inactivation efficiency than does AMT.

Compounds of the present invention were also tested at a constant concentration for varying doses of UV light. Three sets of 1.5 mL tubes were prepared containing 0.6 mL aliquots of R17 in DMEM (prepared as described above). The compound tested was added at the desired concentration and the samples were vortexed. The samples were then irradiated at intervals of 1.0 J/cm², until 3.0 J/cm² was reached. Between each 1.0 J/cm² interval, 100 μL was removed from each sample and placed in the first corresponding dilution tube, then five sequential dilutions were performed for each compound tested, at all 3 irradiation doses, as described above in this example.

Then 50 μL of Hfr 3000 bacteria was added to each tube, 3 mL of top agar was added and the tube contents were vortexed. The contents of each tube was poured into its own LB plate and the plates were incubated overnight at 37° C. Plaques were counted by visual inspection the following morning.

The results of the assay for several 4' and 5'-primaryamino-substituted psoralen compounds are shown in FIGS. 11–17. This data further supports that the compounds of the present invention are comparable to AMT in their ability to inactivate R17. Further, Compounds 6 (FIG. 11), 10 (FIG. 12), 12 (FIG. 13), 15 (FIG. 14 and 17), and Compound 17 (FIG. 15), all were more efficient at inactivating R17 than was AMT.

EXAMPLE 13

Pathogen inactivation efficiency of several compounds of the present invention was evaluated by examining the ability of the compounds to inactivate cell-free virus (HIV). Inactivation of cell-free HIV was performed as follows.

As in the R17 assay, small aliquots of the compounds listed in TABLES 10 and 11, below, at the concentrations listed in the table, were added to stock HIV-1 to a total of 0.5 mL. The stock HIV (105–107 plaque forming units/mL) was in DMEM/15% FBS. The 0.5 mL test aliquots were placed in 24 well polystyrene tissue culture plates and irradiated with 320–400 nm (20 mW/cm²) for 1 min on a device similar to the device of Example 1. The photoactivation device used here was previously tested and found to result in light exposure comparable to the Device of Example 1. (Data not shown). Controls included HIV-1 stock only, HIV-1 plus UVA only, and HIV-1 plus the highest concentration of each psoralen tested, with no UVA. Post irradiation, all samples were stores frozen at −70° C. until assayed for infectivity by a microtiter plaque assay. Aliquots for measurement of residual HIV infectivity in the samples treated with a compound of the present invention were withdrawn and cultured.

Residual HIV infectivity was assayed using an MT-2 infectivity assay. (Previously described in Hanson, C. V., Crowford-Miksza, L. and Sheppard, H. W., J. Clin. Micro 28:2030 (1990)). The assay medium was 85% DMEM (with a high glucose concentration) containing 100 μg of streptomycin, 100 U of penicillin, 50 μg of gentamicin, and 1 μg of amphotericin B per mL, 15% FBS and 2 μg of Polybrene (Sigma Chemical Co., St. Louis, Mo.) per mL. Test and control samples from the inactivation procedure were diluted in 50% assay medium and 50% normal human pooled plasma. The samples were serially diluted directly in 96-well plates (Corning Glass Works, Corning, N.Y.). The plates were mixed on an oscillatory shaker for 30 seconds and incubated at 37° C. in a 5% CO₂ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.) and prewarmed to 38.5° C. was added to each well. The plates were kept at 37° C. for a few minutes until several plates had accumulated and then centrifuged in plate carriers at 600×g for 20 minutes in a centrifuge precooled to 10° C. In the centrifuge, cell monolayers formed prior to gelling of the agarose layer. The plates were incubated for 5 days at 37° C. in 5% $CO_2$ and stained by the addition of 0.05 mL of 50 µg/mL propidium iodide (Sigma Chemical Co.) in phosphate-buffered saline (pH 7.4) to each well. After 24 to 48 hours, the red fluorescence-stained microplaques were visualized by placing the plates on an 8,000 µW/cm$^2$ 304 nm UV light box (Fotodyne, Inc., New Berlin, Wis.). The plaques were counted at a magnification of ×20 to ×25 through a stereomicroscope. The results are shown in TABLES 10 and 11, below. "n" represents the number of runs for which the data point is an average.

The results support that the compounds of the present invention are effective in inactivating HIV. In fact, the data for concentrations of 64 µM of compound or higher suggests that compounds 2 and 3 are significantly more active than AMT, which was previously thought to be one of the most active anti-viral psoralens. At lower concentrations, Compound 6 is able to kill a higher log of HIV (3.1 logs at 32 µM) than is AMT (2.5 logs at 32 µM). The other compounds listed in TABLE 9 display inactivation efficiency in the same range as AMT.

TABLE 10

1 minute irradiation
HIV starting titer: approximately 5 logs

| COMPOUND | HIV log kill | | | |
|---|---|---|---|---|
| | 16 µM | 32 µM | 64 µM | 128 µM |
| AMT | 1.4 | 1.9–>3.6 | 3.9–>3.6 | >4.1 |
| 1 | — | — | 2.1 | >2.8 |
| 2 | 1.4 | 3.8 | >4.5 | >4.5 |
| 3 | — | 2.7 | >3.8 | >3.8 |
| 4 | — | 2.2 | >3.6 | >3.6 |
| 5 | 0.9 | 1.3 | >2.6 | — |
| 6 | 2.0 | 3.1 | >3.8 | — |
| 7 | 0.8 | 2.1 | 3.5 | — |
| 8 | 1.1 | 1.9 | 3.7 | >3.7 |

TABLE 11

HIV starting titer: approximately 5.4 logs
1 minute irradiation

| COMPOUND | HIV log kill | | |
|---|---|---|---|
| | 16 µM | 32 µM | 64 µM |
| 6 | 2.1 | 3.2 | >2.8 |
| 9 | 0.8 | 1.4 | 2.7 |
| 10 | 2.0 | >3.5 | >3.5 |
| 12 | 0.4 | 0.8 | 1.3 |
| 17 | 1.2 | 2.9 | 3.4 |
| 18 | 1.0 | 1.0 | 3.1 |

EXAMPLE 14

This example describes the protocol for inactivation of Duck Hepatitis B Virus (DHBV), a model for Hepatitis B Virus, using compounds of the present invention.

DHBV in duck yolk was added to platelet concentrate (PC) to a final concentration of $2 \times 10^7$ particles per mL and mixed by gentle rocking for $\geq 15$ min. Psoralens S-70, S-59 and AMT were added to 3 mL aliquots of PC in a Teflon™ mini-bag at concentrations of 35, 70, and 100 mM. Samples, including controls without added psoralen, were irradiated with 5J/CM$^2$ UVA, with mixing at 1 J/cm$^2$ increments. After irradiation, leukocytes and platelets were separated from virus by centrifugation. The supernatant containing DHBV was digested overnight with 50 µg/mL proteinase K in a buffer containing 0.5% sodium dodecyl sulphate, 20 mM Tris buffer, pH 8.0, and 5 mM EDTA at 55° C. Samples were extracted with phenol-chloroform and chloroform, followed by ethanol precipitation. Purified DNA was then used in PCR amplification reactions with a starting input of $10^6$ DHBV genomes from each sample. PCR amplicons were generated using primers pairs DCD03/DCD05 (127 bp), DCD03/DCD06 (327 bp) and DCD03/DCD07 (1072 bp). PCR was performed in a standard PCR buffer containing 0.2 mM each deoxyribonucleoside 5'-triphosphates (dATP, dGTP, dCTP, and dTTP), 0.5 mM each primer, and 0.5 units Taq polymerase per 100 ml reaction. 30 cycles of amplification were performed with the following thermal profile: 95° C. 30 sec, 60° C. 30 sec, 72° C. 1 min. The amplification was followed by a 7 min incubation at 72° C. to yield full length products. [lambda-$^{32}$P] dCTP was added at an amount of 10 mCi per 100 ml in order to detect and quantify the resulting products. Products were separated by electrophoresis on denaturing polyacrylamide slab gels and counted. The absence of signal in a given reaction was taken to indicate effective inactivation of DHBV.

The results showed that the smaller amplicons displayed increasing inactivation as a function of psoralen concentration for all psoralens tested. At the same concentrations, S-59 and S-70 inhibited PCR of the smaller amplicons better than did AMT. For the 1072 bp amplicon, complete inhibition of PCR was observed at all concentrations of S-59 and S-70, whereas the sample without psoralen gave a strong signal. AMT inhibited PCR amplification of the 1072 bp amplicon at the 70 and 100 mM levels, but a signal could be detected when AMT was used at 35 mM final concentration.

EXAMPLE 15

In Example 13, the compounds of the present invention were tested for their ability to inactivate virus in DMEM/15% FBS. In this example, the compounds are tested in both 100% plasma and predominantly synthetic media, to show that the methods of the present invention are not restricted to any particular type of medium.

For the samples in synthetic media: standard human platelet concentrates were centrifuged to separate plasma. Eighty-five percent of the plasma was then expressed off and replaced with a synthetic medium (referred to as "Sterilyte™ 3.0") containing 20 mM Na acetate, 2 mM glucose, 4 mM KCl, 100 mM NaCl, 10 mM $Na_3$ Citrate, 20 mM $NaH_2PO_4$/$Na2HPO_4$, and 2 mM $MgCl_2$. H9 cells infected with HIV were added to either the 85% Sterilyte™ 3.0 platelet concentrates or standard human platelet concentrates ($2.5 \times 10^7$ cells per concentrate), final concentration $5 \times 10^5$ cells/mL. The platelet concentrates were placed in Teflon™ modified FL20 or Teflon™ Minibags (American Fluoroseal Co., Silver Springs, Md.), treated with one of the compounds shown in FIGS. 18 and 19, at the concentrations shown, and then irradiated with 320–400 nm (20 mW/cm2) for 5 J/cm$^2$ (for plasma samples) or 2 J/cm$^2$ (for 85% Sterilyte™ 3.0 samples) on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured.

Figure 18:
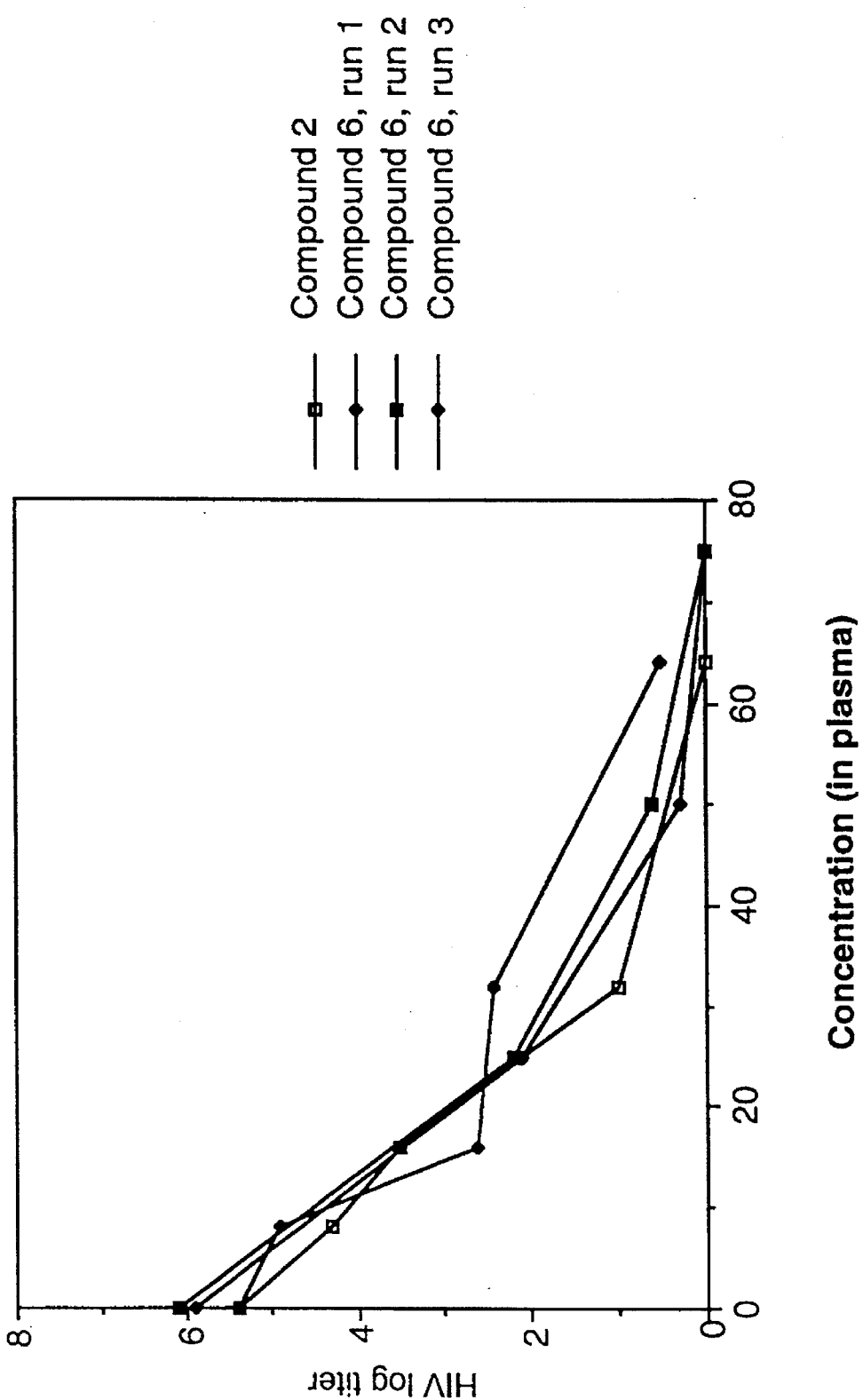
FIG. 18 shows the effect of varying the concentration of Compounds 2 and 6 of the present invention, in plasma.
Figure 19:
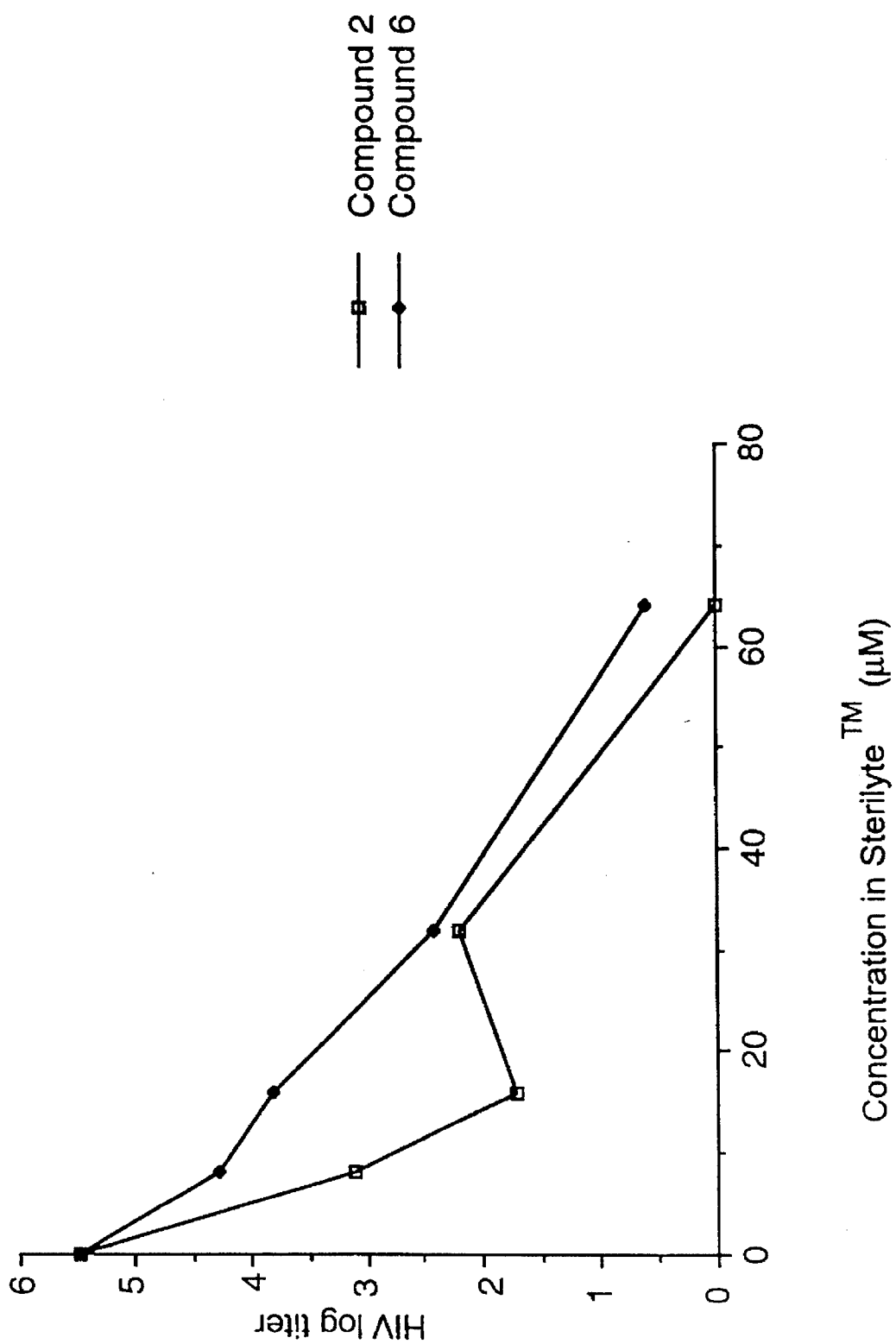
FIG. 19 shows the effect of varying the concentration of Compounds 2 and 6 of the present invention, in synthetic medium.

For samples run in plasma: H9 cells infected with HIV were added to standard human platelet concentrates (2.5× $10^7$ cells per concentrate), final concentration $5×10^5$ cells/mL. Aliquots of HIV contaminated platelet concentrate (5 mL) were placed in water jacketed Pyrex chambers. The chambers had previously been coated on the inside with silicon. The platelet concentrates were treated with one of the compounds listed in TABLES 10 and 11, below, at the concentrations listed in the table, and then irradiated with 320–400 nm (20 mW/cm$^2$) for 1 minute on a device similar to the Device of Example 1. The photoactivation device used here was previously tested and found to result in light exposure comparable to the Device of Example 1. (Data not shown). Aliquots for measurement of residual HIV infectivity in the samples treated with a compound of the present invention were withdrawn and cultured. Residual HIV infectivity was assayed for both the plasma and the 85% Sterilyte™ samples using an MT-2 infectivity assay. (Detailed in Example 13, above, and previously described in Hanson, C. V., et al., J. Clin. Micro 28:2030 (1990)). The results are shown in FIGS. 18 and 19.

The results support that the compounds of the present invention are effective in inactivating HIV in both plasma and synthetic medium. Comparing FIGS. 18 and 19, the inactivation curves appear to be the same, both achieving approximately 5 logs of inactivation at 64 µM concentrations of compound. However, the inactivation in synthetic media was performed with only 2 J/cm$^2$ irradiation, 3 J/cm$^2$ less than that required to acheive the same inactivation in plasma. Thus, it appears from the data that synthetic media facilitates the inactivation methods of the present invention.

EXAMPLE 16

In this example bacterial inactivation by the photoreactive nucleic acid binding compounds of the present invention was measured as a function of the ability of the bacteria to subsequently replicate. A gram negative bacteria was chosen as representative of the more difficult bacterial strains to inactivate.

The bacteria, a strain of Pseudomonus, was innoculated into LB with a sterile loop and grown overnight in a shaker at 37° C. Based on the approximation that one OD at 610 nm is equivalent to $5×10^8$ colony forming traits (cfu)/mL, a 1:10 dilution of the culture was measured on a spectrophotometer, (manufactured by Shimatsu). The bacterial culture was added to a solution of 15% fetal bovine serum in DMEM to a final bacteria concentration of approximately $10^6$/mL. An aliquot (0.8 mL) was transferred to a 1.5 mL snap-top polyethylene tube. An aliquot (0.004–0.040 mL) of the test compound stock solution prepared in water, ethanol or dimethylsulfoxide at 0.80–8.0 mM was added to the tube. Compounds were tested at a concentration of 16 µM. The tubes were placed in a light device as described in EXAMPLE 1 and irradiated with 1.3 J/cm$^2$, 1.2 J/cm$^2$, and finally 2.5 J/cm$^2$, for a total of 5 J/cm$^2$. 150 µL were removed for testing after each pulse period. Sterile 13 mL dilution tubes were prepared; each test compound required one tube with 0.4 mL of LB broth and four tubes containing 0.5 mL of LB broth. To make the dilutions, a 0.050 mL aliquot of the irradiated solution of phage and test compound was added to the first dilution tube of 0.5 mL of media then 0.050 mL of this solution was added to the second tube of 0.5 mL medium (1:10). The second solution was then diluted serially (1:10) into the remaining tubes. 100 µL of the original sample and each dilution are plated separately onto LB agar plates and incubated at 37° C. overnight. The colony forming units were then counted the following morning and the titer of the phage remaining after phototreatment was calculated based on the dilution factors.

The following controls were run: the "bacteria only" in which bacteria was not treated with test compound and not irradiated (listed as "starting titer" in the tables below); the "UV only" in which the bacteria was irradiated in the absence of test compound. Dark controls were not performed here for reasons set forth in Example 12 above.

The results were as follows. The starting titer of bacteria was 6.5 logs. After 5 J/cm$^2$ irradiation, the log kill for the various compounds tested were as follows: 8-MOP—1.9 logs, AMT—5.2 logs, Compound 2—>5.5, Compound 6—>5.5. From these results, it is clear that the compounds of the present invention are more efficient than both AMT and 8-MOP at inactivating a gram negative bacteria.

EXAMPLE 17

In the above examples, psoralens of the present invention have been demonstrated to be effective for inactivating pathogens, such as bacteria (pseudomonus), bacteriophage (R17) and viruses (HIV and DHBV). Without intending to be limited to any method by which the compounds of the present invention inactivate pathogens, it is believed that inactivation results from light induced binding of the psoralens to the nucleic acid of the pathogens. As discussed above, AMT is known both for its pathogen inactivation efficiency and its accompanying mutagenic action in the dark at low concentrations. In contrast, the less active psoralens, such as 8-MOP, that have been examined previously, show significantly less mutagenicity. This example establishes that photobinding and mutagenicity are not linked phenomenon in the compounds of the present invention. The psoralens of the present invention have exceptional pathogen inactivation efficiency while displaying only minimal mutagenicity.

In this example the compounds of the present invention are tested for their dark mutagenicity using an Ames assay. The procedures used for the Salmonella mutagenicity test as described in detail by Maron and Ames were followed exactly. Maron, D. M. and B. N. Ames, Mutation Research 113:173 1983). A brief description for each procedure is given here. The tester strains TA97a, TA98, TA100, TA102, TA1537 and TA1538 were obtained from Dr. Ames. TA97a, TA98, TA1537 and TA1538 are frameshift tester strains. TA100 and TA102 are base-substitution tester strains. Upon receipt each strain was cultured under a variety of conditions to confirm the genotypes specific to the strains.

The standard Salmonella tester strains used in this study require histidine for growth since each tester strain contains a different type of mutation in the histidine operon. In addition to the histidine mutation, these tester strains contain other mutations, described below, that greatly increase their ability to detect mutagen.

Histidine Dependence: The requirement for histidine was tested by streaking each strain first on a minimal glucose plate supplemented only with biotin and then on a minimal glucose plate supplemented with biotin and histidine. All strains grew the lack of growth of the strains in the absence of histidine.

rfa Mutation: A mutation which causes partial loss of the lipopolysaccharide barrier that coats the surface of the bacteria thus increasing permeability to large molecules was confirmed by exposing a streaked nutrient agar plate coated with the tester strain to crystal violet. First 100 μL of each culture was added to 2 mL of molten minimal top agar and poured onto a nutrient agar plate. Then a sterile filter paper disc saturated with crystal violet was placed at the center of each plate. After 16 hours of incubation at 37° C. the plates were scored and a clear zone of no bacterial growth was found around the disc, confirming the rfa mutation.

uvrB Mutation: Three strains used in this study contain a deficient UV repair system (TA97a, TA98, TA100, TA1537 and TA1538). This trait was tested for by streaking the strains on a nutrient agar plate, covering half of the plate, and irradiating the exposed side of the plate with germicidal lamps. After incubation growth was only seen on the side of the plate shielded from UV irradiation.

R-factor: The tester strains (TA97a, TA98, TA100, and TA102) contain the pKM101 plasmid that increases their sensitivity to mutagens. The plasmid also confers resistance to ampicillin to the bacteria. This was confirmed by growing the strains in the presence of ampicillin.

pAQ1: Strain TA102 also contains the pAQ1 plasmid that further enhances its sensitivity to mutagens. This plasmid also codes for tetracycline resistance. To test for the presence of this plasmid TA102 was streaked on a minimal glucose plate containing histidine, biotin, and tetracycline. The plate was incubated for 16 hours at 37° C. The strain showed normal growth indicating the presence of the pAQ1 plasmid.

The same cultures used for the genotype testing were again cultured and aliquots were frozen under controlled conditions. The cultures were again tested for genotype to confirm the fidelity of the genotype upon manipulation in preparing the frozen permanents.

The first tests done with the strains were to determine the range of spontaneous reversion for each of the strains. With each mutagenicity experiment the spontaneous reversion of the tester strains to histidine independence was measured and expressed as the number of spontaneous revertants per plate. This served as the background controls. A positive mutagenesis control was included for each tester strain by using a diagnostic mutagen suitable for that strain (2-aminofluorene at 5 mg/plate for TA98 and sodium azide at 1.5 mg/plate for TA100).

For all experiments, the pre-incubation procedure was used. In this procedure one vial of each tester strain was thawed and 20 μL of this culture was added to 6 mL of Oxoid Nutrient Broth #2. This solution was allowed to shake for 10 hours at 37° C. In the preoincubation procedure, 0.1 mL of this overnight culture was added to each of the required number of sterile test tubes. To half of the tubes 0.5 mL of a 10% S-9 solution containing Aroclor 1254 induced rat liver extract (Molecular Toxicology Inc., Annapolis, Md.), and $MgCl_2$, KCl, glucose-6-phosphate, NADP, and sodium phosphate buffer (Sigma, St. Louis, Mo.) were added. To the other half of the tubes 0.5 mL of 0.2M sodium phospate buffer, pH 7.4, was used in place of the S-9 mixture (the -S9 samples). Finally 0.1 mL of the test solution containing either 0, 0.1, 0.5, 1, 5, 10, 50, 100, 250, or 500 μg/mL of the test compound was added. The 0.7 mL mixture was vortexed and then pre-incubated while shaking for 20 minutes at 37° C. After shaking, 2 mL of molten top agar supplemented with histidine and biotin were added to the 0.7 mL mixture and immediately poured onto a minimal glucose agar plate (volume of base agar was 20 mL). The top agar was allowed 30 minutes to solidify and then the plates were inverted and incubated for 44 hours at 37° C. After incubation the number of revertant colonies on each plate were counted. The results appear in TABLES 12 (A)–18 (B), below. ("n" represents the number of replicates performed for each data point.)

TABLE 12 (A)

| | AMT | | | | | |
|---|---|---|---|---|---|---|
| STRAIN | TA97a −S9 | TA97a +S9 | TA98 −S9 | TA98 +S9 | TA100 −S9 | TA100 +S9 |
| Dose μg/plate | | | | | | |
| 0 | 109 n = 23 | 158 n = 39 | 20 n = 38 | 25 n = 53 | 126 n = 41 | 123 n = 56 |
| 0.1 | 14 n = 3 | −23 n = 6 | 3 n = 3 | 1 n = 6 | −10 n = 3 | −16 n = 6 |
| 0.5 | 9 n = 3 | 32 n = 6 | 5 n = 3 | 3 n = 6 | 13 n = 3 | −12 n = 6 |
| 1 | 54 n = 3 | 32 n = 6 | 5 n = 3 | 21 n = 6 | 17 n = 3 | −19 n = 6 |
| 5 | 73 n = 3 | 149 n = 6 | 16 n = 6 | 232 n = 9 | 59 n = 9 | −6 n = 12 |
| 10 | | | 20 n = 9 | 403 n = 9 | 105 n = 15 | 17 n = 15 |
| 50 | | | 69 n = 9 | 620 n = 9 | 73 n = 9 | 52 n = 9 |
| 100 | | | 114 n = 9 | 745 n = 9 | 75 n = 9 | 85 n = 9 |
| 250 | | | 112 n = 6 | 933 n = 6 | 24 n = 6 | 89 n = 6 |
| Positive Control | | 5 μg/plate 2-Amino fluorene 808 n = 21 | | 5 μg/plate 2- Amino- fluorene 1154 n = 35 | 1.5 μg/plt sodium azide 965 n = 38 | |

TABLE 12 (B)

| STRAIN | AMT | | | | | |
|---|---|---|---|---|---|---|
| | TA97a −S9 | TA97a +S9 | TA98 −S9 | TA98 +S9 | TA100 −S9 | TA100 +S9 |
| Dose Dose µg/plate | | | | | | |
| 0 | 346 n = 26 | 404 n = 41 | 9 n = 30 | 9 n = 45 | 15 n = 30 | 19 n = 42 |
| 0.1 | 27 n = 3 | −20 n = 6 | 0 n = 3 | 2 n = 6 | 3 n = 3 | 3 n = 6 |
| 0.5 | 47 n = 3 | 5 n = 6 | 3 n = 9 | 2 n = 12 | 4 n = 9 | 13 n = 12 |
| 1 | 88 n = 3 | −17 n = 6 | 5 n = 9 | 3 n = 12 | 4 n = 9 | 37 n = 12 |
| 5 | 266 n = 3 | 51 n = 6 | 44 n = 9 | 22 n = 12 | 13 n = 18 | 177 n = 21 |
| 10 | | | 52 n = 9 | 30 n = 9 | 14 n = 9 | 255 n = 9 |
| 50 | | | 2688 n = 9 | 9 n = 9 | | |
| 100 | | | 2068 n = 9 | 686 n = 9 | | |
| 250 | | | 434 n = 9 | 3738 n = 12 | | |
| Positive Control | 100 µg/pl hydrogen peroxide 660 n = 23 | | 10 µg/plt 9-Amino acridine 284 n = 6 | 10 µg/plt 2-Amino-fluorene 73 n = 24 | | 5 µg/plate 2-Amino-fluorene 1064 n = 30 |

TABLE 13 (A)

| STRAIN | 8-MOP | | | |
|---|---|---|---|---|
| | TA102 −S9 | TA102 +S9 | TA1537 −S9 | TA1537 +S9 |
| Dose µg/plate | | | | |
| 0 | 346 n = 26 | 404 n = 41 | 9 n = 30 | 9 n = 45 |
| 1 | −55 n = 14 | −46 n = 17 | | |
| 10 | −57 n = 14 | −27 n = 17 | | |
| 30 | | | 5 n = 3 | 1 n = 6 |
| 60 | | | 3 n = 3 | 1 n = 6 |
| 90 | | | −1 n = 3 | −4 n = 6 |
| 100 | 217 n = 14 | 290 n = 17 | | |
| 500 | 781 n = 11 | 1179 n = 11 | | |
| Positive Control | 100 µg/plt hydrogen peroxide 660 n = 23 | | 10 µg/plt 9-Amino-Acridine 284 n = 6 | 10 µg/plt 2-Amino-fluorene 73 n = 24 |

TABLE 13 (B)

| STRAIN | 8-MOP | | | |
|---|---|---|---|---|
| | TA102 −S9 | TA102 +S9 | TA1537 −S9 | TA1537 +S9 |
| Dose µg/plate | | | | |
| 0 | 346 n = 26 | 404 n = 41 | 9 n = 30 | 9 n = 45 |
| 1 | −55 n = 14 | −46 n = 17 | | |
| 10 | −57 n = 14 | −27 n = 17 | | |
| 30 | | | 5 n = 3 | 1 n = 6 |
| 60 | | | 3 n = 3 | 1 n = 6 |
| 90 | | | −1 n = 3 | −4 n = 6 |
| 100 | 217 n = 14 | 290 n = 17 | | |
| 500 | 781 n = 11 | 1179 n = 11 | | |
| Positive Control | 100 µg/plt hydrogen peroxide 660 n = 23 | | 10 µg/plt 9-Amino-Acridine 284 n = 6 | 10 µg/plt 2-Amino-fluorene 73 n = 24 |

TABLE 14

| | Compound 1 | | | |
|---|---|---|---|---|
| STRAIN | TA100 −S9 | TA100 +S9 | TA1538 −S9 | TA1538 +S9 |
| Dose µg/plate | | | | |
| 0 | 126 n = 41 | 123 n = 56 | 15 n = 30 | 19 n = 42 |
| 5 | 292 n = 3 | −24 n = 3 | 10 n = 3 | 21 n = 3 |
| 10 | 337 n = 3 | −22 n = 3 | 12 n = 3 | 22 n = 3 |
| Positive Control | 1.5 µg/plate Sodium Azide 965 n = 38 | | | 5 µg/plate 2-Amino-fluorene 1064 n = 30 |

TABLE 15 (A)

| | Compound 2 | | | |
|---|---|---|---|---|
| STRAIN | TA98 −S9 | TA98 +S9 | TA100 −S9 | TA100 +S9 |
| Dose µg/plate | | | | |
| 0 | 20 n = 35 | 25 n = 50 | 126 n = 41 | 123 n = 56 |
| 5 | | | 103 n = 3 | −18 n = 3 |
| 10 | 28 n = 3 | 24 n = 3 | 46 n = 6 | 1 n = 6 |
| 50 | 52 n = 3 | 35 n = 3 | 182 n = 3 | 115 n = 3 |
| 100 | 39 n = 6 | 53 n = 6 | 121 n = 3 | 96 n = 3 |
| 250 | 29 n = 3 | 69 n = 3 | | |
| 500 | 6 n = 3 | 63 n = 3 | | |
| Positive Control | 10 µg/plt 9-Amino-acridine 284 n = 6 | 10 µg/plt 2-Amino-fluorene 73 n = 24 | | 5 µg/plate 2-Amino-fluorene 1064 n = 30 |

TABLE 15 (B)

| | Compound 2 | | | |
|---|---|---|---|---|
| STRAIN | TA1537 −S9 | TA1537 +S9 | TA1538 −S9 | TA1538 +S9 |
| Dose µg/plate | | | | |
| 0 | 9 n = 30 | 9 n = 45 | 15 n = 30 | 19 n = 42 |
| 5 | | | −8 n = 3 | 2 n = 3 |
| 10 | 36 n = 3 | 5 n = 3 | −13 n = 3 | 4 n = 3 |
| 50 | 282 n = 3 | 40 n = 3 | | |
| 100 | 258 n = 3 | 88 n = 3 | | |
| 250 | 176 n = 3 | 744 n = 3 | | |
| 500 | 114 n = 3 | 395 n = 3 | | |

TABLE 15 (B)-continued

| | Compound 2 | | | |
|---|---|---|---|---|
| STRAIN | TA1537 −S9 | TA1537 +S9 | TA1538 −S9 | TA1538 +S9 |
| Positive Control | 10 µg/plt 9-Amino-acridine 284 n = 6 | 10 µg/plt 2-Amino-fluorene 73 n = 24 | | 5 µg/plate 2-Amino-fluorene 1064 n = 30 |

TABLE 16

| | Compound 3 | | | |
|---|---|---|---|---|
| STRAIN | TA100 −S9 | TA100 +S9 | TA1538 −S9 | TA1538 +S9 |
| Dose µg/plate | | | | |
| 0 | 126 n = 41 | 123 n = 56 | 15 n = 30 | 19 n = 42 |
| 5 | 47 n = 3 | −19 n = 3 | 0 n = 3 | 1 n = 3 |
| 10 | 47 n = 3 | 8 n = 3 | −6 n = 3 | 9 n = 3 |
| Positive Control | 1.5 µg/plt Sodium Azide 965 n = 38 | | | 5 µg/plt 2-Amino-fluorene 1064 n = 30 |

TABLE 17

| | Compound 4 | | | |
|---|---|---|---|---|
| STRAIN | TA100 −S9 | TA100 +S9 | TA1538 −S9 | TA1538 +S9 |
| Dose µg/plate | | | | |
| 0 | 126 n = 41 | 123 n = 56 | 15 n = 30 | 19 n = 42 |
| 5 | −41 n = 3 | −10 n = 3 | −2 n = 3 | 7 n = 3 |
| 10 | 3 n = 3 | −3 n = 3 | −2 n = 3 | −2 n = 3 |
| Positive Control | 1.5 µg/plate Sodium Azide 965 n = 38 | | | 5 µg/plate 2-Amino-fluorene 1064 n = 30 |

TABLE 18 (A)

| | Compound 6 | | | |
|---|---|---|---|---|
| STRAIN | TA98 −S9 | TA98 +S9 | TA100 −S9 | TA100 +S9 |
| Dose µg/plate | | | | |
| 0 | 20 n = 38 | 25 n = 53 | 126 n = 41 | 123 n = 56 |
| 5 | | | −32 n = 3 | 12 n = 3 |
| 10 | 12 n = 3 | −5 n = 3 | 3 n = 9 | −5 n = 9 |
| 50 | 12 | 2 | 2 | 24 |

TABLE 18 (A)-continued

Compound 6

| STRAIN | TA98 −S9 | TA98 +S9 | TA100 −S9 | TA100 +S9 |
|---|---|---|---|---|
| 100 | n = 3 22 | n = 3 20 | n = 6 −18 | n = 6 −2 |
| 250 | n = 6 12 | n = 6 40 | n = 6 | n = 6 −38 |
| 500 | n = 3 9 | n = 3 52 | | n = 3 |
| | n = 3 | n = 3 | | |
| Positive Control | | 5 µg/plate 2-Amino- fluorene 1154 n = 35 | 1.5 µg/plate Sodium Azide 966 n = 38 | |

| STRAIN | TA1537 −S9 | TA1537 +S9 | TA1538 −S9 | TA1538 +S9 |
|---|---|---|---|---|

TABLE 18 (B)

Compound 6

| STRAIN | TA98 −S9 | TA98 +S9 | TA100 −S9 | TA100 +S9 |
|---|---|---|---|---|
| Dose µg/plate | | | | |
| 0 | 9 n = 30 | 9 n = 45 | 15 n = 30 | 19 n = 42 |
| 5 | | | −5 n = 3 | 0 n = 3 |
| 10 | 141 n = 6 | −1 n = 6 | −2 n = 3 | 8 n = 3 |
| 50 | 2010 n = 6 | 17 n = 6 | | |
| 100 | 785 n = 6 | 35 n = 6 | | |
| 250 | 228 n = 6 | 99 n = 6 | | |
| 500 | 43 n = 3 | 369 n = 3 | | |
| Positive Control | 10 µg/plate 9-Amino- acridine 284 n = 6 | 10 µg/plate 2-Amino- fluorene 73 n = 24 | | 5 µg/plate 2-Amino- fluorene 1064 n = 30 |

TABLE 19 (A)

Compound 18

| STRAIN | TA98 −S9 | TA98 +S9 |
|---|---|---|
| Dose µg/plate | | |
| 0 | 17 n = 3 | 28 n = 3 |
| 5 | | |
| 10 | 21 n = 3 | 8 n = 3 |
| 50 | 303 n = 3 | 6 n = 3 |
| 100 | 390 n = 6 | 26 n = 6 |
| 200 | 225 n = 3 | 42 n = 3 |
| 500 | | |
| Positive | | 5 µg/plate |

TABLE 19 (A)-continued

Compound 18

| STRAIN | TA98 −S9 | TA98 +S9 |
|---|---|---|
| Control | | 2-Amino- fluorene 2589 n = 3 |

TABLE 19 (B)

Compound 18

| STRAIN | TA98 −S9 | TA98 +S9 |
|---|---|---|
| Dose µg/plate | | |
| 0 | 8 n = 3 | 7 n = 3 |
| 5 | | |
| 10 | 21 n = 3 | 8 n = 3 |
| 50 | 303 n = 3 | 6 n = 3 |
| 100 | 390 n = 3 | 26 n = 3 |
| 200 | 225 n = 3 | 42 n = 3 |
| 500 | | |
| | 100 µg/plate AMT 608 n = 3 | 100 µg/plate AMT 500 n = 3 |

Maron and Ames (1983) describe the conflicting views with regard to the statistical treatment of data generated from the test. In light of this, this example adopts the simple model of mutagenicity being characterized by a two-fold or greater increase in the number of revertants above background (in bold in the tables), as well as dose dependent mutagenic response to drug.

With regard to 8-MOP, the only mutagenic response detected was a weak base-substitution mutagen in TA102 at 500 µg/plate (TABLE 13 (B)).

In sharp contrast, AMT (TABLE 12 (A) and 12 (B)) showed frameshift mutagenicity at between 5 and 10 µg/plate in TA97a and TA98, at 5 µg/plate in TA1537 and at 1 µg/plate in TA1538. AMT showed no significant base-substitution mutations.

Looking at Compound 1, the only mutagenic response detected was a weak frameshift mutagen in TA1538 at 5 µg/plate in the presence of S9. Compound 1 also displayed mutation in the TA100 strain, but only in the absence of S9. Compound 2 also showed weak frameshift mutagenicity in the presence of S9 in TA98 and TA1537. Compounds 3 and 4 showed no mutagenicity. Compound 6 had no base substitution mutagenicity, but showed a frameshift response in TA98 in the presence of S9 at concentrations of 250 µg/plate and above. It also showed a response at 50 µg/plate in TA1537 in the presence of S9. Compound 18 showed only a weak response at high concentrations in the presence of S9 in strains TA 9o and TA1537. The response was higher in the absence of S9, but still was significantly below that of AMT, which displayed mutagenicity at much lower concentrations (5 µg/plate).

From this data it is clear that the compounds of the present invention are less mutagenic than AMT, as defined by the Ames test. At the same time, these compounds show much higher inactivation efficiency than 8-MOP, as shown in Examples 12 and 16. These two factors support that the compounds of the present invention combine the best features of both AMT and 8-MOP, high inactivation efficiency and low mutagenicity.

EXAMPLE 18

Figure 20A:
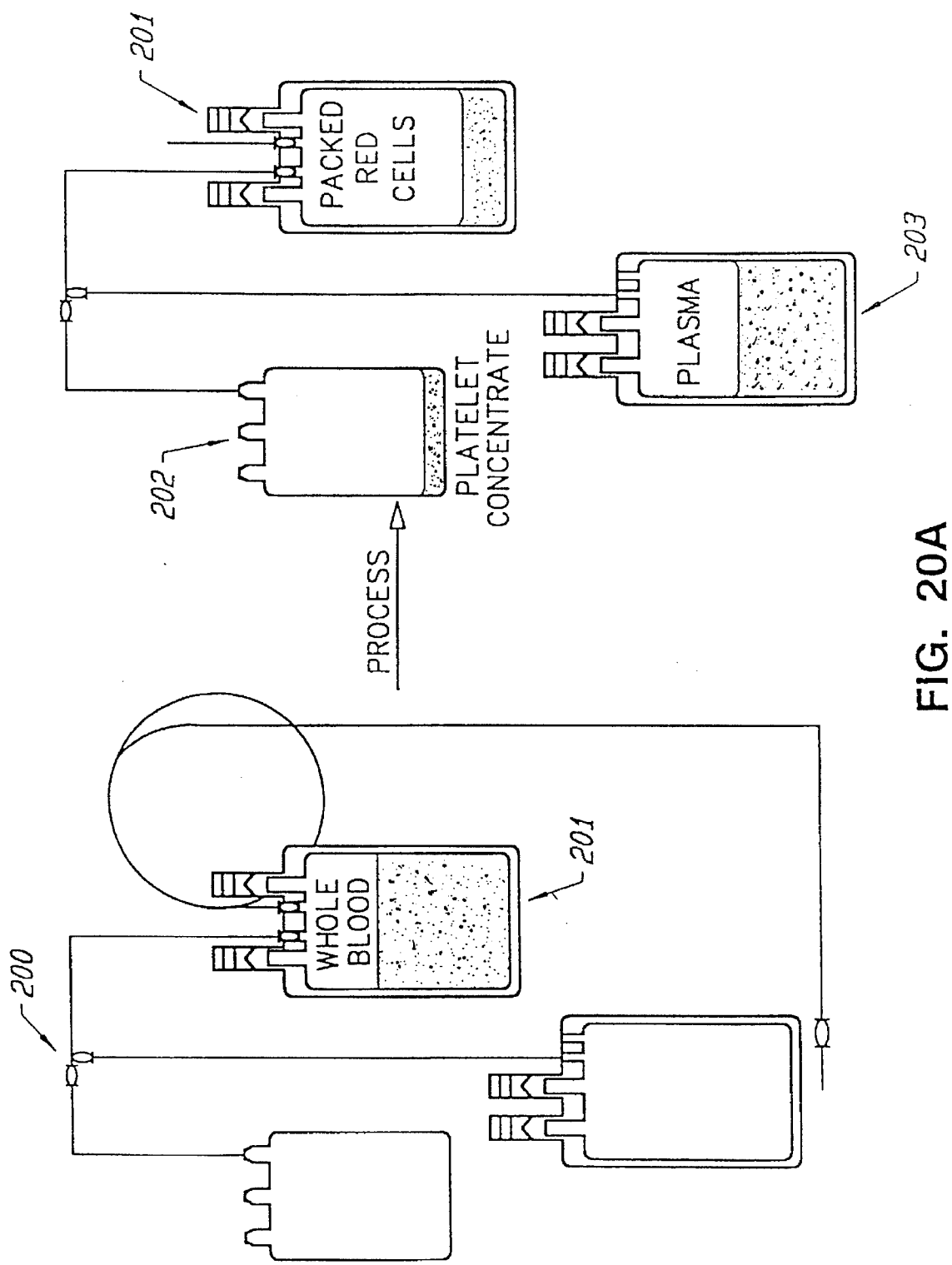
FIG. 20A schematically shows the standard blood product separation approach used presently in blood banks.

In Example 15, the compounds of the present invention exhibited the ability to inactivate pathogens in synthetic media. This example describes methods by which synthetic media and compounds of the present invention may be introduced and used for inactivating pathogens in blood. FIG. 20A schematically shows the standard blood product separation approach used presently in blood banks. Three bags are integrated by flexible tubing to create a blood transfer set (200) (e.g., commercially available from Baxter, Deerfield, Ill.). After blood is drawn into the first bag (201), the entire set is processed by centrifugation (e.g., Sorvall™ swing bucket centrifuge, Dupont), resulting in packed red cells and platelet rich plasma in the first bag (201). The plasma is expressed off of the first bag (201) (e.g., using a Fenwall™ device for plasma expression), through the tubing and into the second bag (202). The first bag (201) is then detached and the two bag set is centrifuged to create platelet concentrate and platelet-poor plasma; the latter is expressed off of the second bag (202) into the third bag (203).

Figure 20B:
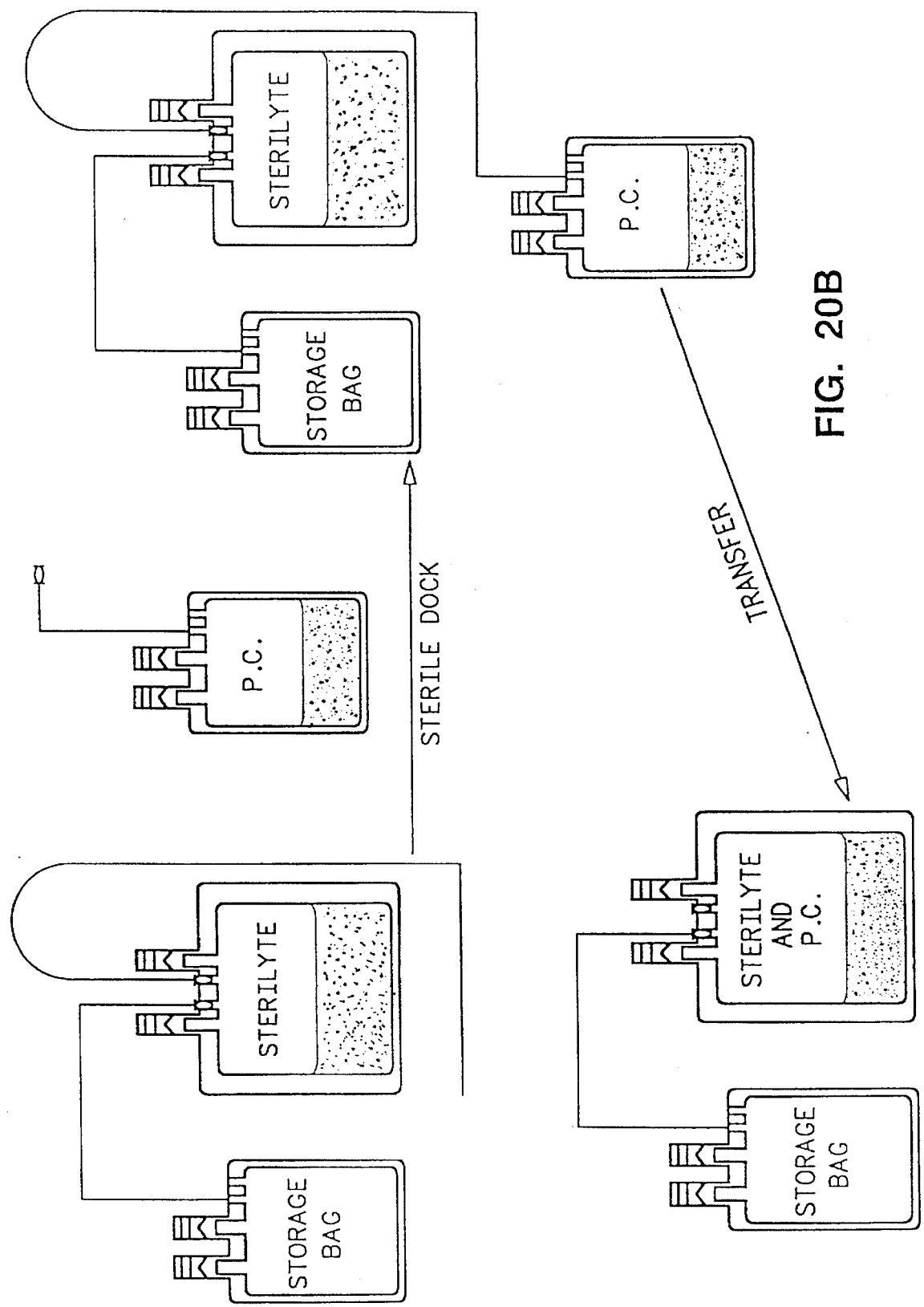
FIG. 20B schematically shows an embodiment of the present invention whereby synthetic media is introduced to platelet concentrate prepared as in FIG. 20A.

FIG. 20B schematically shows an embodiment of the present invention by which synthetic media and photoactivation compound are introduced to platelet concentrate prepared as in FIG. 20A. A two bag set (300) is sterile docked with the platelet concentrate bag (202) (indicated as "P.C."). Sterile docking is well-known to the art. See e.g., U.S. Pat. No. 4,412,835 to D. W. C. Spencer, hereby incorporated by reference. See also U.S. Pat. Nos. 4,157,723 and 4,265,280, hereby incorporated by reference. Sterile docking devices are commercially available (e.g., Terumo, Japan).

One of the bags (301) of the two bag set (300) contains a synthetic media formulation of the present invention (indicated as "STERILYTE"). In the second step shown in FIG. 20B, the platelet concentrate is mixed with the synthetic media by transferring the platelet concentrate to the synthetic media bag (301) by expressing the platelet concentrate from the first blood bag into the second blood bag via a sterile connection means. The photoactivation compound can be in the bag containing synthetic media (301), added at the point of manufacture. Alternatively, the compound can be mixed with the blood at the point of collection, if the compound is added to the blood collection bag (FIG. 20A, 201) at the point of manufacture. The compound may be either in dry form or in a solution compatable with the maintainance of blood.

Figure 20C:
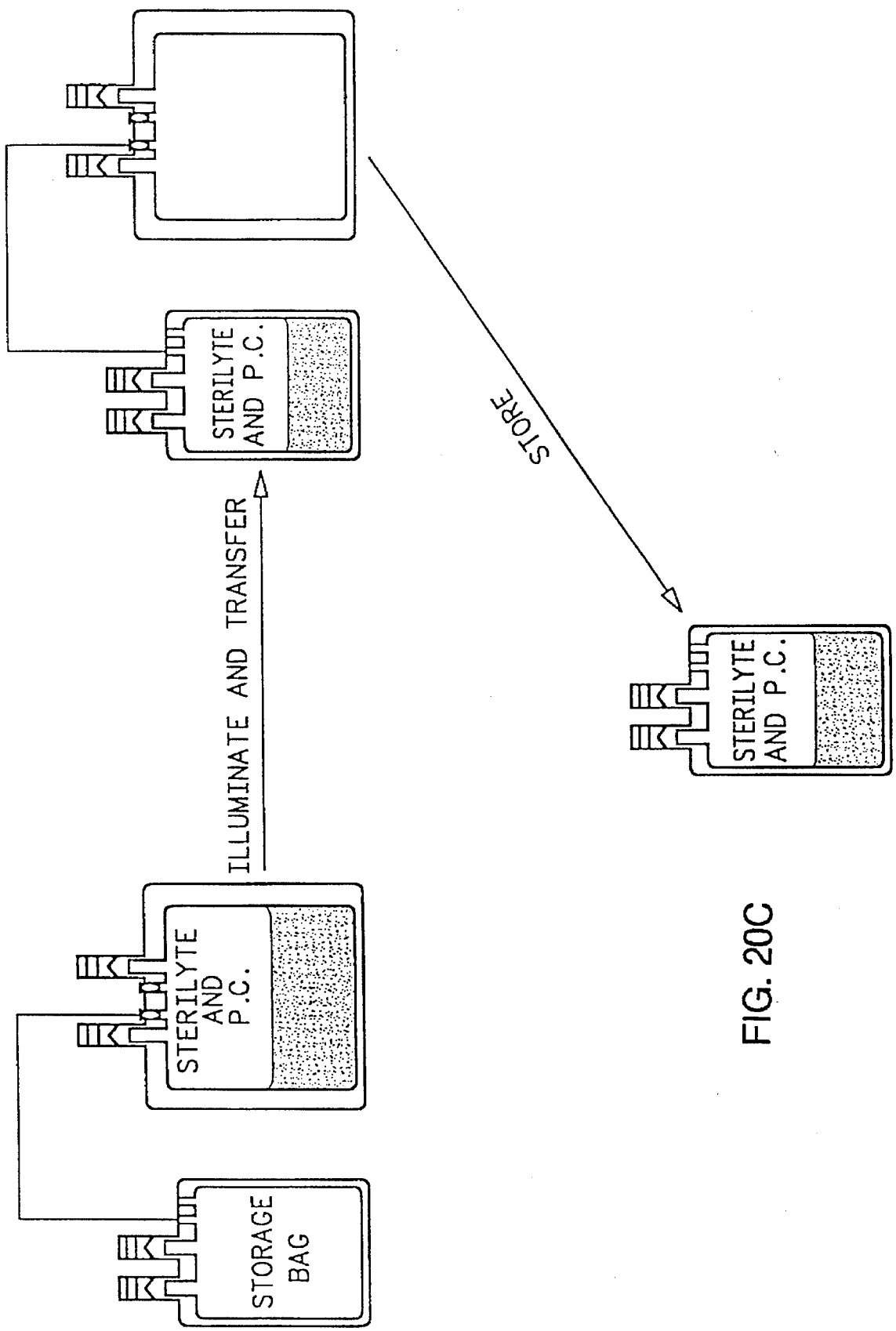
FIG. 20C schematically shows one embodiment of the decontamination approach of the present invention applied specifically to platelet concentrate diluted with synthetic media as in FIG. 20B.
Figure 21A:
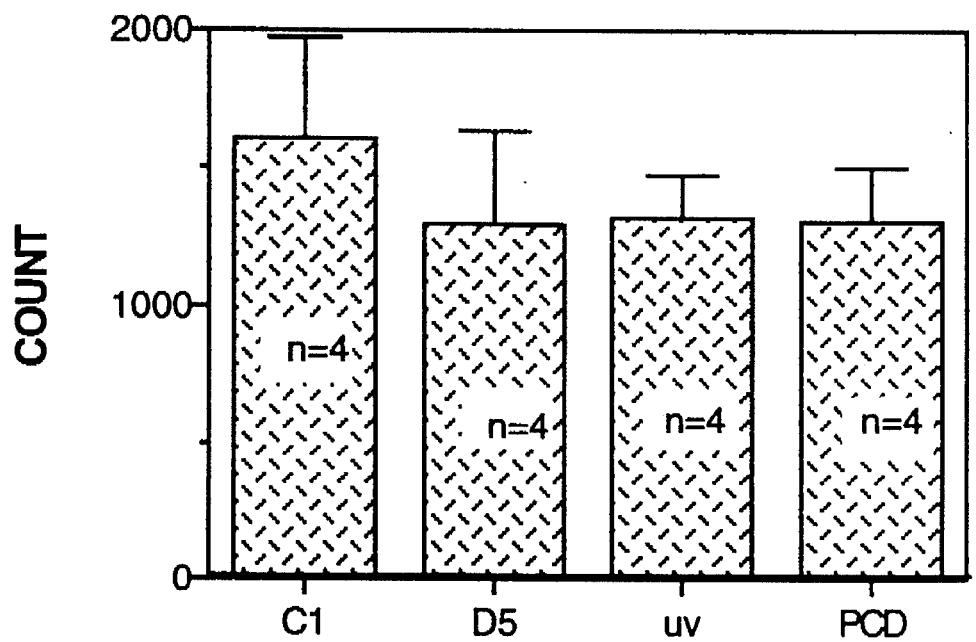
FIG. 21A is a graph comparing the effects of 5-day storage (D5), ultraviolet light (uv) and treatment with Compound 2 at 100 µM (PCD) on platelet function as measured by platelet count. "n" represents the number of experiments represented by the data point.
Figure 21B:
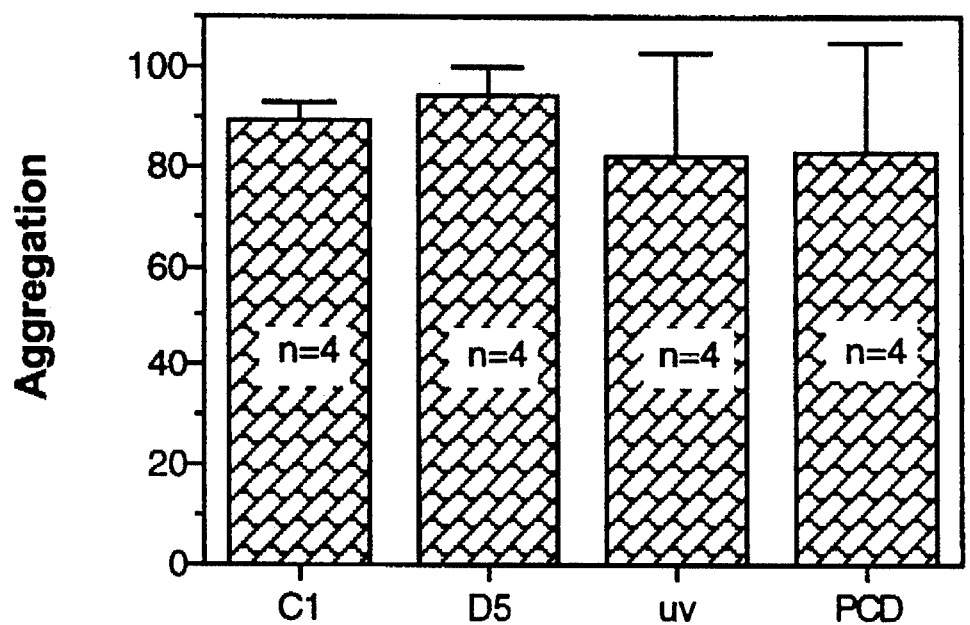
FIG. 21B is a graph comparing the effects of 5-day storage (D5), ultraviolet light (uv) and treatment with Compound 2 at 100 µM (PCD) on platelet function as measured by platelet aggregation. "n" represents the number of experiments represented by the data point.
Figure 21C:
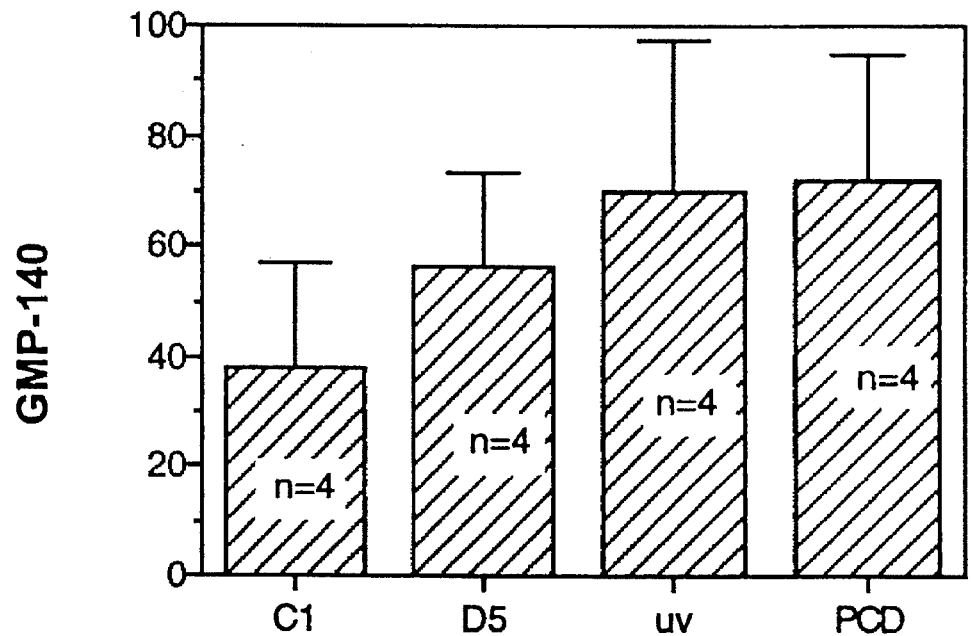
FIG. 21C is a graph comparing the effects of 5-day storage (D5), ultraviolet light (uv) and treatment with Compound 2 at 100 µM (PCD) on platelet function as measured by GMP-140 expression. "n" represents the number of experiments represented by the data point.
Figure 21D:
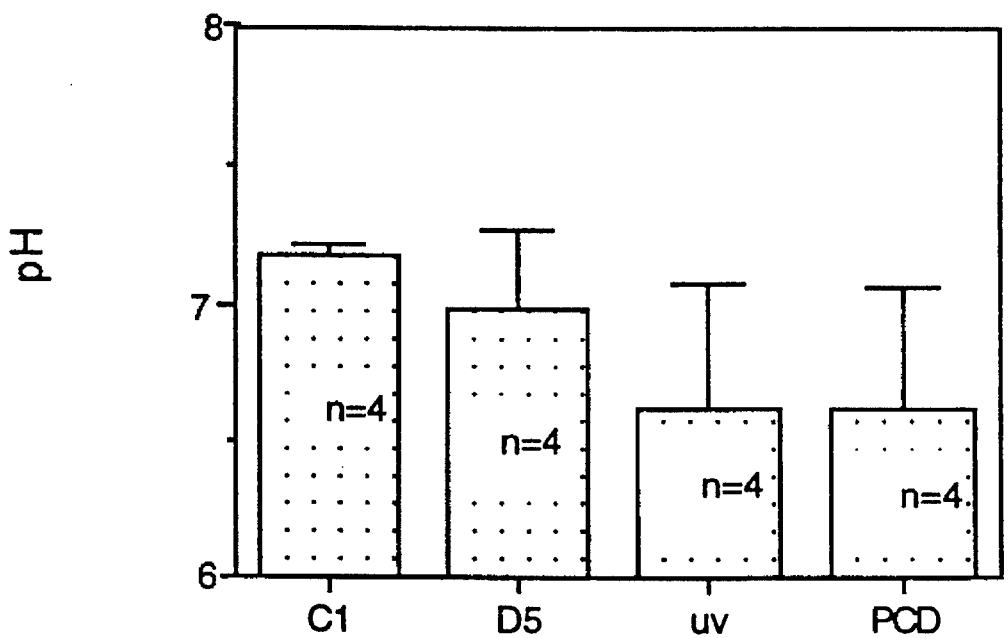
FIG. 21D is a graph comparing the effects of 5-day storage (D5), ultraviolet light (uv) and treatment with Compound 2 at 100 µM (PCD) on platelet function as measured by pH. "n" represents the number of experiments represented by the data point.
Figure 22A:
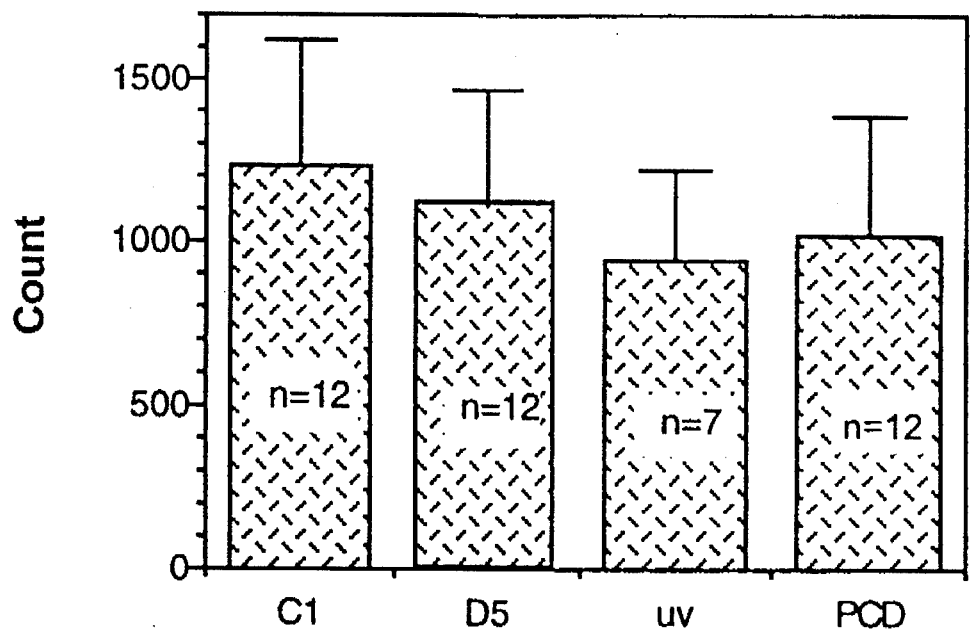
FIG. 22A is a graph comparing the effects of 5-day storage (D5), ultraviolet light (uv) and treatment with Compound 6 at 100 µM (PCD) on platelet function as measured by platelet count. "n" represents the number of experiments represented by the data point.
Figure 22B:
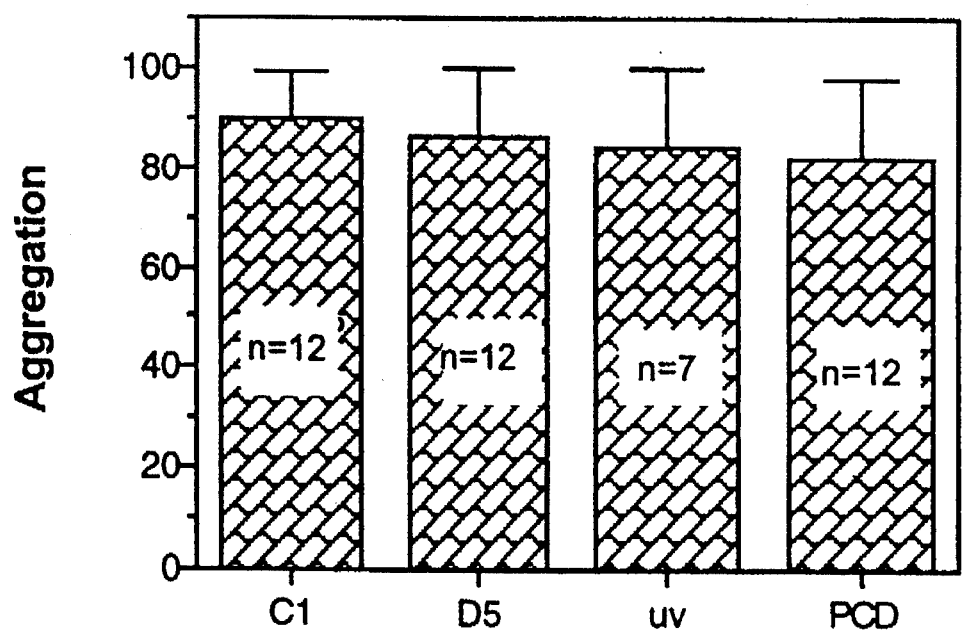
FIG. 22B is a graph comparing the effects of 5-day storage (D5), ultraviolet light (uv) and treatment with Compound 6 at 100 µM (PCD) on platelet function as measured by platelet aggregation. "n" represents the number of experiments represented by the data point.
Figure 22C:
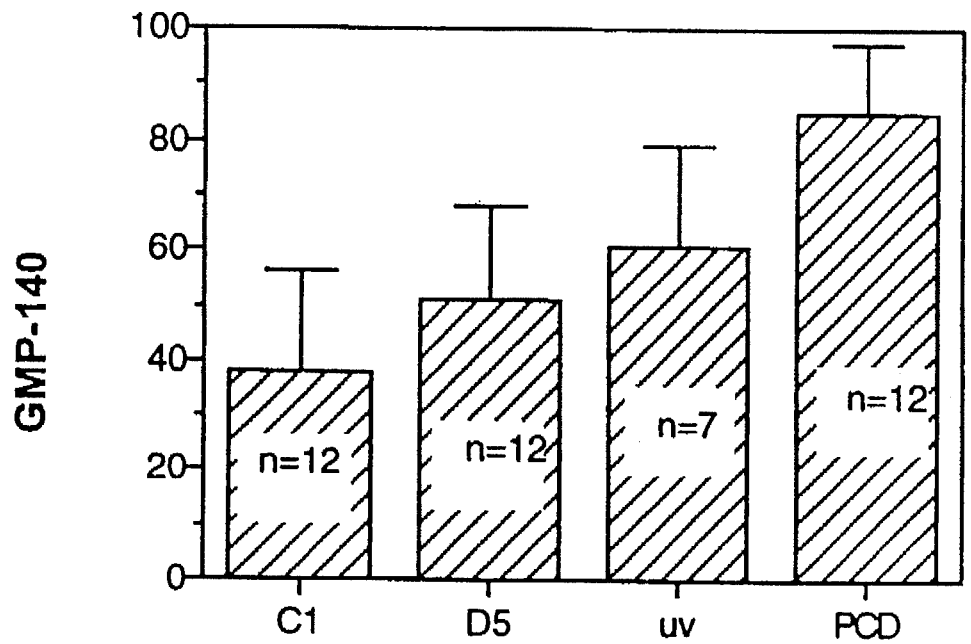
FIG. 22C is a graph comparing the effects of 5-day storage (D5), ultraviolet light (uv) and treatment with Compound 6 at 100 µM (PCD) on platelet function as measured by GMP-140 expression. "n" represents the number of experiments represented by the data point.
Figure 22D:
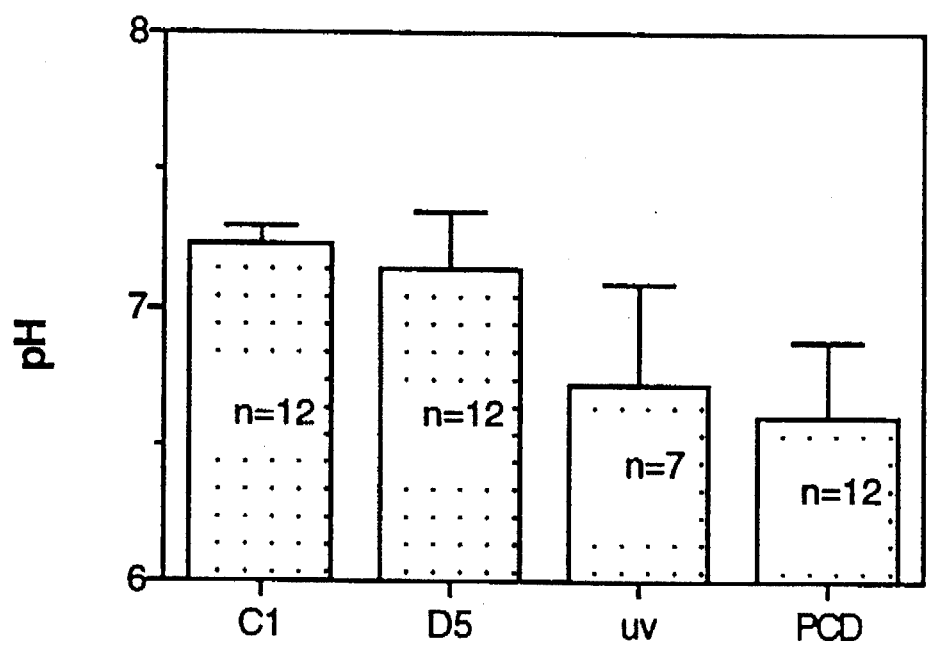
FIG. 22D is a graph comparing the effects of 5-day storage (D5), ultraviolet light (uv) and treatment with Compound 6 at 100 µM (PCD) on platelet function as measured by pH. "n" represents the number of experiments represented by the data point.
Figure 23A:
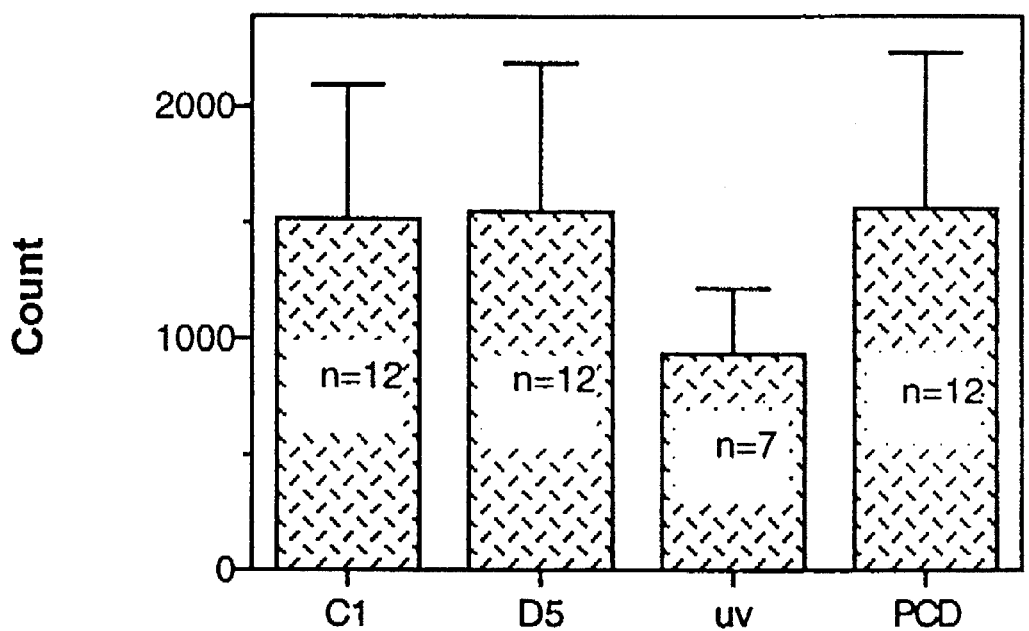
FIG. 23A is a graph comparing the effects of 5-day storage (D5), ultraviolet light (uv) and treatment with Compound 17 at 100 μM (PCD) on platelet function as measured by platelet count. "n" represents the number of experiments represented by the data point.
Figure 23B:
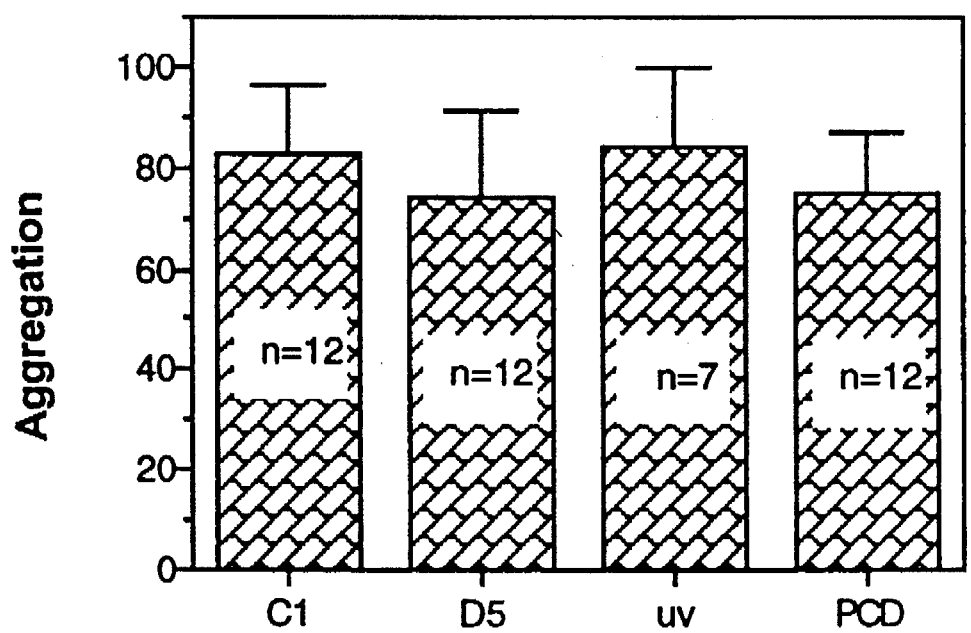
FIG. 23B is a graph comparing the effects of 5-day storage (D5), ultraviolet light (uv) and treatment with Compound 17 at 100 μM (PCD) on platelet function as measured by platelet aggregation. "n" represents the number of experiments represented by the data point.
Figure 23C:
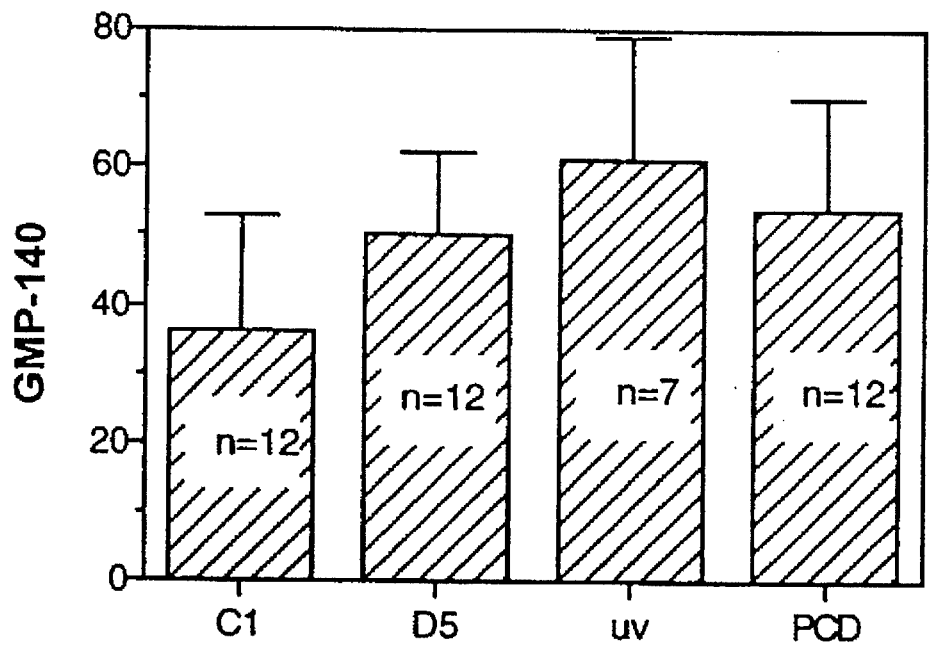
FIG. 23C is a graph comparing the effects of 5-day storage (D5), ultraviolet light (uv) and treatment with Compound 17 at 100 μM (PCD) on platelet function as measured by GMP-140 expression. "n" represents the number of experiments represented by the data point.
Figure 23D:
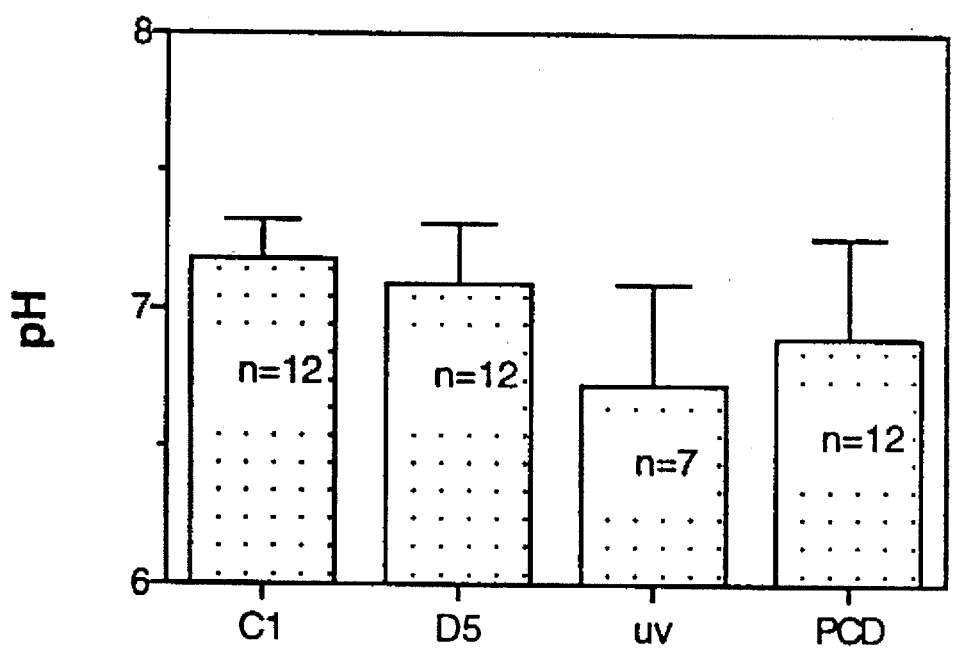
FIG. 23D is a graph comparing the effects of 5-day storage (D5), ultraviolet light (uv) and treatment with Compound 17 at 100 μM (PCD) on platelet function as measured by pH. "n" represents the number of experiments represented by the data point.
Figure 24A:
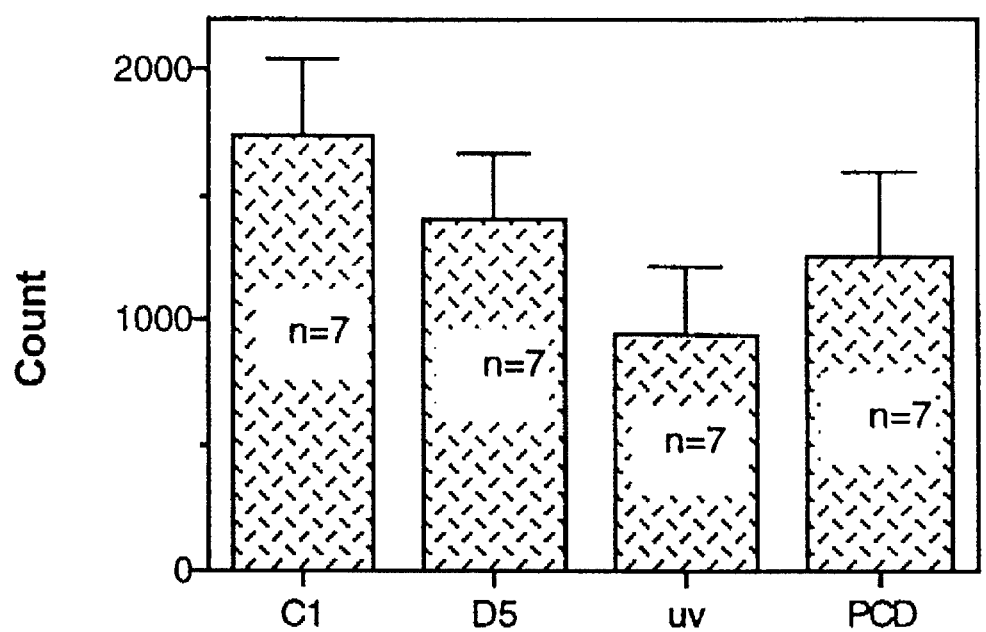
FIG. 24A is a graph comparing the effects of 5-day storage (D5), ultraviolet light (uv) and treatment with Compound 18 at 100 μM (PCD) on platelet function as measured by platelet count. "n" represents the number of experiments represented by the data point.
Figure 24B:
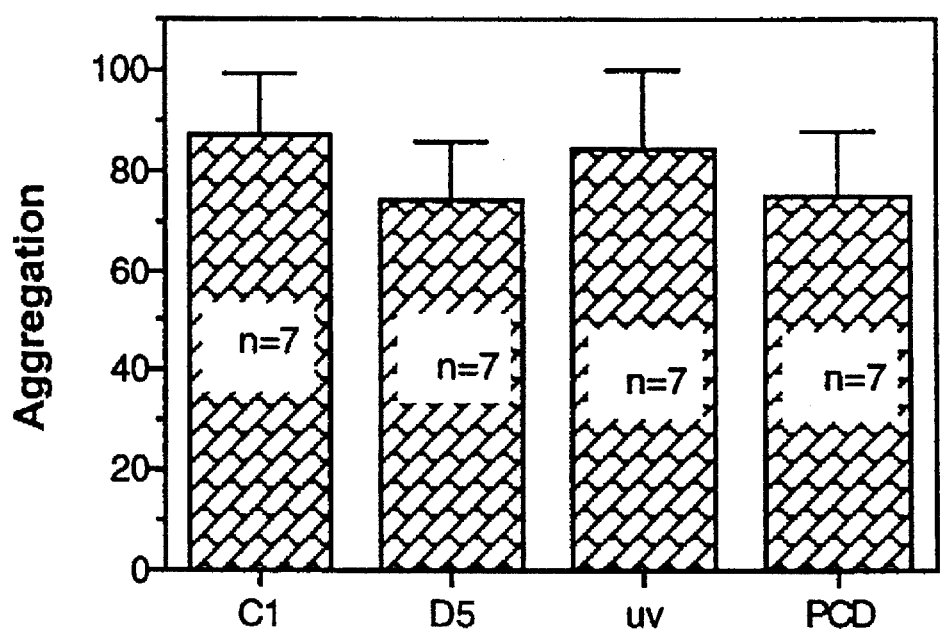
FIG. 24B is a graph comparing the effects of 5-day storage (D5), ultraviolet light (uv) and treatment with Compound 18 at 100 μM (PCD) on platelet function as measured by platelet aggregation. "n" represents the number of experiments represented by the data point.
Figure 24C:
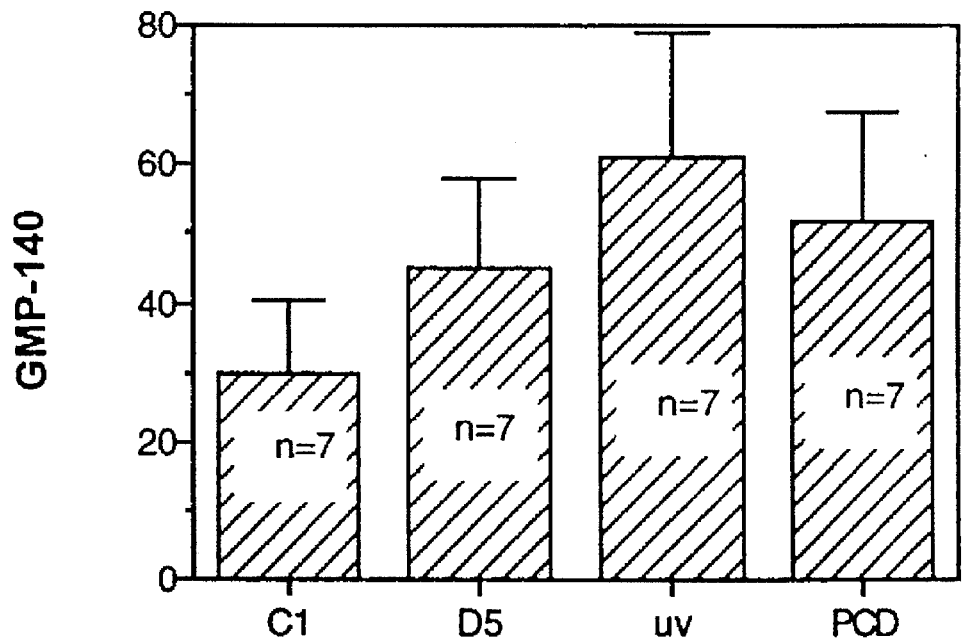
FIG. 24C is a graph comparing the effects of 5-day storage (D5), ultraviolet light (uv) and treatment with Compound 18 at 100 μM (PCD) on platelet function as measured by GMP-140 expression. "n" represents the number of experiments represented by the data point.
Figure 24D:
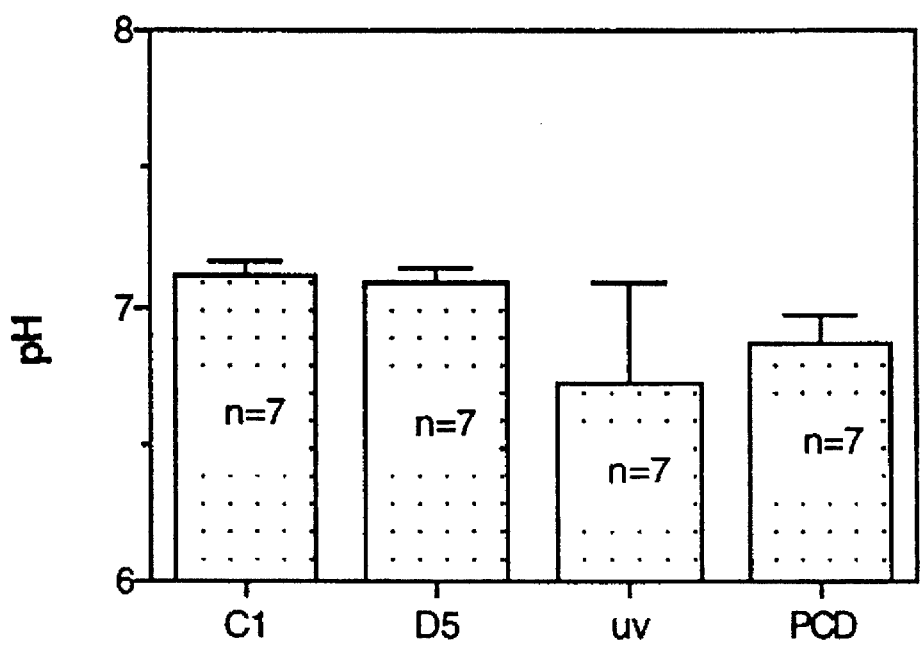
FIG. 24D is a graph comparing the effects of 5-day storage (D5), ultraviolet light (uv) and treatment with Compound 18 at 100 μM (PCD) on platelet function as measured by pH. "n" represents the number of experiments represented by the data point.

FIG. 20C schematically shows one embodiment of the decontamination approach of the present invention applied specifically to platelet concentrate diluted with synthetic media as in FIG. 20B. In this embodiment, platelets have been transferred to a synthetic media bag (301). The photoactivation compound either has already been introduced in the blood collection bag (201) or is present in the synthetic media bag (301). Either the platelets are then expressed into the synthetic media bag via a sterile connection means (as shown) or the synthetic media is expressed into the platelet bag. The bag containing the mixture of platelet concentrate and synthetic media (301), which has UV light transmission properties and other characteristics suited for the present invention, is then placed in a device (such as that described in Example 1, above) and illuminated.

Following phototreatment, the decontaminated platelets are transferred from the synthetic media bag (301) into the storage bag (302) of the two bag set (300). The storage bag can be a commercially available storage bag (e.g., CLX bag from Cutter).

EXAMPLE 19

This example involves an assessment of the impact of the compounds and methods of the present invention on platelet function. Four indicators of platelet viability and function were employed: 1) GMP-140 expression; 2) maintenance of pH; 3) platelet aggregation, and 4) platelet count.

To measure the effects of the present compounds and methods of decontamination on platelet function using these four indicators, four samples were prepared for each compound tested, two control samples and two containing compound. Three units of human platelets were obtained from the Sacramento Blood Center, Sacramento, Calif. These were each transferred under sterile conditions to 50 ml centrifuge tubes, then aliquots of each unit were transferred into a second set of 50 ml sterile centrifuge tubes. To each centrifuge tube containing platelet concentrate (PC), an aliquot of compound stock was added to reach a final concentration of 100 µM of compound. The compounds tested in this experiment were Compound 2 (36 µL of 10 mM stock added to 4 ml PC), Compound 6 (173.5 µl of 9.8 mM stock added to 16.8 ml PC), Compound 17 (2.0 ml of 1 mM stock added to 18 ml PC) and Compound 18 (0.842 ml of 2.0 mM stock to 16 ml PC). The samples were pipetted gently up and down to mix. Then aliquots (either 3 ml or 8 ml) of each sample was transferred to two sterile Teflon™ Medi-bags™ (American Fluoroseal Co., Silver Springs, Md.) (presently owned by The West Company, Lionville, Pa.). Samples were treated in one of two different sized bags, having either 3 ml or 8 ml capacity. The bags both have approximately the same surface area to volume ratios, and previous experiments have shown that the two bags exhibit approximately equivalent properties during irradiation of samples. (Data not shown). For each compound tested, two control samples without compound were prepared by again removing aliquots of platelet concentrate (17 ml if using an 8 ml bag, 4 ml if using a 3 ml bag) from the same one of the first set of 50 ml centrifuge tubes from which the compound sample was drawn, and dividing into Medibags, as before. One of each pair of Medibags containing a compound, and one of each pair of control Medibags, were illuminated for 5 Joules/cm$^2$ on the device described in Example 1, above. Then all experimental and control Medibags were placed on a platelet shaker for storage for 5 days. The same experiments were repeated several times to obtain more statistically meaningful data, as represented by "n", the number of data points represented, in the graphs of FIGS. 21–24, discussed below.

To obtain data for control samples at day one, approximately 3 ml were removed from the remaining volume of each of the three units and divided into two 1.5 ml tubes. These samples were tested for pH as described below. A platelet count was also taken, as described below, at a 1:3 dilution. The residual platelet concentrate from each unit was spun for 10 minutes at 3800 rpm (3000 g) in Sorval RC3B (DuPont Company, Wilmington, Del.) to pellet platelets. Plasma was then decanted into 2 sterile 50 ml tubes (one for Day one, and the other stored at 4° C. for Day 5) for use in the aggregation assay.

1) GMP-140 Expression

When platelets become activated, an alpha granule membrane glycoprotein called p-selectin (GMP140) becomes exposed on the platelet surface. Less than (5%) of fresh, normal unstimulated platelets express detectable GMP140 levels by flow cytometry. See generally M. J. Metzelaar, Studies on the Expression of Activation-Markers on Human Platelets (Thesis 1991).

To measure GMP140, a small aliquot of platelet rich plasma is placed in HEPES buffer containing a GMP140-binding antibody or an isotype control mouse IgG. CD62 is a commercially available monoclonal antibody which binds to GMP140 (available from Sanbio, Uden, the Netherlands; Caltag Labs, So. San Francisco, Calif., and Becton Dickinson, Mountain View, Calif.). After a fifteen minute incubation at room temperature, Goat F(ab')2 Anti-Mouse IgG conjugated to FITC (Caltag Laboratories, So. San Francisco, Calif.) is added to the tube in saturating amounts and allowed to incubate at room temperature (RT) for 15 minutes. Finally, the cells are diluted in 1% paraformaldehyde in phosphate buffered saline and analyzed on a FAC-SCAN™ (Becton Dickinson, Mountain View, Calif.). The positive control is made by adding Phorbol Myristate Acetate (PMA) to the test system at a final concentration of $2\times10^{-7}$ M.

In this example, CD62 was employed to measure the impact, if any, of irradiation in the presence of several compounds of the present invention on platelet activation. The antibody was mixed with HEPES buffer (10 µL antibody [0.1 mg/ml]: 2.49 mL buffer) and stored in 50 µL aliquots at −40° C. prior to use. A positive control consisted of: 10 µL CD62, 8 µL PMA and 2.482 mL Hepes buffer. A mouse IgG1 control (0.05 mg/ml) (Becton Dickinson, Mountain View, Calif. #9040) 5× concentrated was also employed. The antibody was diluted in HEPES buffer (20 µL antibody: 2.48 ml buffer) and stored at −40° C. Phorbol Myristate Acetate (PMA) (Sigma, St. Louis, Mo.) was stored at −40° C. At time of use, this was dissolved in DMSO (working concentration was 10 µg/mL).

1% Paraformaldehyde (PFA) (Sigma, St. Louis, Mo.) was prepared by adding 10 grams paraformaldehyde to 1 liter PBS. This was heated to 70° C., whereupon 3M NaOH was added dropwise until the solution was clear. The solution was cooled and the pH was adjusted to 7.4 with 1N HCl. This was filtered and stored.

Processing each of the samples of platelet concentrate after treatment involved adding 5 microliters of platelet concentrate, diluted 1:3 in Hepes buffer, to each microcentrifuge tube containing the antibody CD62, and appropriate reagents and mixing very gently by vortex. The samples were then incubated for 15 minutes at room temperature.

The Goat anti-Mouse IgG-FITC (diluted 1:10 in HEPES buffer) was added (5 microliters) to each tube and the solution was mixed by gentle vortex. The samples were incubated for an additional 15 minutes at room temperature. Next, 1 ml of 1% PFA in PBS was added to each tube and mixed gently. The platelets were analyzed on the FACS-CAN™. The results are shown in FIGS. 21C, 22C, 23C, and 24C. (FIGS. 21 correspond to Compound 2, FIGS. 22 correspond to Compound 6, FIGS. 23 correspond to Compound 17 and FIG. 24 correspond to Compound 18). Clearly, three of the four compounds tested, 2, 6, and 17, exhibited little or no difference between the day 5 untreated control (D5) and the sample treated with both light and psoralen compound (PCD). Only Compound 18 exhibited a notable increase above the control. But the value was still well below the positive control value.

2) Maintainance of pH:

Changes in pH of platelets in concentrate can alter their morphological characteristics and their survival post transfusion. Moroff, G., et al., "Factors Influencing Changes in pH during Storage of Platelet Concentrates at 20°–24° C.," Vox Sang. 42:33 (1982). The range of pH at which platelets function normally is from approximately 6.0–6.5 to 7.6. Stack, G. and E. L. Snyder, "Storage of Platelet Concentrate," Blood Separation and Platelet Fractionation 99, at 107 (1991). To measure pH of the samples, a CIBA-CORNING 238 pH/Blood Gas analyzer was used (CIBA-CORNING, Norwood, Mass.). A small amount of platelet concentrate from each sample was introduced into the pH/Blood Gas analyzer.

Measurements of pH were taken at time zero and after 5 days of storage for all samples. FIGS. 21D, 22D, 23D and 24D are bar graphs showing pH results for a dark control, a light control and an experimental light plus compound. These graphs indicate that the pH of platelet concentrate samples after illumination in the presence of any one of the compounds remains above a pH of 6.5. Thus platelets remain at a pH acceptable for stored platelets following photoinactivating treatment using compounds of the present invention.

3) Aggregation

Platelet aggregation is measured by the change in optical transmission that a platelet sample exhibits upon stimulation of aggregation. Platelet aggregation was measured using a Whole Blood Aggregometer (Chrono-Log Corp., Havertown, Pa., model 560VS). The number of platelets in each sample was controlled to be constant for every measurement. A Model F800 Sysmex cell counter (Toa Medical Electronics, Kobe, Japan) was used to measure platelet count in the platelet samples and autologous plasma was used to adjust platelet counts to 300,000/mL of platelet concentrate.

For the procedure, all the samples were incubated in a capped plastic tube for 30 minutes at 37° C. for activation. The aggregometer was warmed up to 37° C. The optical channel was used for platelet aggregation measurement. The magnetic speed of the aggregometer was set at 600/min. Remaining platelet concentrate, from the units obtained which was not drawn as a sample for treatment, was centrifuged at high speed (14,000 g) with a micro-centrifuge for 5 minutes to obtain containers of platelet poor plasma autologous to the experimental samples.

To begin, 0.45 ml of the autologous platelet poor plasma was added along with 0.5 ml of saline into a glass cuvette and placed in the PPP channel. Then 0.45 ml of the sample platelet concentrate and 0.50 ml of saline were added to a glass cuvette (containing a small magnet) into the sample channel. After one minute, ADP and collagen reagents (10 µl) each were added to the sample cuvette. The final concentration of ADP was 10 µM and the final concentration of collagen was 5 µg/ml. Platelet aggregation was recorded for about 8–10 minutes or until the maximum reading was reached.

The results appear in FIGS. 21B, 22B, 23B, and 24B. The 100% aggregation line is the level at which the recorder was set to zero. The 0% aggregation line is where the platelets transmitted before the ADP and collagen were added. The aggregation value for the sample is determined by taking the maximum aggregation value as a percent of the total range. Three of the four compounds tested showed very little or no difference in aggregation levels between the samples treated with compound and the untreated samples which were stored for 5 days. Compound 2 exhibited a small reduction in aggregation, of approximately 8% from the day 1 control. The aggregation for the sample treated with compound and uv was the same as that for the uv only sample. This is supporting evidence that the decontamination compounds tested do not have a significant effect on platelet aggregation when used in the methods of the present invention.

4) Count

A Sysmex cell counter was used to measure platelet count in the platelet samples. Samples were diluted 1:3 in blood bank saline.

The results of the platelet count measurements appear in FIGS. 21A, 22A, 23A, and 24A. For each of the compounds, the samples show little or no drop in platelet count between the Day 5 control and the Day 5 treated sample. Interestingly, samples treated with Compounds 6, 17 and 18 all display a higher platelet count than samples treated with light alone. For example, samples treated with Compound 6 had counts equivalent to the 5 day control, but samples treated with only ultraviolet light showed approximately a 33% reduction in platelet count. Thus, not only is treatment with compounds of the present invention compatible with the maintenance of platelet count, but it actually appears to prevent the drop in count caused by ultraviolet light exposure.

EXAMPLE 20

A preferred compound for decontaminating blood subsequently used in vivo should not be mutagenic to the recipient of the blood. In the first part of this experiment, some compounds were screened to determine their genotoxicity level in comparison to aminomethyltrimethylpsoralen. In the second part, the in vivo clastogenicity of some compounds of the present invention was measured by looking for micronucleus formation in mouse reticulocytes.

1) Genotoxicity

Mammalian cell cultures are valuable tools for assessing the clastogenic potential of chemicals. In such studies, cells are exposed to chemicals with and/or without rat S-9 metabolic activation system (S-9) and are later examined for either cell survival (for a genotoxicity screen) or for changes in chromosome structure (for a chromosome aberration assay).

Chinese hamster ovary (CLIO; ATCC CCL 61 CHO-K1, proline-requiring) cells were used for the in vitro genotoxicity and chromosomal aberration tests. CHO cells are used extensively for cytogenic testing because they have a relatively low number of chromosomes (2n=20) and a rapid rate of multiplication (~12 to 14 hours, depending on culture conditions). The cells were grown in an atmosphere of 5% $CO_2$ at approximately 37° C. in McCoy's 5a medium with 15% fetal bovine serum (FBS), 2 mM L-glutamine, and 1% penicillin-streptomycin solution to maintain exponential growth. This medium was also used during exposure of the cells to the test compound when no S-9 was used. Cell cultures were maintained and cell exposures were performed in T-75 or T-25 flasks.

Each of the sample compounds were tested at seven dilutions, 1, 3, 10, 33, 100, 333, and 1000 µg/ml. The compound was added in complete McCoy's 5a medium. After the compound was added, cells were grown in the dark at approximately 37° C. for approximately 3 hours. The medium containing the test compound was then aspirated, the cells were washed three times with phosphate-buffered saline (PBS) at approximately 37° C., and fresh complete McCoy's 5a medium was added. The positive control was methylmethane sulfonate. The solvent control was dimethylsulfoxide (DMSO) diluted in culture medium. For assays using metabolic activation (see below) the activation mixture was also added to the solvent control. The cultures were then incubated for an additional time of approximately 12 hours before they were harvested. Colchicine (final concentration, 0.4 µg/ml) was added approximately 2.5 hours prior to the harvest.

After approximately 2.5 hours in colchicine, the cells were harvested. Cells were removed from the surface of the flasks using a cell scraper. The resulting cell suspension was centrifuged, the supernatant, aspirated, and 4 ml of a hypotonic solution of 0.075M KCl added to the cells for 15 minutes at approximately 37° C. The cells were then centrifuged, the supernatant aspirated, and the cells suspended in a fixative of methanol: acetic acid (3:1). After three changes of fixative, air-dried slides were prepared using cells from all flasks. The cell density and metaphase quality on the initial slide from each flask was monitored using a phase-contrast microscope; at least two slides of appropriate cell density were prepared from each flask. The slides were stained in 3% Giemsa for 20 min, rinsed in deionized water, and passed through xylene. Coverslips were mounted with Permount. Slides are then examined to determine what concentration of each test compound represented a toxic dose.

An analysis of the results showed that AMT was genotoxic at 30 µg/ml. In contrast, Compounds 2 and 6 were only genotoxic at 100 µg/ml, more than three times the toxic dose of AMT.

A psoralen compound with a structure distinct from compounds of the present invention, 8-aminomethyl-4,4',5'-trimethylpsoralen, was also tested in this experiment and proved to be toxic at 10 µg/ml. While the 8-substituted aminomethyl compound and similar structures may not be suited for methods of the present invention, they may be useful for alternative purposes. In light of the ability of the compounds to prevent nucleic acid replication, in combination with their extreme toxicity, the compounds could be used, for example, to treat diseases characterized by uncontrolled cell growth, such as cancer.

2) Micronucleus Assay Protocol

Saline solutions were prepared for Compounds 2, 6, 17 and 18 at various concentrations. Male Balb/c mice were then injected with 0.1 ml of a compound solution via the tail vein. At least 3 mice were injected per dose level. Saline only was used as a negative control. For a positive control, cyclophosphamide (cycloPP) was administered at a dose of 30 mg/kg. In the experimental group, the injections were repeated once per day for four days. In the positive control group, the sample was administered only once, on day three. On day 5, several microliters of blood were withdrawn from each subject and smeared on a glass slide. Cells were fixed in absolute methanol and stored in a slide rack.

For analysis, cells were stained with acridine orange and visualized under a fluorescence microscope by counting: (i) the number of reticulocytes per 5000 erythrocytes; and (ii) the number of micronucleated reticulocytes per 1000 reticulocytes. Reticulocytes were distinguished by their red fluorescence due to the presence of RNA. Micronuclei were distinguished by their green fluorescence due to the presence of DNA. The percentage of reticulocytes (%PCE) was then calculated. A decrease in the frequency of erythrocytes, represented by an increase in the percentage of reticulocytes, is an indication of bone marrow toxicity. The percentage of reticulocytes with micronuclei (%PCE with MN) was also calculated. An increase in %PCE with MN is a measure of clastogenicity.

of each of the dark controls was placed in a cryovial and stored in the dark at −80° C. For UVA illumination, 8 ml of

TABLE 20

| COMPOUND | DOSE (mg/kg) | PCE/RBC (%) | PCE + MN (%) | #duplicates |
|---|---|---|---|---|
| 2 | 40 | 3.08 ± 0.82 | 0.20 ± 0.14 | 4 |
| 2 | 25 | 3.46 ± 0.32 | 0.25 ± 0.11 | 6 |
| CycloPP | 30 | 1.65 ± 0.64 | 1.98 ± 0.40 | 6 |
| saline | | 3.49 ± 0.55 | 0.18 ± 0.13 | 6 |
| 6 | 45 | 3.79 ± 0.41 | 0.36 ± 0.14 | 3 |
| 6 | 30 | 3.61 ± 0.12 | 0.27 ± 0.38 | 3 |
| 17 | 45 | 5.7 ± 2.14 | 0.31 ± 0.07 | 3 |
| 17 | 30 | 3.47 ± 0.83 | 0.30 ± 0.17 | 3 |
| CycloPP | 30 | 0.99 ± 0.33 | 1.76 ± 0.64 | 3 |
| saline | | 3.47 ± 0.44 | 0.23 ± 0.15 | 3 |
| 18 | 20 | 3.48 ± 0.79 | 0.17 ± 0.06 | 3 |
| 18 | 7.5 | 3.59 ± 0.33 | 0.43 ± 0.12 | 3 |
| 18 | 3.75 | 3.61 ± 1.14 | 0.17 ± 0.12 | 3 |
| CycloPP | 30 | 1.39 ± 0.41 | 2.09 ± 0.17 | 3 |
| saline | | 3.31 ± 0.63 | 0.36 ± 0.11 | 3 |

After initial results were determined, the experiment was repeated using increased dose levels, until: (i) Micronucleus formation was seen; or (ii) Bone marrow toxicity was observed; or (ii) The lethal dose was reached; or (iv) A dose of 5 g/kg was administered. For the assays with each of the compounds 2, 6, 17 and 18, the acutely lethal dose was reached before there were any signs of bone marrow toxicity or micronucleus formation. The results of the experiment appear in Table 20, below. As is clear from the table, no bone marrow toxicity was observed for any of the compounds at the doses tested. The percent reticulocyte value for treatment with each compound remained close to the negative control value. This is in contrast with a drop of approximately 2%–2.5% PCE/RBC seen in the positive control, representing erythrocyte depletion due to bone marrow toxicity. Nor did any of the compounds display clastogenic action.

EXAMPLE 21

In EXAMPLE 13, the inactivation of cell-free HIV virus, using compounds and methods of the present invention, is shown. This example shows inactivation of cell-associated HIV also using compounds of the present invention.

H9 cells chronically infected with $HIV_{IIIB}$ were used. (H9/HTLV-III-B NIH 1983 Cat.#400). Cultures of these cells were maintained in high glucose Dulbecco Modified Eagle Medium supplemented with 2 mM L-glutamine, 200 u/mL penicillin, 200 μg/ml streptomycin, and 9% fetal bovine serum (Intergert Company, Purchase, N.Y.) For maintenence, the culture was split once a week, to a density of $3 \times 10^5$ to $4 \times 10^5$ cells/ml and about four days after splitting, 3.3% sodium bicarbonate was added as needed. For the inactivation procedure, the cells were used three days after they were split. They were pelleted from their culture medium at 400 g×10 minutes, the supernatant was discarded, and the cells were resuspended in one to five day old human platelet concentrate (PC) (pH 7.5–6.5), to a concentration of $2 \times 10^6$ cells/ml. Aliquots of the PC-infected cell suspension were made for psoralen free dark controls, for sporalen free UVA only controls, for psoralen dark controls, and for the psoralen plus UVA experimental sample. Concentrated filter-sterilized stock solutions of each psoralen in water were diluted into the appropriate aliquots to yield a final concentration of 150 μM. (A 10 mM stock of Compound 18 was diluted about 67-fold and a 2 mM stock of Compound 2 was diluted about 13-fold). After an equilibration period of thirty minutes at room temperature, 0.5 ml of the psoralen free aliquot and 8 ml of each psoralen containing aliquot were introduced into a modified Fl 20 Teflon™ bag (modified to be 92 cm² total surface area, The West Co., Phoenixville, Pa.) via a plastic disposable 10 ml syringe attached to one of the polypropylne ports on the bag. This gave an average path length of 0.17 cm. The bags were then illuminated for a total exposure of 3 Joules/cm² in the device described in Example 1, above, attached to a circulating refrigerating waterbath set at 4° C., which maintains the temperature in the bag at approximately 22°–25° C. During exposure, the device was shaken on a platelet shaker (Helmer Labs, Noblesville, Ind.). After exposure, the contents of the bags were withdrawn by a fresh syringe through the remaining unused port on the bag, and placed in cryovials for storage in the dark at −80° C. until analysis.

The stored samples were thawed at 37° C., then fitrated in an HIV microplaque assay, as described in Hanson, C. V., Crawford-Miksza, L. and Sheppard, H. W., J. Clin. Micro 28:2030 (1990), and as described in EXAMPLE 13, above, with the following modifications. Clot removal from each sample was performed before plating. Because plating of a target volume of 4 ml after clot removal was desired, an excess of sample (6 ml) was transferred to a polypropylene tube and diluted to a final volume of 60 ml with Test and control samples from the inactivation procedure were diluted in 50% assay medium and 50% normal human pooled plasma. The samples were serially diluted directly in 96-well plates (Corning Glass Works, Corning, N.Y.). The plates were mixed on an oscillatory shaker for 30 seconds and incubated at 37° C. in a 5% $CO_2$ atmosphere for 1 to 18 hours. MT-2 cells (0.025 mL) [clone alpha-4, available (catalog number 237) from the National Institutes of Health AIDS Research and Reference Reagent Program, Rockville, Md.] were added to each well to give a concentration of 80,000 cells per well. After an additional 1 hour of incubation at 37° C. in 5% $CO_2$, 0.075 mL of assay medium containing 1.6% SeaPlaque agarose (FMC Bioproducts, Rockland, Me.) and prewarmed to 38.5° C. was added to each well. The plates were kept at 37° C. for a few minutes until several plates had accumulated and then centrifuged in plate carriers at 600×g for 20 minutes in a centrifuge precooled to 10° C. In the centrifuge, cell monolayers formed prior to gelling of the agarose layer. The plates were incubated for 5 days at 37° C in 5% $CO_2$ and stained by the addition of 0.05 mL of 50 μg/mL propidium iodide (Sigma Chemical Co.) in phosphate-buffered saline (pH 7.4) to each well. After 24 to 48 hours, the red fluorescence-stained microplaques were visualized by placing the plates on an 8,000 μW/cm² 304 nm UV light box (Fotodyne, Inc., New Berlin, Wis.). The plaques were counted at a magnification of ×20 to ×25 through a stereomicroscope.

The results were as follows: Compound 2 (150 μM) inactivated >6.7 logs of HIV after 3 Joules/cm² irradiation (compared to dark and light controls of 0 log inactivation, starting log titer 6.1 plaque forming units/ml). At the same concentration and irradiation time, Compound 18 inactivated >7.2 logs of HIV (compared to a dark control of 0 logs and a light control of 0.1 logs, starting titer 6.6). This example supports that the compounds of the present invention are effective in inactivating cell associated virus.

EXAMPLE 22

This example involves an assessment of new synthetic media formulations as measured by the following in vitro platelet function assays: 1) maintenance of pH; 2) platelet aggregation ("Agg") and 3) GMP140 expression. The assays for each of these tests have been described above.

Four formulations were prepared: S 2.19, S 2.22, S 3.0 and S.4.0. The composition of these synthetic media formulations are shown in Table 21 below:

TABLE 21*

|  | S 2.19 | S 2.22 | S 3.0 | S 4.0 |
|---|---|---|---|---|
| Na gluconate | 23 | 0 | 0 | 0 |
| Na acetate | 27 | 20 | 20 | 20 |
| glucose | 0 | 2 | 2 | 2 |
| mannitol | 30 | 20 | 0 | 20 |
| KCl | 5 | 4 | 4 | 4 |
| NaCl | 45 | 80 | 100 | 90 |
| Na₃ citrate | 15 | 15 | 10 | 10 |
| Na phosphate | 20 | 20 | 20 | 20 |
| MgCl₂ | 0 | 3 | 2 | 2 |

*Amounts in mM

One unit of human platelet rich plasma (PRP) was obtained from the Sacramento Blood Bank. The unit was centrifuged at room temperature for 6 minutes at 4000 rpm and then transferred to a unit press. Using an attached transfer line, plasma was expressed from the unit, leaving approximately 9.4 mls of residual plasma.

The unit was allowed to rest for 1 hour, after which it was gently kneaded to resuspend the platelets. To 0.6 ml of the suspension, 2.4 ml of plasma was added back and the entire contents transferred to a Teflon™ minibag. The reconstituted unit was assayed for pH and other tests the next day, with the following results:

| pH | 7.19 |
|---|---|
| GMP140 | 62% |
| Agg | 58% |

The remaining unit was then used to evaluate synthetic media for platelet storage with and without photodecontamination. Aliquots (0.8 ml) from the unit were added to each formulation (3.2 mls) in tubes. 3 mls of each mixture was transferred to a Teflon™ minibag (final plasma concentration of 20%).

Five days later, platelet function was assessed using the battery of tests described above. The resttits for each of the synthetic media formulations are shown in Table 22 below.

TABLE 22

|  | no light | | light | |
|---|---|---|---|---|
|  | S 2.19 | S 2.22 | S 2.19 | S 2.22 |
| pH | 6.86 | 6.82 | 6.83 | 6.60 |
| GMP140 | 87% | 74% | 90% | 80% |
| Agg | 30 | 48 | 16 | 31 |

It appeared that the synthetic media containing 2 mM glucose (i.e., S 2.22) maintained platelet function, as measured by GMP140 and Aggregation, better than the synthetic media that did not contain glucose (i.e., S 2.19).

To confirm the above finding, experiments were repeated ("n" being the number of replicate experiments) with these formulations as well as additional glucose-free formations (3.0 and 4.0). Platelet function was evaluated both before and after storage, and in conjunction with photodecontamination. A summary of the results is provided in Tables 23, 24 and 25 below.

TABLE 23*

|  | Plasma n = 17 | S 2.22 n = 22 | S 3.0 n = 4 | S 4.0 n = 4 | S 2.19 n = 23 |
|---|---|---|---|---|---|
| pH | 7.31 | 7.14 | 7.12 | 7.13 | 7.04 |
| Agg | 82 | 83 | 76 | 78 | 81 |
| GMP-140 | 52 | 49 | 46 | 45 | 68 |

*No UVA; Day 1 of Storage

TABLE 24*

|  | Plasma n = 18 | S 2.22 n = 20 | S 3.0 n = 4 | S 4.0 n = 4 | S 2.19 n = 23 |
|---|---|---|---|---|---|
| pH | 7.03 | 6.92 | 6.93 | 6.93 | 6.96 |
| Agg | 75 | 70 | 67 | 70 | 64 |
| GMP-140 | 61 | 63 | 63 | 64 | 74 |

*No UVA; Day 5 of Storage

TABLE 25*

|  | S 2.22 n = 20 | S 3.0 n = 4 | S 4.0 n = 4 | S 2.19 n = 22 |
|---|---|---|---|---|
| pH | 6.80 | 6.78 | 6.79 | 6.95 |
| Agg | 59 | 54 | 54 | 58 |
| GMP-140 | 73 | 76 | 76 | 83 |

*3 Joules UVA; Day 5 of Storage

It is to be understood that the invention is not to be limited to the exact details of operation or exact compounds, composition, methods, or procedures shown and described, as modifications and equivalents will be apparent to one skilled in the art.

We claim:

1. A method of synthesizing 4,8-dialkyl-4'-bromomethyl-5'-methylpsoralens, without performing bromomethylation, comprising:

a) providing 4,8-dialky-7-(1-methyl-2-oxopropyloxy) psoralen;

d) stirring 4,8-dialky-4',5'-dimethylpsoralen in methylene chloride to obtain 4,8-dialkyl-4'-bromomethyl-5'-methylpsoralen.

2. A method of synthesizing 4,8-dialkyl-5'-bromomethyl-4'-methylpsoralens, without performing bromomethylation, comprising:

a) providing 4,8-dialky-7-(1-methyl-2-oxopropyloxy) psoralen;

d) stirring 4,8-dialky-4',5'-dimethylpsoralen in carbon tetrachloride to obtain 4,8-dialkyl-5'-bromomethyl-4'-methylpsoralen.

* * * * *

UNITED STATES PATENT AND TRADEMARK OFFICE
CERTIFICATE OF CORRECTION

PATENT NO.   : 5,625,079
DATED        : April 29, 1997
INVENTOR(S)  : Susan Wollowitz et al.

It is certified that error appears in the above-identified patent and that said Letters Patent is hereby corrected as shown below:

Title page,
Item [56], OTHER PUBLICATIONS, "Hilfenhaus, J., et al." reference, please delete "70:589" and insert -- 15:251-263 --.

Column 1,
Line 20, please delete "improve" and insert -- improved --.
Line 21, please delete "reduce" and insert -- reduced --.

Column 17,
Line 1, please delete "intermadiate", and insert -- intermediate --.

Column 66,
Line 60, after "4,8-dialkyl-5'-bromomethyl-4'-methylpsoralens" please delete "without performing bromomethylation, comprising:
a) providing 4,8-dialky-7-(1-methyl-2-oxopropyloxy) psoralen;
d) stirring 4,8-dialky-4',5'-dimethylpsoralen in methylene chloride to obtain 4,8-dialkyl-4'-bromomethyl-5'-methylpsoralen." and insert -- comprising:
a)      providing 4,8-dialky-4',5'-dimethylpsoralen;
d)      reacting said 4,8-dialky-4',5'-dimethylpsoralen with N-bromosuccinimide in carbon tetrachloride to obtain 4,8-dialkyl-5'-bromomethyl-4'-methylpsoralen. --

Column 67,
Line 2, please delete "without performing bromomethylation".
Line 4, please delete "4,8-dialky-7-(1-methyl-2-oxopropyloxy) psoralen", and insert -- 4,8-dialky-4',5'-dimethylpsoralen; --.

UNITED STATES PATENT AND TRADEMARK OFFICE
CERTIFICATE OF CORRECTION

PATENT NO.    : 5,625,079
DATED         : April 29, 1997
INVENTOR(S)   : Susan Wollowitz et al.

It is certified that error appears in the above-identified patent and that said Letters Patent is hereby corrected as shown below:

Column 68,
Line 1, please delete "d) stirring 4,8-dialky-4',5'-dimethylpsoralen in carbon tetrachloride to obtain 4,8-dialkyl-5'-bromomethyl-4'-methlpsoralen", and insert -- d) reacting said 4,8-dialky-4',5'-dimethylpsoralen with N-bromosuccinimide in methylene chloride to obtain 4,8-dialkyl-4'-bromomethyl-5'-methylpsoralen --.

Signed and Sealed this

Eighteenth Day of March, 2003

JAMES E. ROGAN
*Director of the United States Patent and Trademark Office*

UNITED STATES PATENT AND TRADEMARK OFFICE
Certificate

Patent No. 5,625,079                                                     Patented: April 29, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Susan Wollowitz, Lafayette, CA (US); Henry Rapoport, Berkeley, CA (US); Hans P. Spielmann, Lexington, KY (US); and Aileen Nerio, Freemont, CA (US).

Signed and Sealed this Fifth Day of January 2010.

MICHAEL P. WOODWARD
*Supervisory Patent Examiner*
Technology Center 1600